US012350036B2

(12) United States Patent
Nishioka et al.

(10) Patent No.: US 12,350,036 B2
(45) Date of Patent: Jul. 8, 2025

(54) INFORMATION PROCESSING APPARATUS, INFORMATION PROCESSING METHOD, AND INFORMATION PROCESSING PROGRAM

(71) Applicant: SONY GROUP CORPORATION, Tokyo (JP)

(72) Inventors: Hayato Nishioka, Tokyo (JP); Takanori Oku, Tokyo (JP); Shinichi Furuya, Tokyo (JP); Takahisa Ishikawa, Tokyo (JP); Yuki Ogasawara, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 315 days.

(21) Appl. No.: 17/790,653

(22) PCT Filed: Dec. 28, 2020

(86) PCT No.: PCT/JP2020/049060
§ 371 (c)(1),
(2) Date: Jul. 1, 2022

(87) PCT Pub. No.: WO2021/140976
PCT Pub. Date: Jul. 15, 2021

(65) Prior Publication Data
US 2023/0041782 A1 Feb. 9, 2023

(30) Foreign Application Priority Data

Jan. 8, 2020 (JP) .................................. 2020-001698
Nov. 13, 2020 (JP) .................................. 2020-189088

(51) Int. Cl.
*A61B 5/11* (2006.01)
*A61B 5/00* (2006.01)
(Continued)

(52) U.S. Cl.
CPC ............ *A61B 5/1125* (2013.01); *A61B 5/225* (2013.01); *A61B 5/6826* (2013.01); *A61B 5/702* (2013.01);
(Continued)

(58) Field of Classification Search
CPC ..... A61B 5/1125; A61B 5/225; A61B 5/6826; A61B 5/702; A61H 1/0288;
(Continued)

(56) References Cited

U.S. PATENT DOCUMENTS 5,317,916 A * 6/1994 Kovacevic ............. A63B 23/16
73/379.03
2001/0049482 A1 12/2001 Pozos
(Continued)

FOREIGN PATENT DOCUMENTS

CN 107485827 A * 12/2017
CN 109549819 A * 4/2019 ........... A61H 1/0288
(Continued)

OTHER PUBLICATIONS

CN-107485827-A (Year: 2017).*
(Continued)

*Primary Examiner* — Ryan D Walsh
(74) *Attorney, Agent, or Firm* — Paratus Law Group, PLLC

(57) ABSTRACT

An information processing apparatus (100) according to the present application includes two or more force sensors (110) that each detect a force of two or more different fingers of a user, and a processing unit (122) that executes information processing related to measurement of forces of the two or more different fingers based on detection results detected by each of the two or more force sensors (110).

19 Claims, 47 Drawing Sheets

(51) Int. Cl.
*A61B 5/22* (2006.01)
*A61H 1/02* (2006.01)
*A63B 21/00* (2006.01)
*A63B 23/16* (2006.01)
*A63F 13/218* (2014.01)
*G01L 5/16* (2020.01)
*A63B 71/06* (2006.01)
*G09B 15/06* (2006.01)

(52) U.S. Cl.
CPC ......... *A61H 1/0288* (2013.01); *A63F 13/218* (2014.09); *G01L 5/16* (2013.01); *A61H 2205/067* (2013.01); *A63B 21/4035* (2015.10); *A63B 23/16* (2013.01); *A63B 2071/0647* (2013.01); *A63B 2220/51* (2013.01); *A63B 2220/56* (2013.01); *A63F 2300/1056* (2013.01); *G09B 15/06* (2013.01)

(58) Field of Classification Search
CPC ............. A61H 2205/067; A63F 13/218; A63F 2300/1056; G01L 5/16; A63B 21/4035; A63B 23/16; A63B 2071/0647; A63B 2220/51; A63B 2220/56; G09B 15/06
See application file for complete search history.

(56) References Cited

U.S. PATENT DOCUMENTS

2014/0266812 A1   9/2014   Rajkowski
2016/0144228 A1*  5/2016   Jung ................. A63B 21/4019
                                                          482/8
2018/0228407 A1   8/2018   Olds
2022/0062756 A1*  3/2022   Lyden ................. A63F 13/218

FOREIGN PATENT DOCUMENTS

| | | |
|---|---|---|
| EP | 2659835 | 11/2013 |
| JP | 2007-196742 A | 8/2007 |
| JP | 2013-008324 A | 1/2013 |
| JP | 2014-008324 A | 1/2014 |
| JP | 2016-097295 A | 5/2016 |
| JP | 2018-519133 A | 7/2018 |
| KR | 101500483 B1 * | 3/2015 |
| WO | WO-2016184935 A2 | 11/2016 |
| WO | WO-2019122885 A | 6/2019 |

OTHER PUBLICATIONS

CN-109549819-A, English (Year: 2019).*
KR-101500483-B1, English (Year: 2015).*
Germanotta Marco et al: "Reliability, validity and discriminant ability of a robotic device for finger training in patients with subacute stroke", Journal of Neuroengineering and Rehabilitation, (Online) vol. 17, No. 1, Jan. 3, 2020 (Jan. 3, 2020) XP093034629.
Xu Jing et al: "Separable systems for recovery of finger strength and control after stroke", Journal of Neurophysiology, vol. 118, No. 2, Aug. 1, 2017 (Aug. 1, 2017), pp. 1151-1163, XP093034438, US.
Xu Jing et al:"Recovery of hand function after stroke:separable systems for finger strength and control",bioRxiv,Oct. 7, 2016(Oct. 7, 2016),p. 1-52,XP093034445.

* cited by examiner

INFORMATION PROCESSING APPARATUS, INFORMATION PROCESSING METHOD, AND INFORMATION PROCESSING PROGRAM

CROSS REFERENCE TO PRIOR APPLICATION

This application is a National Stage Patent Application of PCT International Patent Application No. PCT/JP2020/049060 (filed on Dec. 28, 2020) under 35 U.S.C. § 371, which claims priority to Japanese Patent Application Nos. 2020-001698 (filed on Jan. 8, 2020) and 2020-189088 (filed on Nov. 13, 2020), which are all hereby incorporated by reference in their entirety.

FIELD

The present invention relates to an information processing apparatus, an information processing method, and an information processing program.

BACKGROUND

Conventionally, there has been known a technique for measuring a function and a skill of a finger for the purpose of skill training of a musical instrument player, rehabilitation of a person suffering from a motor organ disease, and the like. For example, a technique for measuring independent muscle strength of a thumb and a finger has been proposed.

CITATION LIST

Patent Literature

Patent Literature 1: JP 2013-008324 A

SUMMARY

Technical Problem

However, with the above-described conventional technique, it is not always possible to appropriately measure the force of a finger. For example, with the above-described conventional technique, since merely the independent muscle strength of a thumb and a finger is measured, it is not always possible to appropriately measure the force of the finger.

Therefore, the present disclosure proposes an information processing apparatus, an information processing method, and an information processing program capable of appropriately measuring the force of the finger.

Solution to Problem

To solve the above problem, an information processing apparatus according to the present application includes two or more force sensors that each detect a force of two or more different fingers of a user, and a processing unit that executes information processing related to measurement of forces of the two or more different fingers based on detection results detected by each of the two or more force sensors.

DESCRIPTION OF EMBODIMENTS

Figure 1:
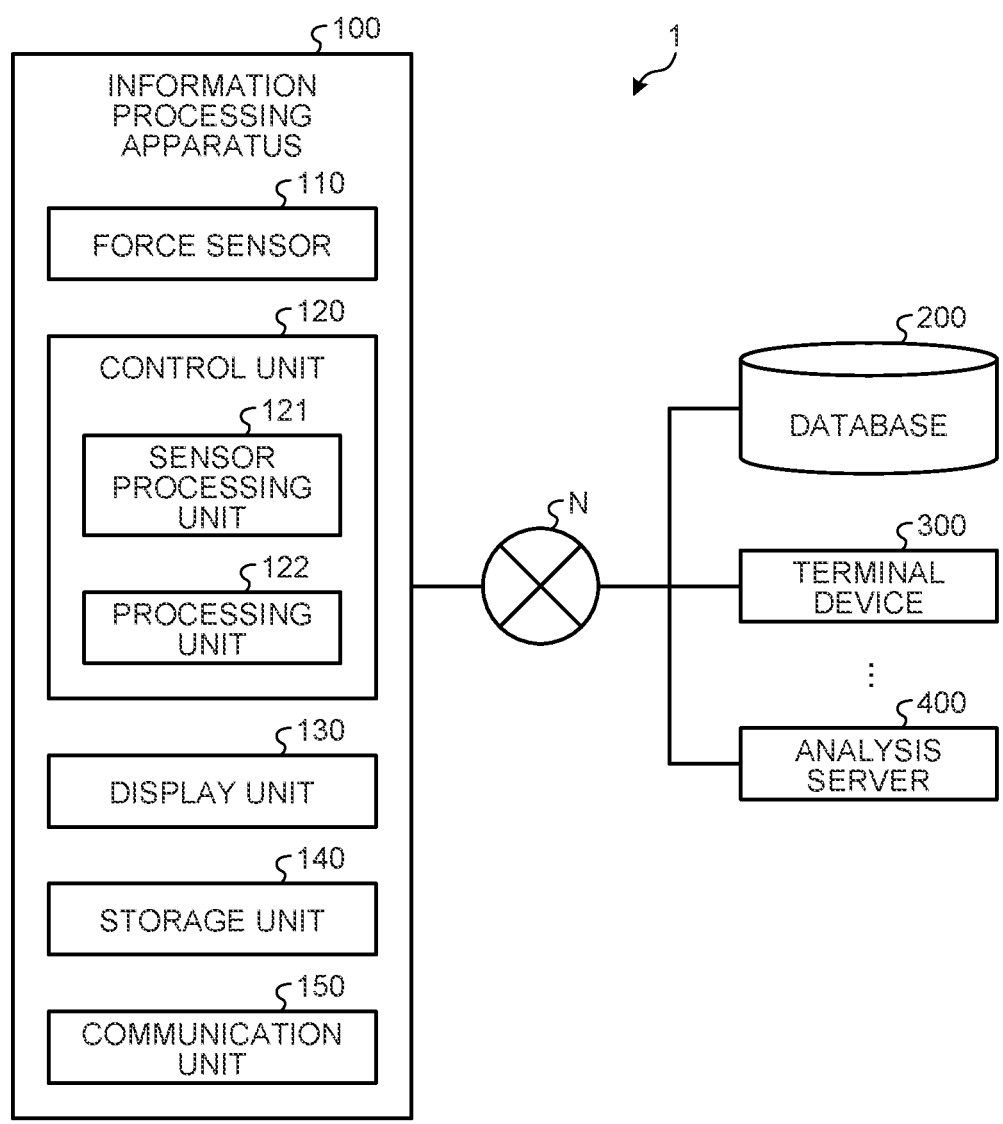
FIG. 1 is a block diagram illustrating a configuration example of an information processing system according to an embodiment.

Hereinafter, embodiments of the present disclosure will be described in detail with reference to the drawings. Note that, in the following embodiments, the same parts are denoted by the same reference numerals so that redundant description can be omitted.

The present disclosure will be described according to the following item order.

1. Embodiment
1-1. Configuration of an information processing system
1-2. Force sensor
1-3. Measurement of force of a finger
1-4. Measurement of independence of a finger
1-5. Measurement of agility of a finger
1-6. Measurement of repetitive reproducibility of tapping force of a finger
1-7. Measurement of temporal accuracy of tapping operation of a finger
1-8. Training of independence of a finger
1-9. Evaluation and recommendation
1-10. First modification
1-11. Second modification
2. Effects related to the present disclosure
3. Hardware configuration

1. Embodiment

1-1. Configuration of an Information Processing System

First, a configuration example of an information processing system according to an embodiment will be described with reference to FIG. 1. FIG. 1 is a block diagram illustrating a configuration example of the information processing system according to the embodiment.

As illustrated in FIG. 1, the information processing system 1 includes an information processing apparatus 100, a database 200, a terminal device 300, and an analysis server 400. The information processing apparatus 100, and the database 200, the terminal device 300, or the analysis server 400 are communicably connected by wire or wirelessly via a predetermined network N. In addition, the information processing system 1 illustrated in FIG. 1 may include a plurality of information processing apparatuses 100, a plurality of databases 200, a plurality of terminal devices 300, and a plurality of analysis servers 400.

(Information Processing Apparatus 100)

The information processing apparatus 100 includes a force sensor 110, a control unit 120, a display unit 130, a storage unit 140, and a communication unit 150. In addition, the information processing apparatus 100 may have an input unit (for example, a keyboard, a mouse, etc.) that receives various operations from an administrator or the like of the information processing apparatus 100.

(Force Sensor 110)

The force sensor 110 includes two or more force sensors that each detect a force of two or more different fingers of a user. Specifically, the force sensor 110 includes five sensor units 110A that each detect a force of five fingers of the user. The force sensor 110 may include any number of force sensors such as three or four, not limited to five, as long as the number is two or more. Details of the structure of the force sensor 110 will be described with reference to FIGS. 2 to 6 described later.

The force sensor 110 is realized by, for example, a load cell, a force sensor, a pressure sensor, a distance sensor combined with a spring mechanism, a photo-reflector combined with a spring mechanism, or the like.

(Control Unit 120)

The control unit 120 is a controller, and is realized when, for example, a central processing unit (CPU), a micro processing unit (MPU), or the like executes various programs (corresponding to an example of an information processing program) stored in a storage device inside the information processing apparatus 100 using a RAM as a work area. In addition, the control unit 120 is a controller, and is realized by, for example, an integrated circuit such as an application specific integrated circuit (ASIC) or a field programmable gate array (FPGA).

As illustrated in FIG. 1, the control unit 120 has a sensor processing unit 121 and a processing unit 122, and realizes or executes actions of information processing described below. The internal configuration of the control unit 120 is not limited to the configuration illustrated in FIG. 1, and may be another configuration as long as it performs information processing described later.

(Sensor Processing Unit 121)

The sensor processing unit 121 performs sampling of a signal detected by the force sensor, noise reduction, filter application, and processing of converting a force into a voltage.

(Processing Unit 122)

The processing unit 122 executes information processing related to measurement of the forces of the two or more different fingers based on detection results detected by each of the two or more force sensors. Specifically, the processing unit 122 executes information processing related to the measurement of the forces of the five different fingers based on detection results detected by each of the five force sensors.

More specifically, the processing unit 122 measures the magnitude of the force input to each of the two or more force sensors. For example, the processing unit 122 measures the magnitude of the force input to each of the five force sensors. Processing of measuring the force of the finger by the processing unit 122 will be described in detail with reference to FIG. 7 described later.

In addition, the processing unit 122 measures information indicating a relation between the forces input to each of the two or more force sensors. For example, the processing unit 122 measures information indicating a relation between the forces input to each of the five force sensors. That is, the processing unit 122 measures a relation between the forces of the five different fingers. Here, measuring the relation between the forces of the five different fingers can be rephrased as measuring how independent each force of the fingers is from the forces of the other four fingers (hereinafter, also referred to as independence). Processing of measuring the independence of the finger by the processing unit 122 will be described in detail with reference to FIG. 11 described later.

In addition, the processing unit 122 measures the number of times of forces input to at least one of the two or more force sensors within a predetermined time. For example, the processing unit 122 measures the number of times of forces input to at least one of the five force sensors within a predetermined time. Here, inputting the force of the finger to the force sensor can be rephrased as pressing the force sensor by the finger (hereinafter, also referred to as tapping). That is, the processing unit 122 measures the number of times that each of the five different fingers taps the force sensor within a predetermined time (hereinafter, also referred to as agility). Processing of measuring the agility of the finger by the processing unit 122 will be described in detail with reference to FIG. 16 described later.

In addition, the processing unit 122 measures variation in the magnitude between the forces input to at least one of the two or more force sensors. For example, the processing unit 122 measures variation in the magnitude between the forces input to at least one of the five force sensors. Here, measuring the variation in magnitude between forces input to the force sensors (hereinafter, also referred to as tapping force) can be rephrased as measuring the uniformity in magnitude with which each finger can tap the force sensor (hereinafter, also referred to as repetitive reproducibility of tapping force). That is, the processing unit 122 measures the repetitive reproducibility of the tapping force of each of the five different fingers. Processing of measuring the repetitive reproducibility of the tapping force of the finger by the processing unit 122 will be described in detail with reference to FIG. 19 described later.

In addition, the processing unit 122 measures a time interval between the forces input to at least one of the two or more force sensors. For example, the processing unit 122 measures a time interval between the forces input to at least one of the five force sensors. Here, measuring the time interval between the forces input to the force sensor can be rephrased as measuring the uniformity in tempo with which each finger can perform tapping operation (hereinafter, also referred to as temporal accuracy of tapping operation). That is, the processing unit 122 measures the temporal accuracy of the tapping operation of each finger. Processing of measuring the temporal accuracy of the tapping operation of the finger by the processing unit 122 will be described in detail with reference to FIG. 21 described later.

(Display Unit 130)

The display unit 130 displays information related to measurement results of the forces of the two or more different fingers measured by the processing unit 122. Specifically, the display unit 130 displays information indicating the relation between the forces of the two or more different fingers measured by the processing unit 122. A specific example of the display screen by the display unit 130 will be described in detail with reference to FIG. 8, etc. described later.

(Storage Unit 140)

The storage unit 140 is realized by, for example, a semiconductor memory element such as a random access memory (RAM) or a flash memory, or a storage device such as a hard disk or an optical disk. The storage unit 140 stores the detection results detected by each of the two or more force sensors. In addition, the storage unit 140 stores the measurement results of the forces of the two or more different fingers by the processing unit 122.

(Communication Unit 150)

The communication unit 150 is realized by, for example, a network interface card (NIC) or the like. Then, the communication unit 150 is connected to the network by wire or wirelessly, and transmits and receives information to and from the database 200, the terminal device 300, and the analysis server 400, for example.

(Database 200)

The database 200 acquires the measurement results of the forces of the two or more different fingers of each of a plurality of users. The database 200 stores the measurement results of the forces of the two or more different fingers of each of the plurality of users.

(Terminal Device 300)

The terminal device 300 is an information processing apparatus used by the user. The terminal device 300 is, for example, a desktop personal computer (PC), a notebook PC, or a smart device such as a smartphone or a tablet.

The terminal device 300 displays the measurement results of the forces of the two or more different fingers of the user acquired from the information processing apparatus 100. In addition, the terminal device 300 displays analysis results of data related to the measurement results. Furthermore, the terminal device 300 displays a log of the measurement results of the forces of the two or more different fingers of the user. The terminal device 300 also displays training recommendation information described later.

In addition, the terminal device 300 displays statistical results related to the forces of the two or more different fingers of many users acquired from the analysis server 400. For example, the terminal device 300 displays a numerical value of a general user acquired from the analysis server 400. In addition, the terminal device 300 displays training recommendation information regarding an evaluation item the user is urged to improve from among several evaluation items based on comparison with the numerical value of the general user.

(Analysis Server 400)

The analysis server 400 acquires data on the measurement results of the forces of the two or more different fingers of each of the plurality of users from the database 200. In addition, the analysis server 400 performs statistical processing related to the forces of the two or more different fingers of each of the plurality of users based on the acquired data on the measurement results. In addition, the analysis server 400 transmits statistical results related to the forces of the two or more different fingers of each of the plurality of users to the terminal device 300.

1-2. Force Sensor

Next, a configuration of the force sensor according to the embodiment will be described with reference to FIGS. 2 to 6.

Figure 2:
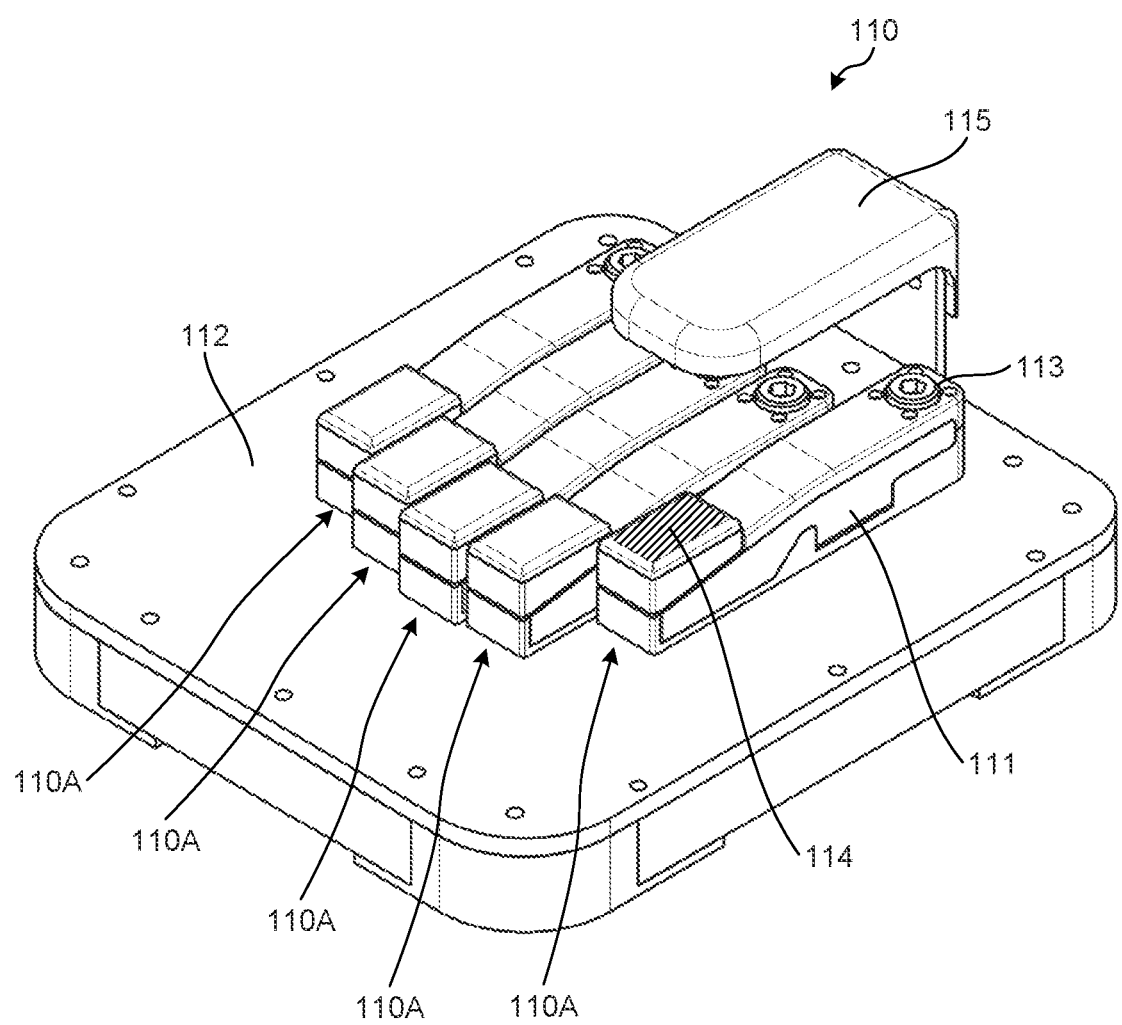
FIG. 2 is a perspective view of a force sensor according to the embodiment.

First, a description will be given with reference to FIG. 2. FIG. 2 is a perspective view of the force sensor according to the embodiment. As illustrated in FIG. 2, the force sensor 110 includes five sensor units 110A each having a built-in force sensor, a support base 112 on which the five sensor units 110A are placed, and a support portion 115 that supports the wrist of the user.

The force sensor 110 detects each of the forces of the five fingers of the user using five force sensors built in the respective sensor units 110A.

The sensor unit 110A includes a structure 111 that holds the force sensor, a fixing portion 113 that fixes the structure 111 to the support base 112, and a pressing portion 114 that indicates a place to be pressed by the finger of the user. The pressing portion 114 is provided on an upper surface of the structure 111.

The force sensor 110 includes two or more structures 111. Specifically, the force sensor 110 includes five structures 111.

In addition, the two or more structures 111 hold each of two or more force sensors. Specifically, the five structures 111 hold each of the five force sensors.

In addition, each of the two or more fixing portions 113 fixes each of the two or more structures 111 to the support base 112. Specifically, each of the five fixing portions 113 fixes each of the five structures 111 to the support base 112.

The support base 112 is provided with two or more holding mechanisms 116 that movably hold each of the two or more force sensors on the upper surface. Specifically, the support base 112 is provided with five holding mechanisms 116 (see FIG. 5) that movably hold each of the five force sensors on the upper surface.

In addition, the two or more holding mechanisms 116 fix each of the two or more force sensors to the support base 112. In addition, the five holding mechanisms 116 fix each of the five force sensors to the support base 112.

In addition, each of the two or more holding mechanisms 116 includes the fixing portion 113 that fixes each of the two or more force sensors to the support base 112. Specifically, each of the five holding mechanisms 116 includes the fixing portion 113 that fixes each of the five force sensors to the support base 112.

In addition, each of the two or more force sensors is movably held on the upper surface by the holding mechanism 116 in a state in which the fixing portion 113 is loosened. Specifically, each of the two or more force sensors is held rotatably and linearly on the upper surface by the holding mechanism 116 in the state in which the fixing portion 113 is loosened. For example, each of the five force sensors is movably held on the upper surface by the holding mechanism 116 in the state in which the fixing portion 113 is loosened. For example, each of the five force sensors is held rotatably and linearly on the upper surface by the holding mechanism 116 in the state in which the fixing portion 113 is loosened.

In addition, the support portion 115 supports at least a part of a palm of a hand including the two or more different fingers of the user. Specifically, the support portion 115 supports a region connecting each MP joint of the index finger, the middle finger, the ring finger, and the little finger in the palm and the CM joint of the thumb in the palm. With this configuration, the force sensor 110 can appropriately measure the force of the finger without hindering the movement of each finger.

Figure 3:
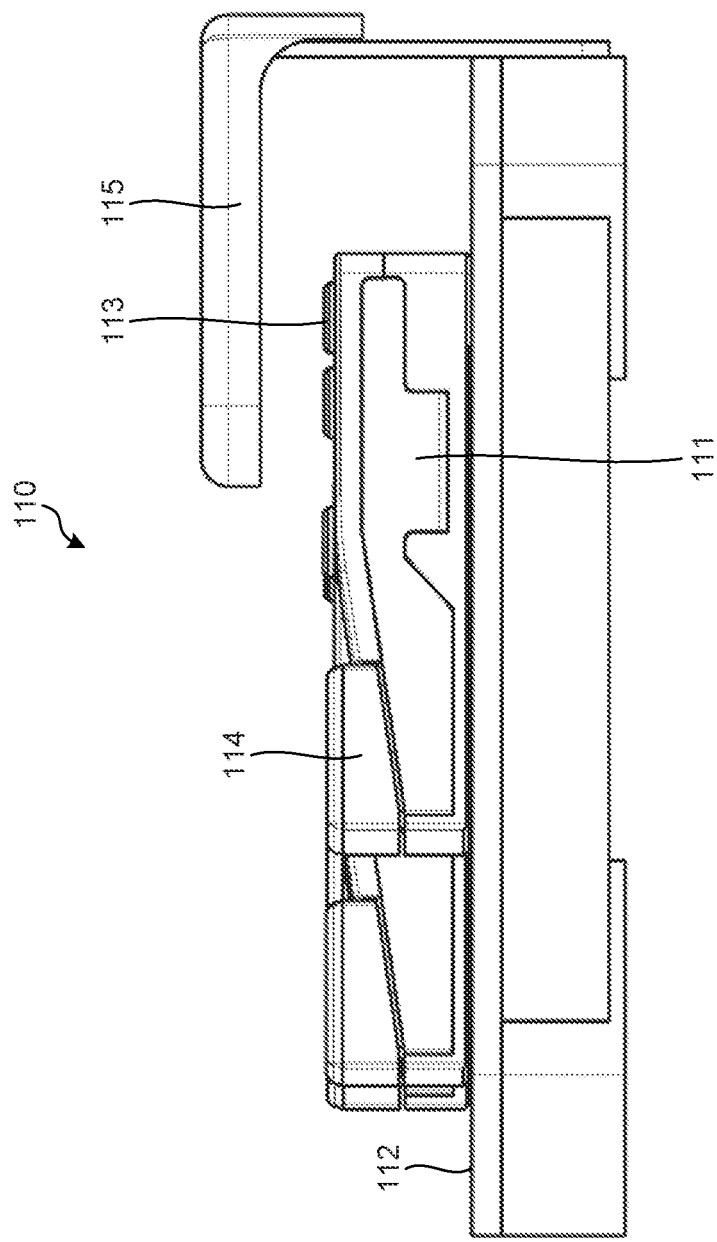
FIG. 3 is a side view of the force sensor according to the embodiment.

Next, a description will be given with reference to FIG. 3. FIG. 3 is a side view of a force sensor according to the embodiment. As illustrated in FIG. 3, all the five force sensors are installed on the horizontal support base 112. Therefore, the two or more force sensors have the same force detection direction. Specifically, the five force sensors have force detection directions aligned in a direction horizontal to the upper surface of the support base 112.

Figure 4:
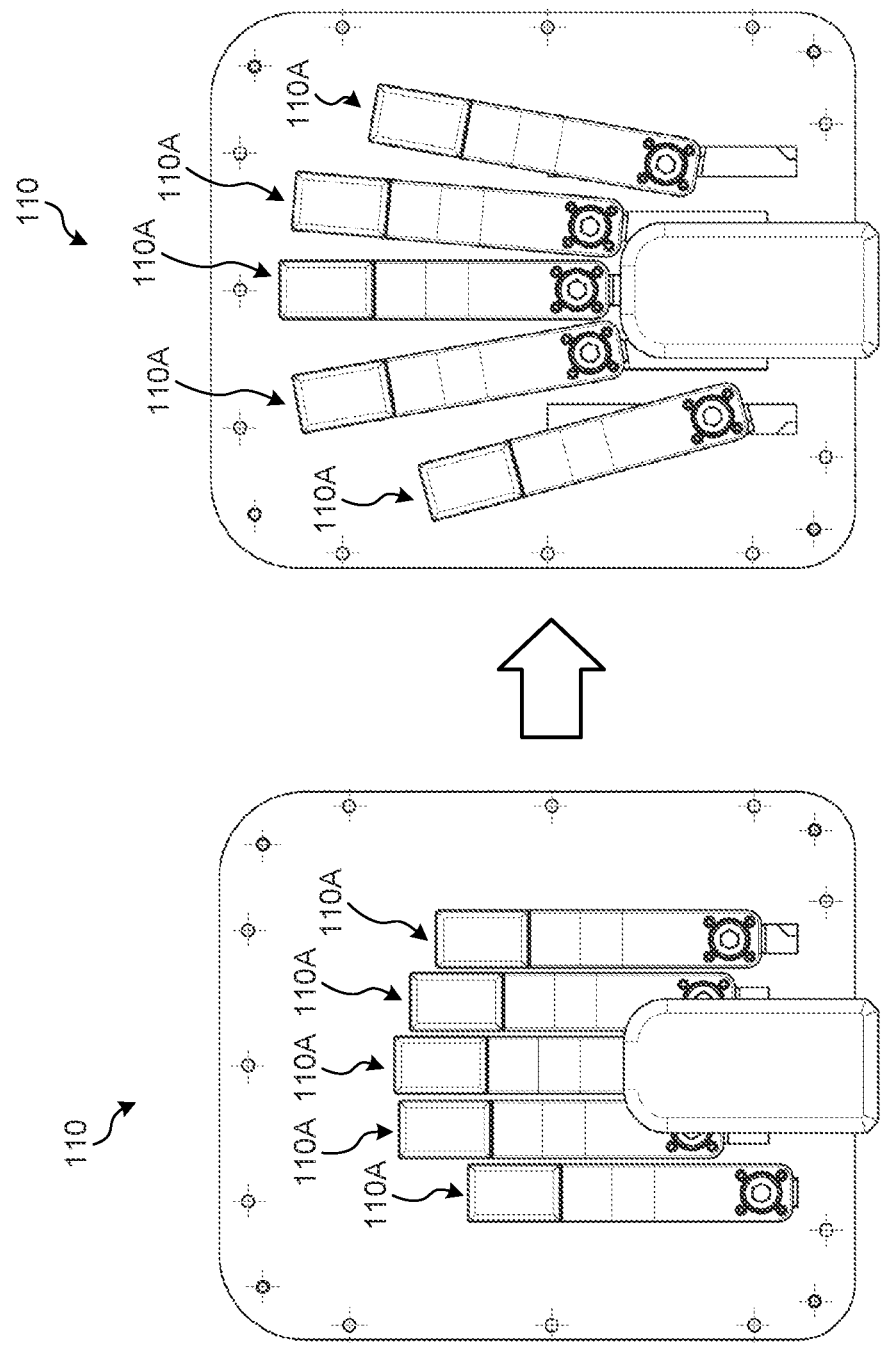
FIG. 4 is a top view of the force sensor according to the embodiment.

Next, a description will be given with reference to FIG. 4. FIG. 4 is a top view of a force sensor according to the embodiment. The left side of FIG. 4 is a top view of FIG. 2. The right side of FIG. 4 illustrates a state in which the five sensor units 110A are moved on the upper surface along the holding mechanism 116 in the state in which the fixing portion is loosened. Thus, the force sensor 110 can freely adjust the position and angle of the force sensor. That is, the force sensor 110 can accommodate various hand sizes and shapes of the user. That is, the force sensor 110 can fix the force sensor at a measurement position optimum for each user. Therefore, since the force sensor 110 can measure the force of each finger in a state in which each user maintains the correct posture of the hand, the reliability of sensing can be improved.

Figure 5:
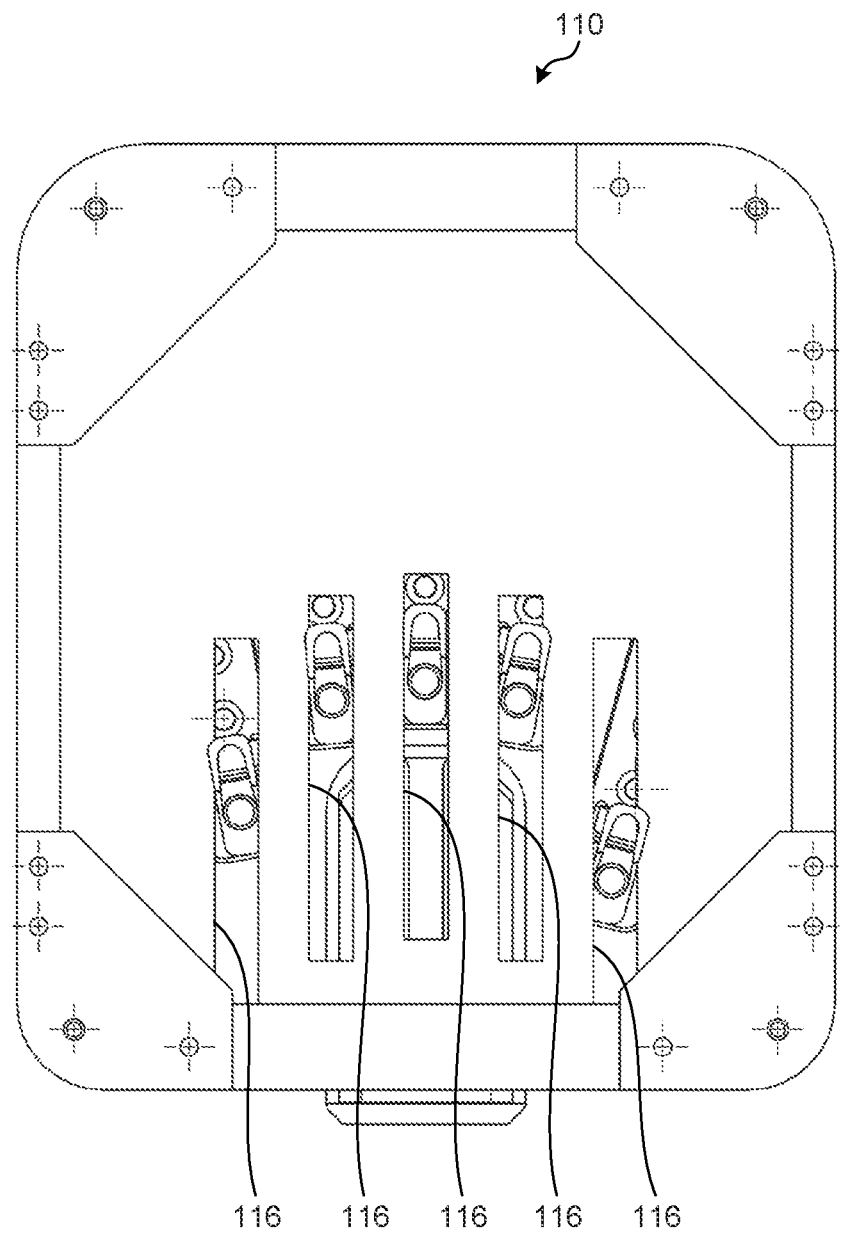
FIG. 5 is a view for demonstrating a holding mechanism provided on a support base according to the embodiment, and is a view of the support base as viewed from below.

Next, a description will be given with reference to FIG. 5. FIG. 5 is a view for demonstrating the holding mechanism provided on the support base according to the embodiment, and is a view of the support base as viewed from below. As illustrated in FIG. 5, when the support base 112 is viewed from below, the support base 112 is provided with the five holding mechanisms 116. In addition, the holding mechanism 116 movably holds each of the two or more force sensors on the upper surface along two or more rectangular grooves provided on the support base 112. Specifically, the five holding mechanisms 116 movably hold each of the five force sensors on the upper surface along the five rectangular grooves provided on the support base 112. The two or more rectangular grooves may be radially arranged such that one ends of the two or more rectangular grooves are closer to each other than the other ends. Specifically, the five rectangular grooves may be radially arranged such that one ends of the five rectangular grooves are closer to each other than the other ends. The holding mechanism 116 may be any mechanism as long as it can movably hold the force sensor on the upper surface. More specifically, the holding mechanism 116 may be any mechanism as long as it includes a rotation mechanism that rotatably holds the force sensor on the upper surface of the support base 112 and a linear motion mechanism that linearly holds the force sensor on the upper surface of the support base 112. For example, the holding mechanism 116 may be a groove having a rounded square shape with rounded corners. The holding mechanism 116 may have a curved shape (rail shape). The holding mechanism 116 may be a rail provided on the support base 112.

Figure 6:
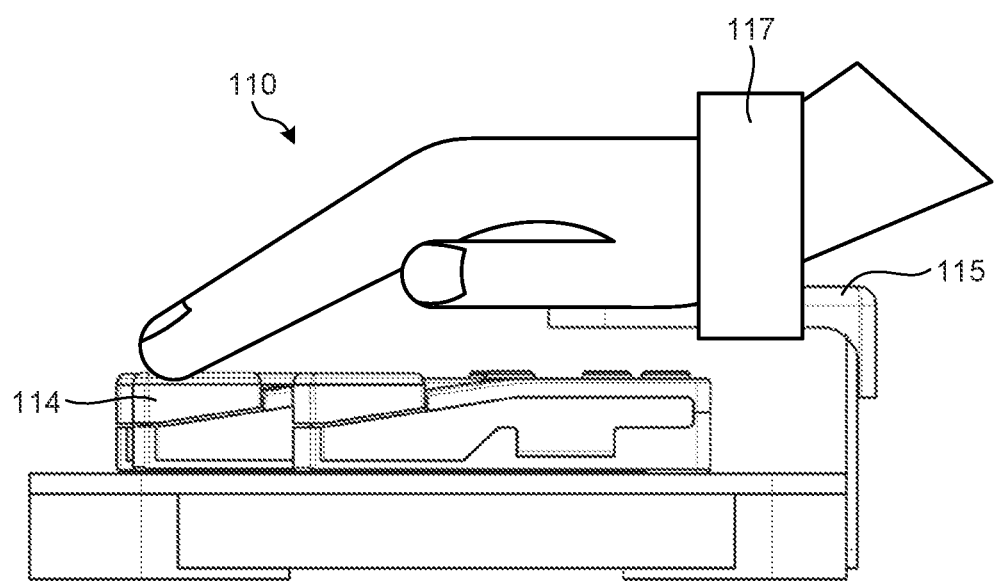
FIG. 6 is a diagram for demonstrating a support portion of the force sensor according to the embodiment.

Next, a description will be given with reference to FIG. 6. FIG. 6 is a diagram for demonstrating the support portion of the force sensor according to the embodiment. As illustrated in FIG. 6, the wrist is fixed to the support portion 115 of the force sensor by a band 117. The band 117 is realized by, for example, a soft material such as a Velcro (registered trademark) band, a rubber band, and cloth. The band 117 may be a hard fixture. For example, the band 117 is realized by pressing down a rigid fixture with a spring moving up and down. With this configuration, the force sensor 110 can suppress the movement of the wrist using the band 117. In addition, the force sensor 110 can indirectly suppress the movement of the arm by suppressing the movement of the wrist using the band 117. Thus, the force sensor 110 can transmit merely the force of the fingers to the force sensor 110 side by absorbing the forces of the wrist and the arm on the support portion 115 side. Therefore, the force sensor 110 can more accurately detect the force of the finger.

1-3. Measurement of Force of a Finger

Figure 7:
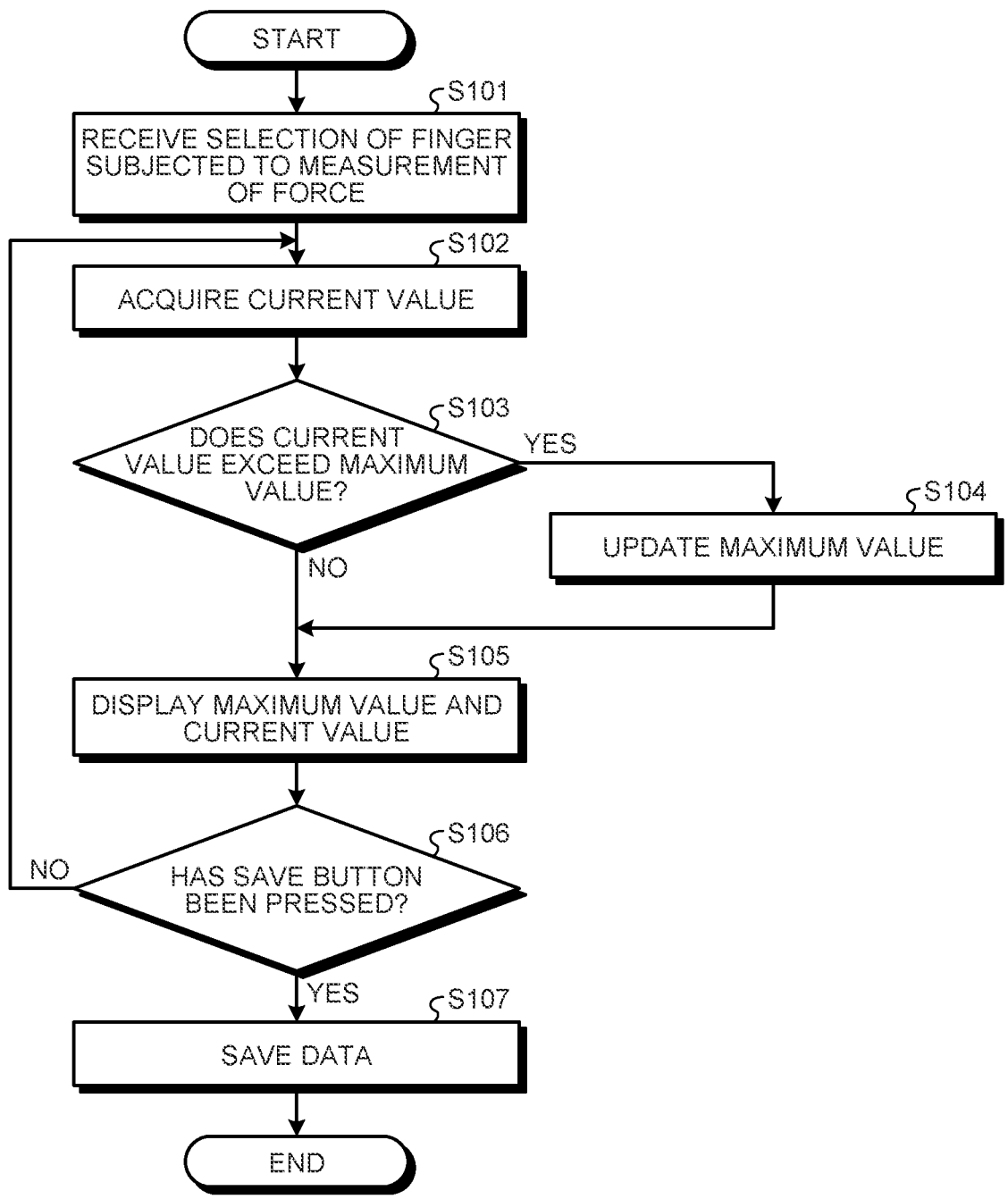
FIG. 7 is a flowchart illustrating a processing procedure of measurement of the force of a finger according to the embodiment.

Next, the measurement of the force of the finger according to the embodiment will be described with reference to FIGS. 7 to 10. First, a description will be given with reference to FIG. 7. FIG. 7 is a flowchart illustrating a processing procedure of the measurement of the force of the finger according to the embodiment.

As illustrated in FIG. 7, the processing unit 122 receives selection of a finger subjected to the measurement of the force (Step S101). Subsequently, after receiving the selection of the finger, the processing unit 122 starts the measurement of the force. The processing unit 122 acquires the current value of the force of the finger (Step S102).

After acquiring the current value of the force of the finger, the processing unit 122 determines whether or not the current value of the force of the finger exceeds the maximum value of the force of the finger measured up to the present time (Step S103). When it is determined that the current value of the force of the finger does not exceed the maximum value (Step S103; No), the processing unit 122 displays the current value and the maximum value of the measured force of the finger on the display unit 130 (Step S105).

On the other hand, when it is determined that the current value of the force of the finger exceeds the maximum value (Step S103; Yes), the processing unit 122 updates the maximum value of the force of the finger (Step S104). After updating the maximum value of the force of the finger, the processing unit 122 displays the maximum value and the current value (the same value as the maximum value) of the force of the finger on the display unit 130 (Step S105).

Subsequently, after displaying the current value and the maximum value of the force of the finger, the processing unit 122 determines whether or not the save button has been pressed (Step S106). When it is determined that the save button has been pressed (Step S106: Yes), the processing unit 122 saves the measured data in the storage unit 140 (Step S107).

On the other hand, when it is determined that the save button has not been pressed (Step S106: No), the processing unit 122 returns to Step S102.

Figure 8:
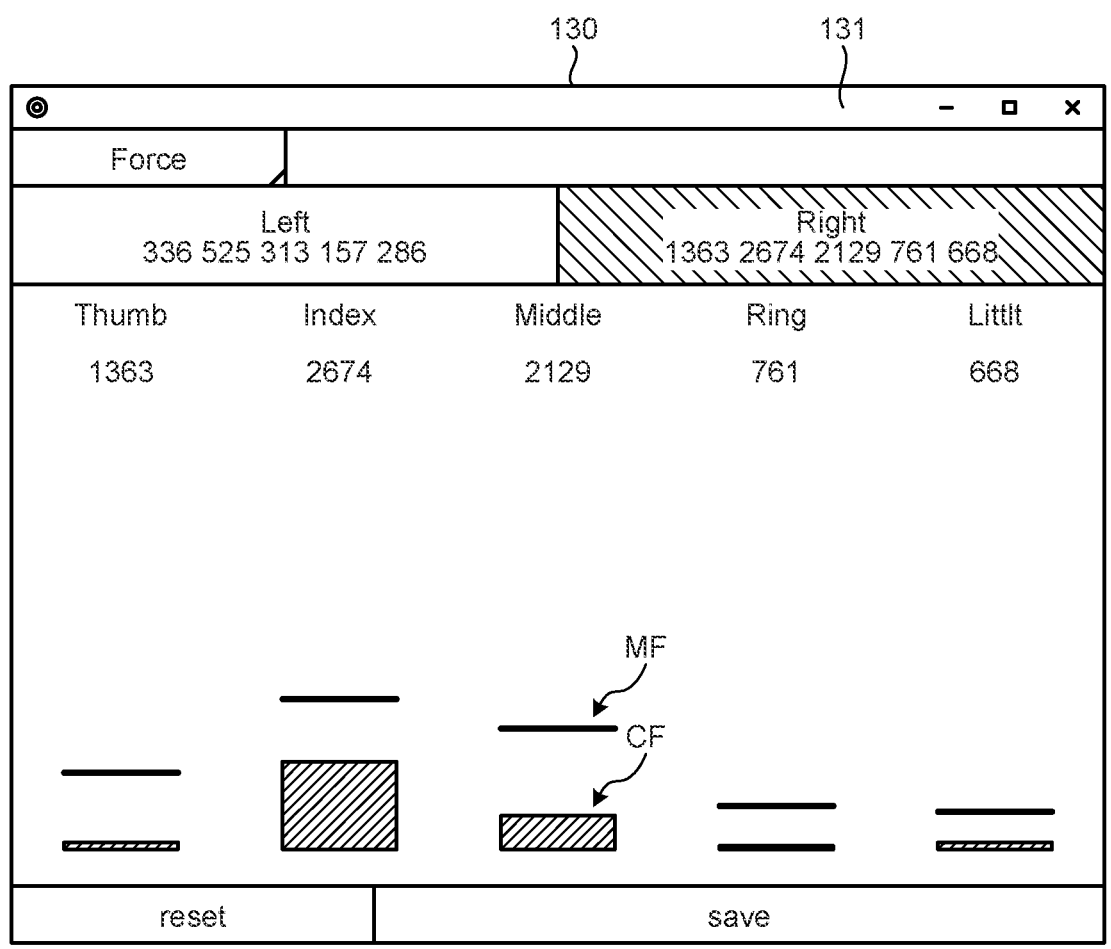
FIG. 8 is a view illustrating an example of a display screen during the measurement of the force of the finger according to the embodiment.

Next, a description will be given with reference to FIG. 8. FIG. 8 is a view illustrating an example of a display screen during the measurement of the force of the finger according to the embodiment. In FIG. 8, the display unit 130 displays a display screen 131 during the measurement of each of the force of the thumb, the force of the index finger, the force of the middle finger, the force of the ring finger, and the force of the little finger of the right hand.

The display unit 130 displays a currently measured value of the force of each finger (hereinafter, also referred to as a current value) and a maximum value of the force of the finger up to the measurement point (hereinafter, also referred to as a maximum value). For example, when the middle finger is taken as an example, the display unit 130 displays a current value CF and a maximum value MF of the force of the middle finger.

Figure 9:
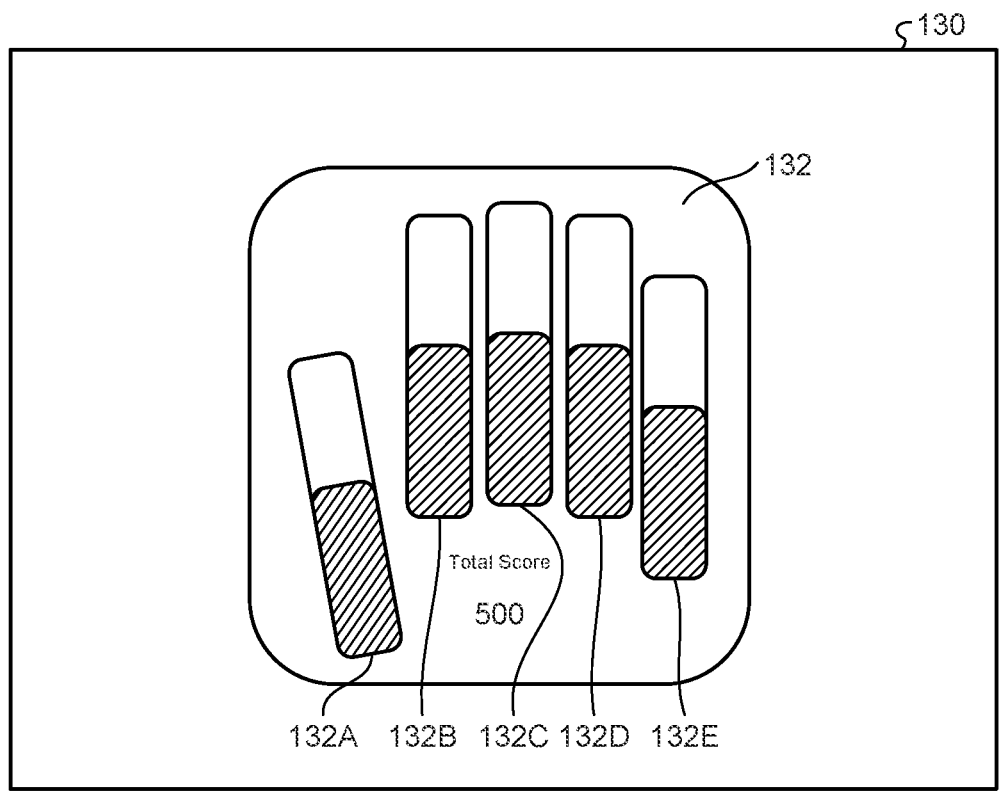
FIG. 9 is a view illustrating an example of a display screen of measurement results of the force of the finger according to the embodiment.

Next, a description will be given with reference to FIG. 9. FIG. 9 is a view illustrating an example of a display screen of measurement results of the force of the finger according to the embodiment. In FIG. 9, the display unit 130 displays an image 132 that is an image illustrating the measurement results of the force of the finger and imitates the shape of the force sensor 110. The image 132 includes an image 132A indicating the measurement results of the force of the thumb of the right hand, an image 132B indicating the measurement results of the force of the index finger, an image 132C indicating the measurement results of the force of the middle finger, an image 132D indicating the measurement results of the force of the ring finger, and an image 132E indicating the measurement results of the force of the little finger.

Figure 10:
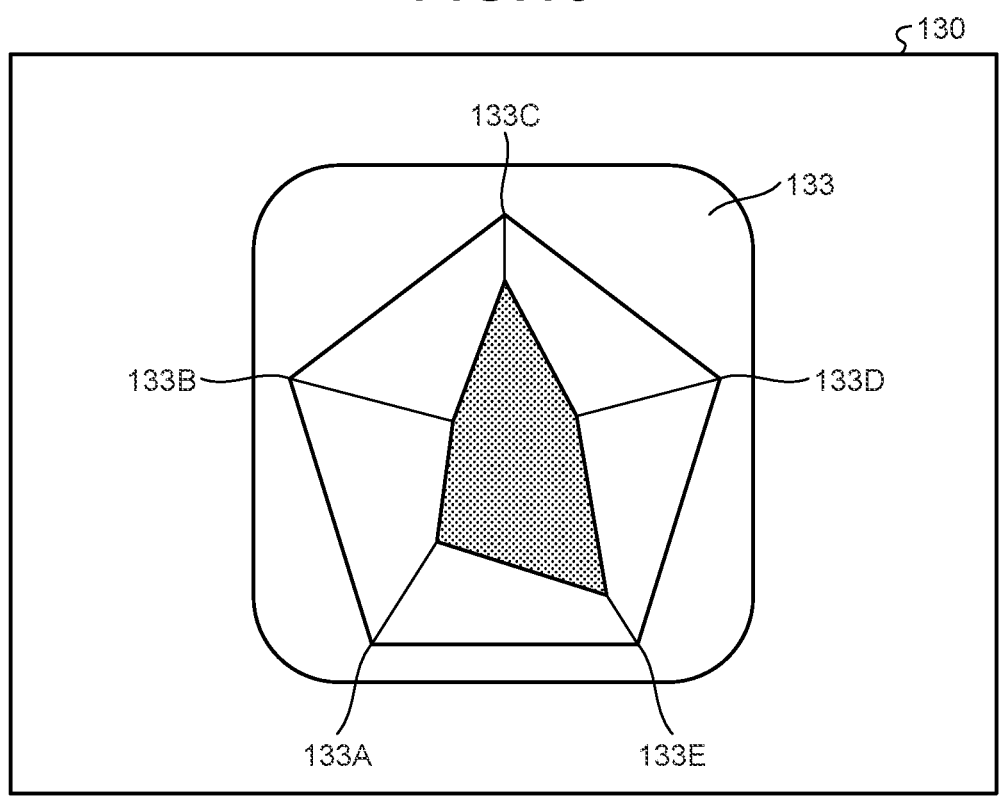
FIG. 10 is a view illustrating an example of the display screen of the measurement results of the force of the finger according to the embodiment.

Next, a description will be given with reference to FIG. 10. FIG. 10 is a view illustrating an example of the display screen of the measurement results of the force of the finger according to the embodiment. In FIG. 10, the display unit 130 displays an image 133 of a radar chart that is an image indicating the measurement results of the force of the finger. Each vertex of the image 133 corresponds to a respective finger. In FIG. 10, a vertex 133A of the radar chart corresponds to the thumb of the right hand. A vertex 133B corresponds to the index finger of the right hand. A vertex 133C corresponds to the middle finger of the right hand. A vertex 133D corresponds to the ring finger of the right hand. A vertex 133E corresponds to the little finger of the right hand.

1-4. Measurement of Independence of a Finger

Figure 11:
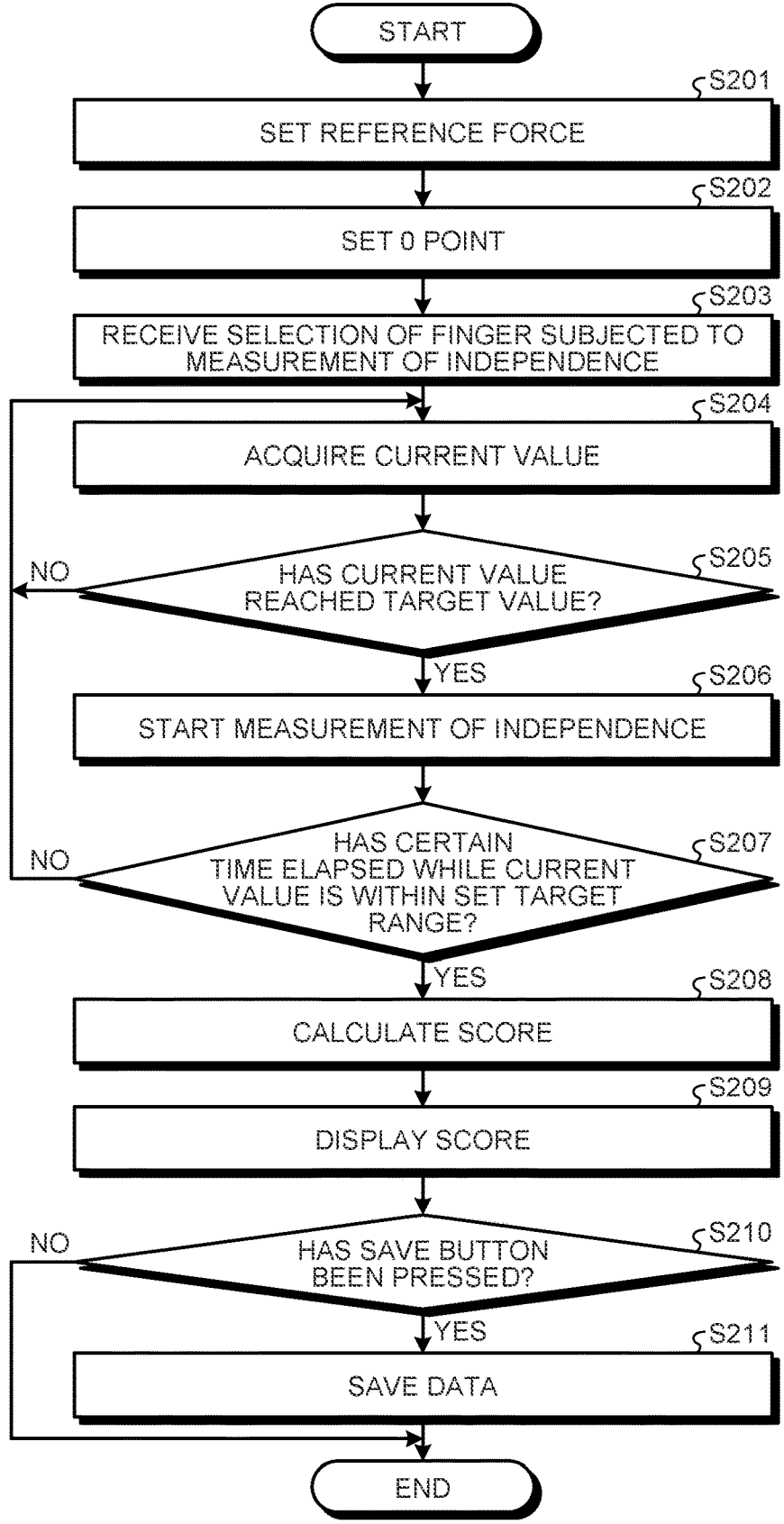
FIG. 11 is a flowchart illustrating a processing procedure of measurement of the independence of the finger according to the embodiment.

Next, measurement of the independence of the finger according to the embodiment will be described with reference to FIGS. 11 to 15. First, a description will be given with reference to FIG. 11. FIG. 11 is a flowchart illustrating a processing procedure of the measurement of the independence of the finger according to the embodiment.

As illustrated in FIG. 11, the processing unit 122 sets a reference force of each finger (Step S201). For example, the processing unit 122 sets a value corresponding to a predetermined ratio (for example, 50%) of the maximum value of the force of each finger measured in FIG. 7 as the reference force of each finger.

Subsequently, the processing unit 122 sets a 0 point (Step S202). For example, the processing unit 122 sets as the 0 point the force of each finger measured when the palm of the hand is placed on the support portion 115 while the user consciously relaxes each finger.

Subsequently, the processing unit 122 receives selection of a finger subjected to the measurement of the independence (Step S203). After receiving the selection of the finger, the processing unit 122 starts measurement of the force of the selected finger. After starting the measurement of the force of the selected finger, the processing unit 122 acquires the current value of the force of the selected finger (Step S204).

Subsequently, after acquiring the current value of the force of the finger, the processing unit 122 determines whether or not the current value has reached a target value (Step S205). When it is determined that the current value has not reached the target value (Step S205; No), the processing unit 122 returns to Step S204 again.

On the other hand, when it is determined that the current value has reached the target value (Step S205; Yes), the processing unit 122 starts the measurement of the independence of the selected finger (Step S206). Specifically, the processing unit 122 starts the measurement of the force of each finger. After starting the measurement of the force of each finger, the processing unit 122 acquires the current value of the force of each finger.

Subsequently, the processing unit 122 determines whether or not a certain period of time has elapsed in a state in which the force of each finger is within a set target range of the force of each finger (Step S207). When it is determined that the certain period of time has not elapsed in the state in which the force of each finger is within the set target range of the force of each finger (Step S207; No), the processing unit 122 returns to the Step S204 again.

On the other hand, when it is determined that the certain period of time has elapsed in the state in which the force of each finger is within the set target range of the force of each finger (Step S207; Yes), the processing unit 122 calculates a score indicating the independence of the selected finger (Step S208).

Subsequently, after calculating the score, the processing unit 122 displays the calculated score on the display unit 130 (Step S209).

Subsequently, the processing unit 122 determines whether or not the save button has been pressed (Step S210). When it is determined that the save button has been pressed (Step S210: Yes), the processing unit 122 saves the measured data in the storage unit 140 (Step S211).

On the other hand, when it is determined that the save button has not been pressed (Step S210: No), the processing unit 122 ends the processing.

Figure 12:
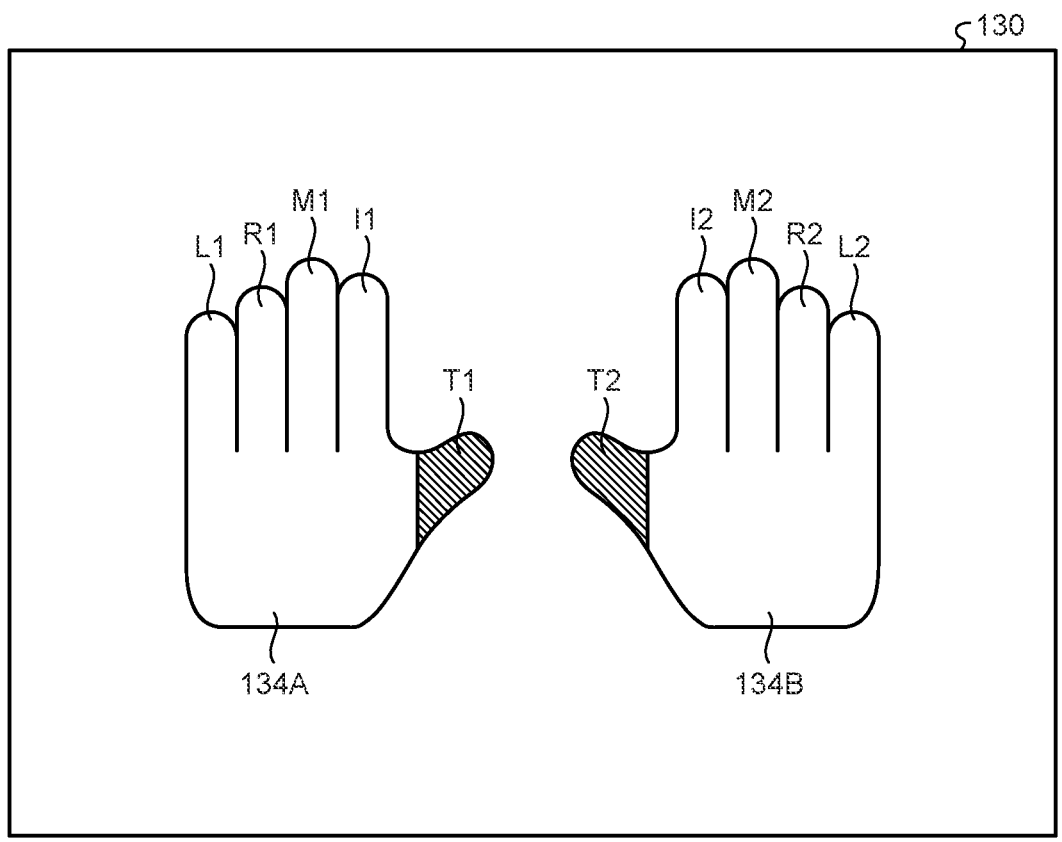
FIG. 12 is a view illustrating an example of a selection screen of the finger subjected to the measurement of the independence according to the embodiment.

Next, a description will be given with reference to FIG. 12. FIG. 12 is a view illustrating an example of a selection screen of the finger subjected to the measurement of the independence according to the embodiment. In FIG. 12, the display unit 130 displays an icon image 134A of the finger of the left hand and an icon image 134B of the finger of the right hand. For example, a portion indicated by T1 in the icon image 134A corresponds to the thumb of the left hand. Similarly, portions indicated by I1, M1, R1, and L1 in the icon image 134A correspond to the index finger of the left hand, the middle finger of the left hand, the ring finger of the left hand, and the little finger of the left hand, respectively. For example, a portion indicated by T2 in the icon image 134B corresponds to the thumb of the right hand. Similarly, portions indicated by I2, M2, R2, and L2 in the icon image 134B correspond to the index finger of the right hand, the middle finger of the right hand, the ring finger of the right hand, and the little finger of the right hand, respectively. In addition, for example, the display unit 130 displays an image in which a finger selected by the user is colored. In FIG. 12, the display unit 130 displays an image in which the thumb T1 of the left hand and the thumb T2 of the right hand that are selected by the user is colored.

Figure 13:
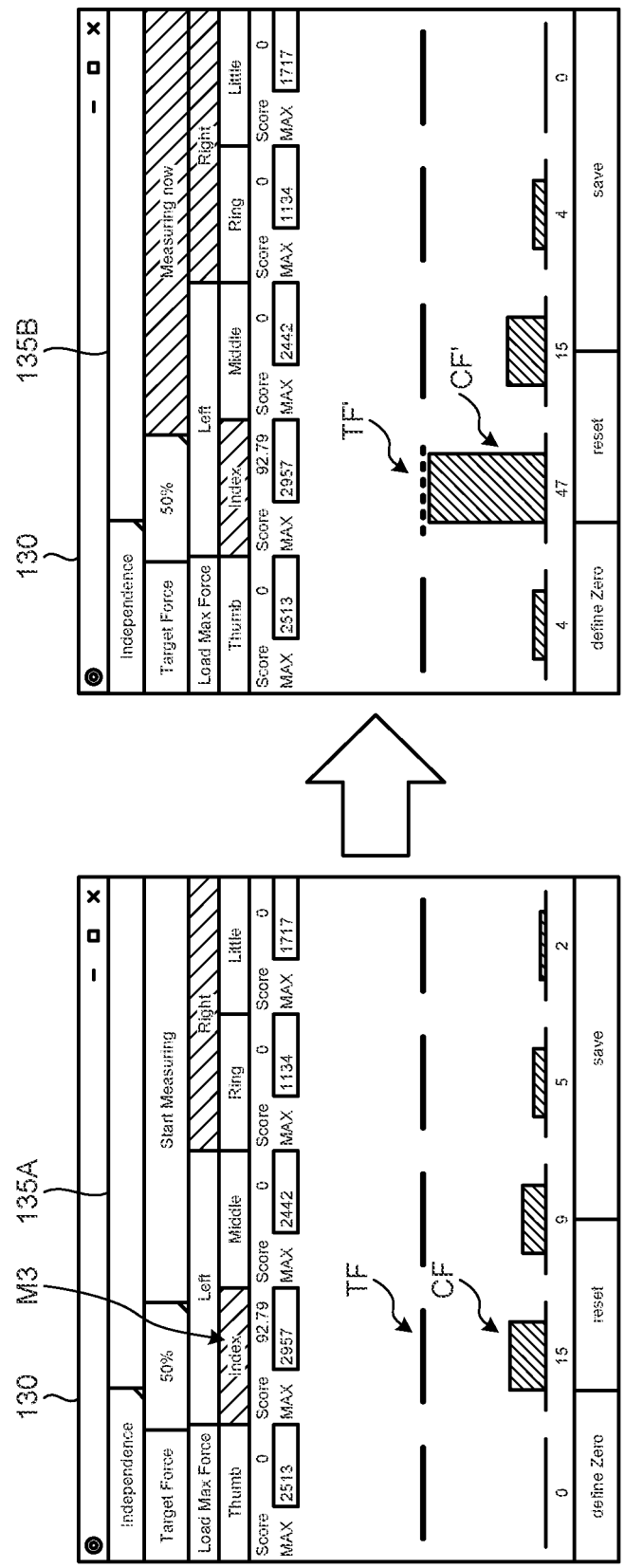
FIG. 13 is a view illustrating an example of a display screen during the measurement of the independence of the finger according to the embodiment.

Next, a description will be given with reference to FIG. 13. FIG. 13 is a view illustrating an example of a display screen during the measurement of the independence of the finger according to the embodiment. The processing unit 122 receives selection of the finger subjected to the measurement of the independence from the user. In FIG. 13, the processing unit 122 receives the selection of the index finger of the right hand as the finger subjected to the measurement of the independence from the user. The processing unit 122 may receive selection of a plurality of fingers subjected to the measurement of the independence from the user.

In addition, the display unit 130 displays information related to a preset target value related to the force of the finger of the user. In FIG. 13, the display unit 130 displays a bar TF indicating the preset target value of the force of the index finger of the right hand of the user.

In the measurement of the independence of the finger, the user tenses the finger subjected to the measurement of independence to aim for the target value, while placing five fingers on the force sensor 110. The display unit 130 displays a bar graph CF indicating the current value of the force of the index finger during the measurement. The display unit 130 indicates the ratio of the current value to the maximum value of the force of each finger.

As illustrated on the right side of FIG. 13, when the height of the bar graph CF' indicating the current value of the force of the index finger during the measurement is within the range of the target value of the force of the index finger, the display unit 130 displays a bar TF' indicating the target value with high visibility. For example, the display unit 130 changes the color, pattern, color density, shape, or the like of the bar TF' indicating the target value, thereby displaying the bar with high visibility.

The processing unit 122 calculates the independence of the finger subjected to the measurement by normalizing the forces of the four fingers other than the finger subjected to the measurement of the independence with the maximum values of the forces of the respective fingers, and then taking an average. The processing unit 122 may calculate the relation between the forces of each finger for each measured value instead of taking the average. The display unit 130 displays information indicating a ratio of the force of another finger to the force of a predetermined finger among the two or more different fingers measured by the processing unit 122.

Figure 14:
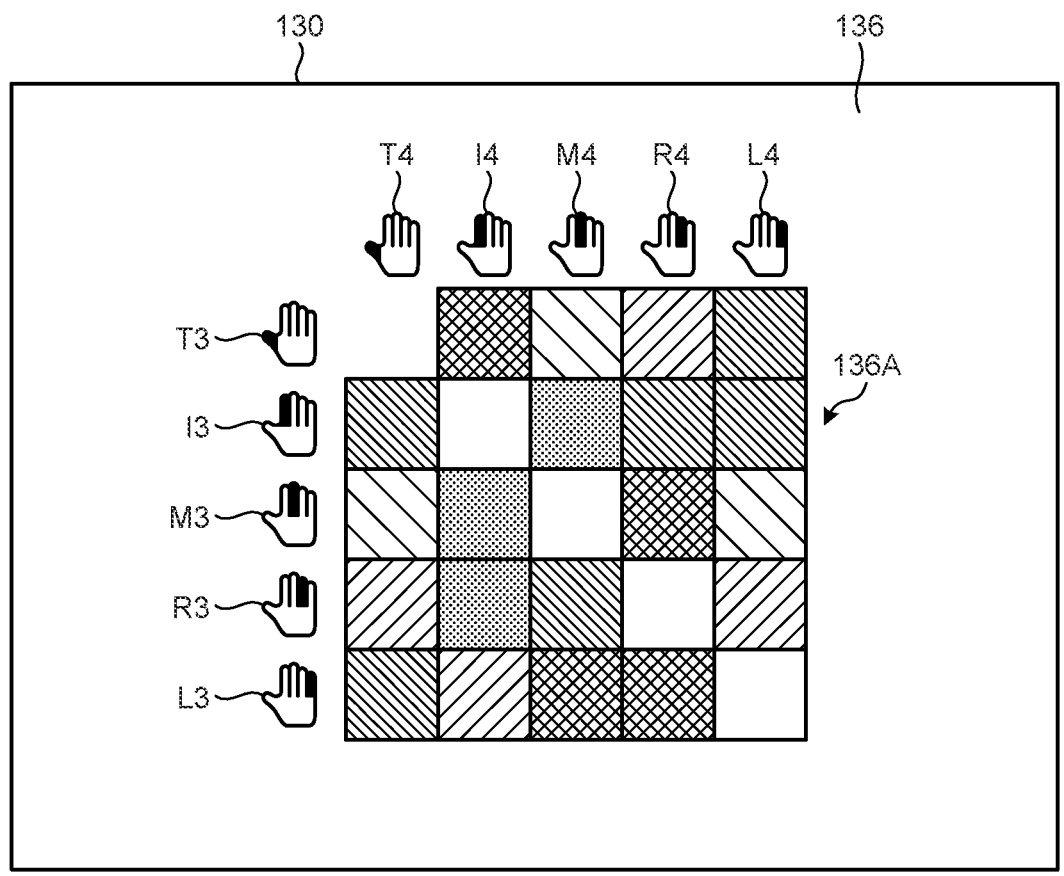
FIG. 14 is a view illustrating an example of the display screen of measurement results of the independence of the finger according to the embodiment.

Next, a description will be given with reference to FIG. 14. FIG. 14 is a view illustrating an example of a display screen of measurement results of the independence of the finger according to the embodiment. As illustrated in FIG. 14, the display unit 130 displays an image 136A of a color matrix that is an image indicating the measurement results of the independence and indicating the relation between the forces of the respective fingers. For example, the display unit 130 displays the ratio of the force of another finger to the force of a finger using the color or shade of each matrix. For example, the display unit 130 expresses the color of the corresponding matrix in red as the ratio of the force of another finger to the force of a finger is larger, and expresses the color of the corresponding matrix in green (complementary color of red) as the ratio of the force of another finger to the force of a finger is smaller. Alternatively, the display unit 130 expresses the corresponding matrix in a darker color as the ratio of the force of another finger to the force of a finger is larger, and expresses the corresponding matrix in a lighter color as the ratio of the force of another finger to the force of a finger is smaller. In addition, the display unit 130 displays a matrix indicating a relation between the same fingers (for example, the thumbs of the right hand and the like) in the color matrices in a white color or in blank.

Figure 15:
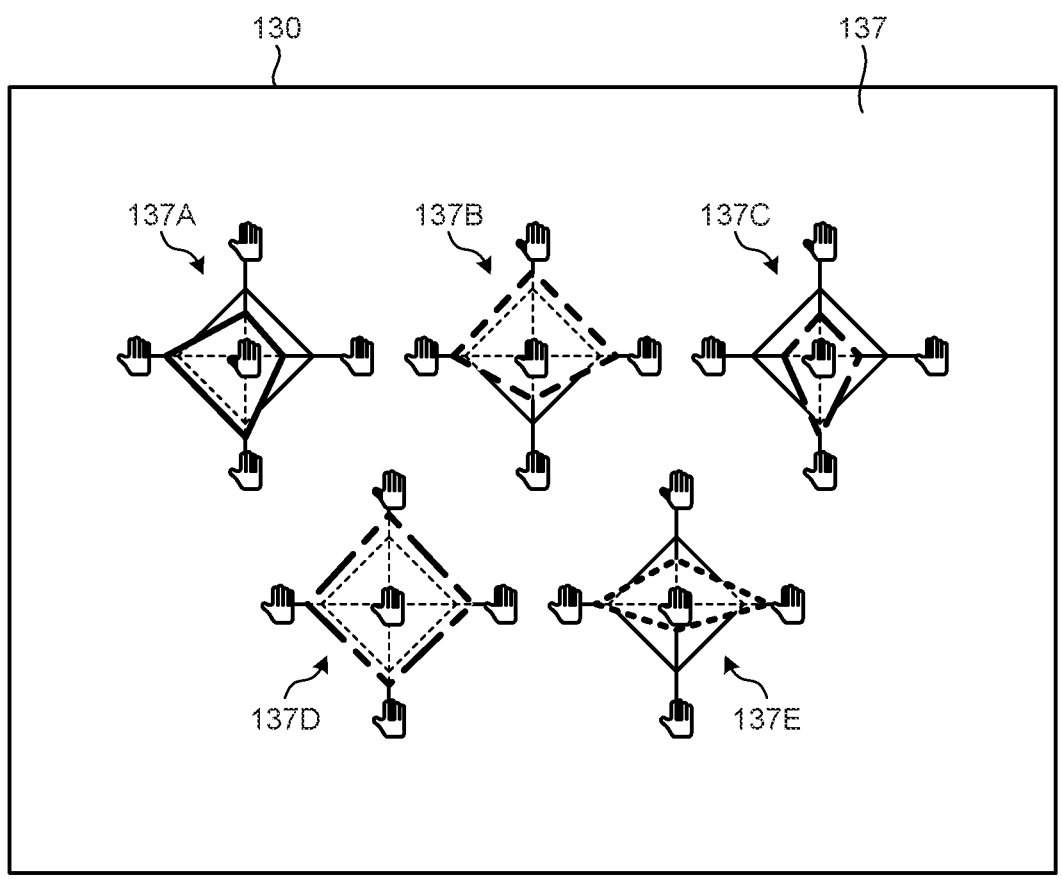
FIG. 15 is a view illustrating an example of the display screen of the measurement results of the independence of the finger according to the embodiment.

Next, a description will be given with reference to FIG. 15. FIG. 15 is a view illustrating an example of the display screen of the measurement results of the independence of the finger according to the embodiment. As illustrated in FIG. 15, the display unit 130 may display an image of a radar chart indicating the measurement results of the independence of each finger. For example, the display unit 130 displays an image 137A of a radar chart indicating the ratios of the forces of the other fingers to the thumb of the right hand. In addition, the display unit 130 displays an image 137B of a radar chart indicating the ratios of the forces of the other fingers to the index finger of the right hand. In addition, the display unit 130 displays an image 137C of a radar chart indicating the ratios of the forces of the other fingers to the middle finger of the right hand. In addition, the display unit 130 displays an image 137D of a radar chart indicating the ratios of the forces of the other fingers to the ring finger of the right hand. In addition, the display unit 130 displays an image 137E of a radar chart indicating the ratios of the forces of the other fingers to the little finger of the right hand.

1-5. Measurement of Agility of a Finger

Figure 16:
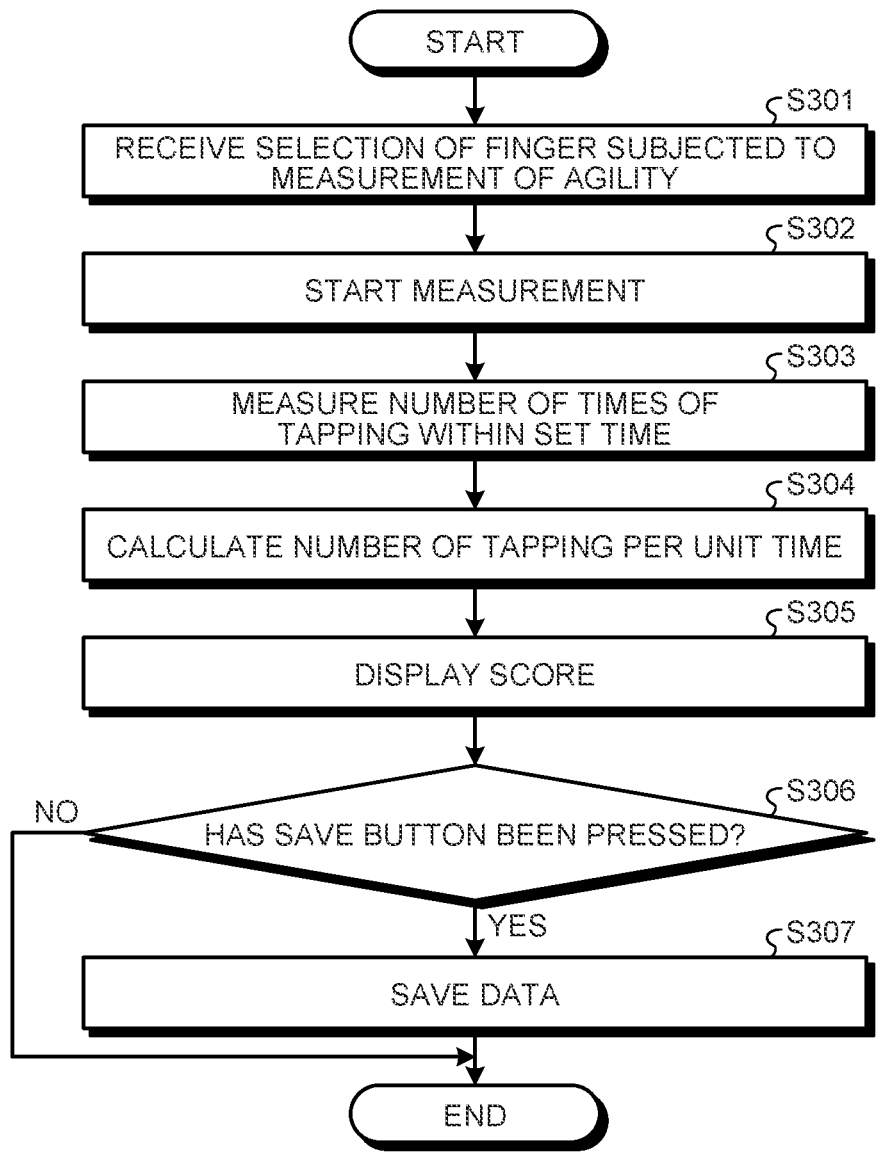
FIG. 16 is a flowchart illustrating a processing procedure of measurement of the agility of the finger according to the embodiment.
Figure 17:
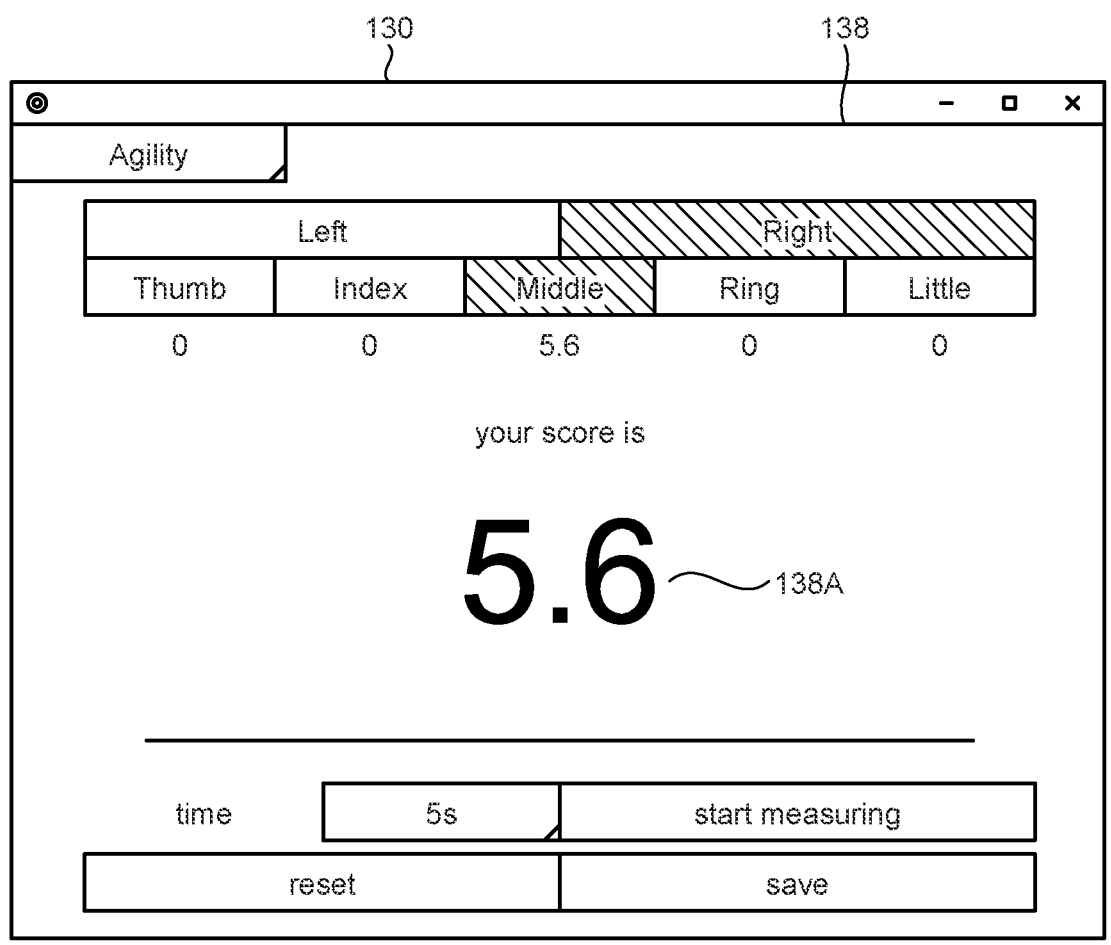
FIG. 17 is a view illustrating an example of a display screen during the measurement of the agility of the finger according to the embodiment.
Figure 18:
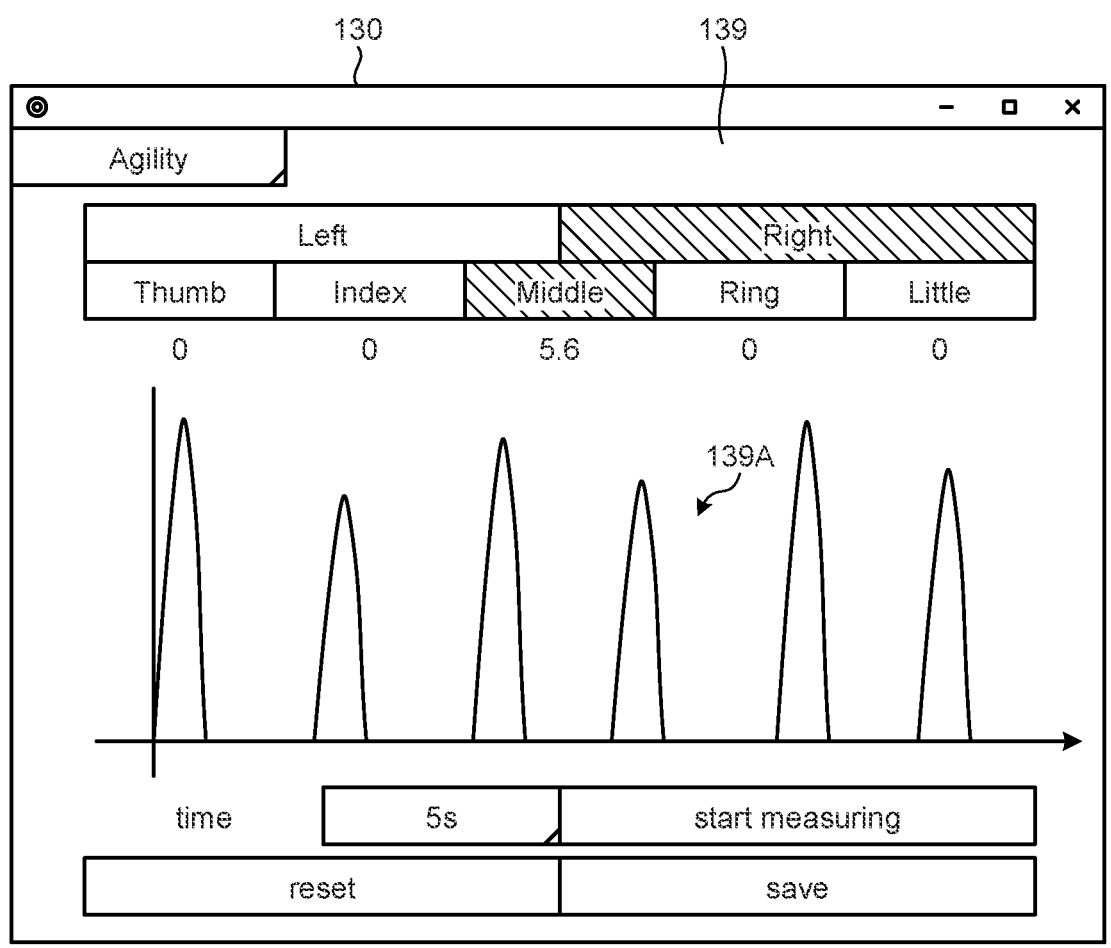
FIG. 18 is a view illustrating an example of the display screen of measurement results of the agility of the finger according to the embodiment.

Next, measurement of the agility of the finger according to the embodiment will be described with reference to FIGS. 16 to 18. First, a description will be given with reference to FIG. 16. FIG. 16 is a flowchart illustrating a processing procedure of the measurement of the agility of the finger according to the embodiment.

The processing unit 122 receives selection of a finger subjected to the measurement of the agility from the user (Step S301). After receiving the selection of the finger, the processing unit 122 starts the measurement of the agility of the selected finger (Step S302). After starting the measurement of the agility of the selected finger, the processing unit 122 measures the number of times of tapping of the selected finger within a set time (Step S303).

After completing the measurement, the processing unit 122 calculates the number of times of tapping per unit time (Step S304). After calculating the number of times of tapping per unit time, the processing unit 122 displays the number of times of tapping per unit time on the display unit 130 as a score indicating the agility (Step S305).

Subsequently, the processing unit 122 determines whether or not the save button has been pressed (Step S306). When it is determined that the save button has been pressed (Step S306: Yes), the processing unit 122 saves the measured data in the storage unit 140 (Step S307).

On the other hand, when it is determined that the save button has not been pressed (Step S307: No), the processing unit 122 ends the processing.

Next, a description will be given with reference to FIG. 17. FIG. 17 is a view illustrating an example of a display screen during the measurement of the agility of the finger according to the embodiment. In FIG. 17, the display unit 130 displays the number 138A indicating the number of times of tapping per unit time.

Next, a description will be given with reference to FIG. 18. FIG. 18 is a view illustrating an example of the display screen of the measurement results of the agility of the finger according to the embodiment. In FIG. 18, the display unit 130 displays a time-series graph 139A indicating the tapping force at each tapping timing.

1-6. Measurement of Repetitive Reproducibility of Tapping Force of a Finger

Figure 19:
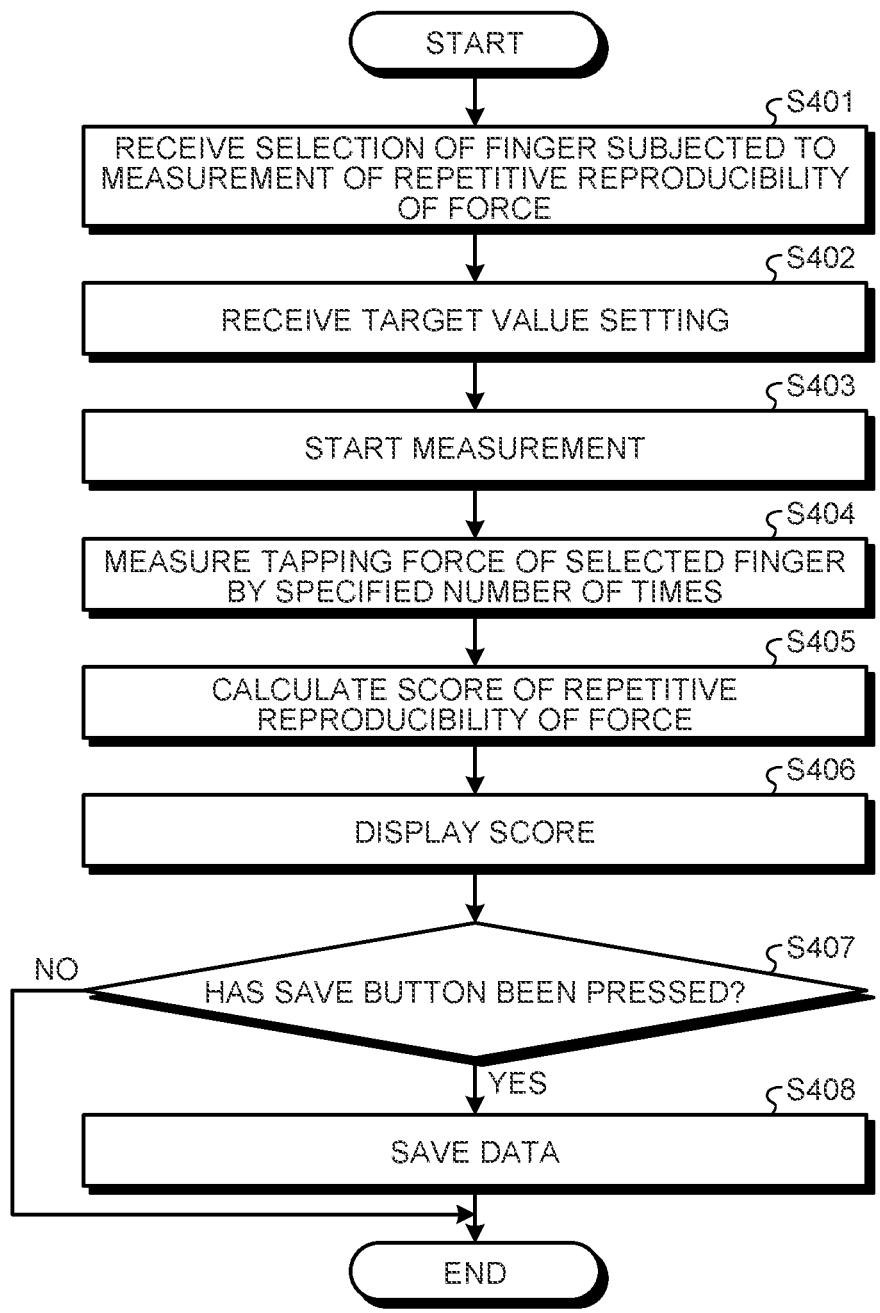
FIG. 19 is a flowchart illustrating a processing procedure of measurement of the repetitive reproducibility of the tapping force of the finger according to the embodiment.
Figure 20:
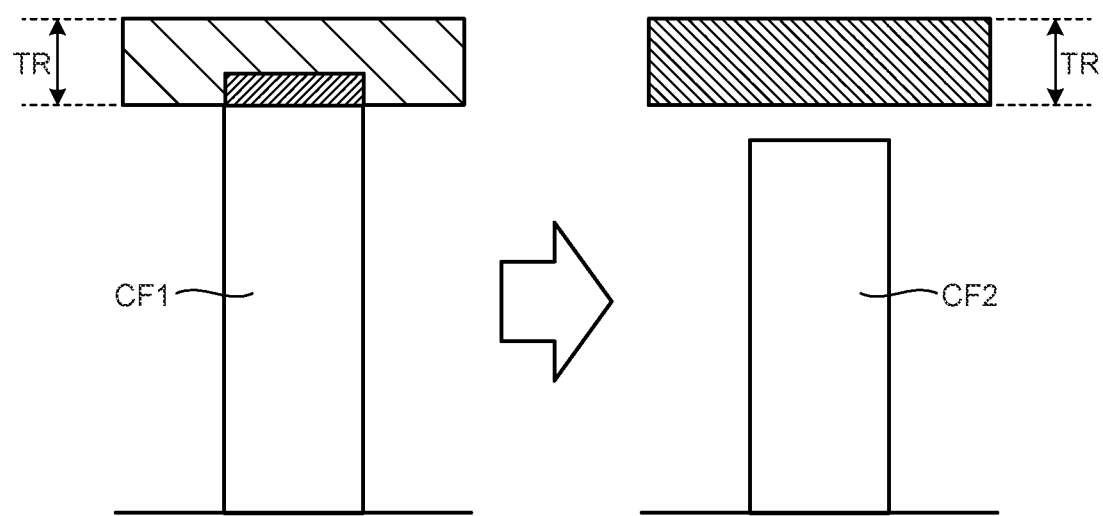
FIG. 20 is a view illustrating an example of a display screen during the measurement of the repetitive reproducibility of the tapping force of the finger according to the embodiment.

Next, measurement of the repetitive reproducibility of the tapping force of the finger according to the embodiment will be described with reference to FIGS. 19 to 20. First, a description will be given with reference to FIG. 19. FIG. 19 is a flowchart illustrating a processing procedure of the measurement of the repetitive reproducibility of the tapping force of the finger according to the embodiment.

The processing unit 122 receives selection of a finger subjected to the measurement of the repetitive reproducibility of the tapping force (Step S401). Subsequently, after receiving the selection of the finger, the processing unit 122 receives the setting of a target value (Step S402). Then, after receiving the setting of the target value, the processing unit 122 starts the measurement of the repetitive reproducibility of the tapping force of the selected finger (Step S403).

Subsequently, after starting the measurement, the processing unit 122 measures the tapping force of the selected finger by a specified number of times (Step S404). After completing the measurement, the processing unit 122 calculates a score indicating the repetitive reproducibility of the tapping force (Step S405).

Subsequently, after calculating the score, the processing unit 122 displays the calculated score on the display unit 130 (Step S406).

Subsequently, the processing unit 122 determines whether or not the save button has been pressed (Step S407). When it is determined that the save button has been pressed (Step S407: Yes), the processing unit 122 saves the measured data in the storage unit 140 (Step S408).

On the other hand, when it is determined that the save button has not been pressed (Step S407: No), the processing unit 122 ends the processing.

Next, a description will be given with reference to FIG. 20. FIG. 20 is a view illustrating an example of a display screen during the measurement of the repetitive reproducibility of the tapping force of the finger according to the embodiment. On the left side of FIG. 20, the display unit 130 displays a state in which a bar graph CF1 indicating the current value of the tapping force is within a region TR indicating a preset target range of the tapping force as the bar graph. On the right side of FIG. 20, the display unit 130 displays the region TR indicating the target range with high visibility when a bar graph CF2 indicating the current value of the tapping force is out of the region TR indicating the preset target range of the tapping force. For example, the display unit 130 changes the color, pattern, color density, shape, or the like of the region TR indicating the target range, thereby displaying the region with high visibility.

1-7. Measurement of Temporal Accuracy of Tapping Operation of a Finger

Figure 21:
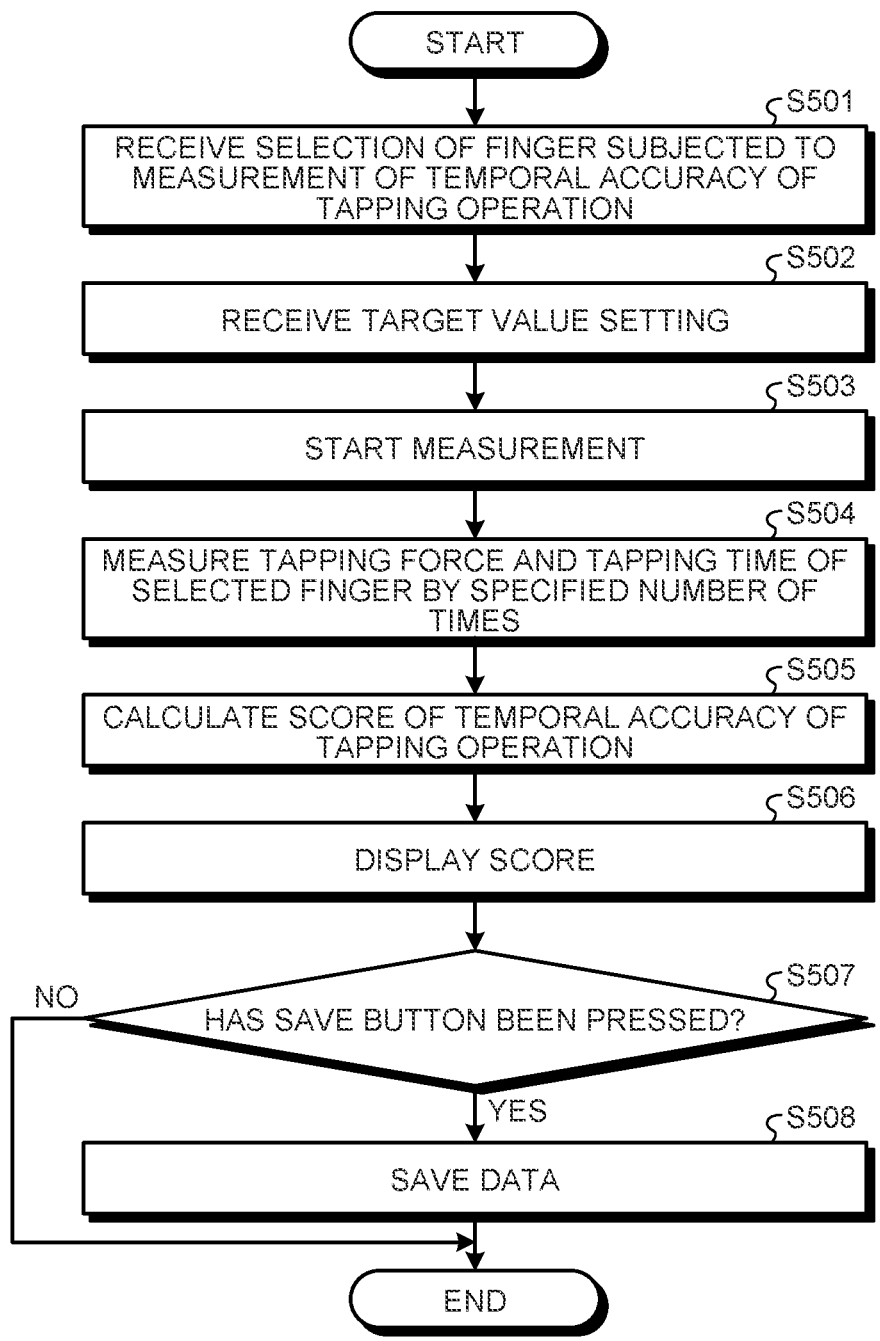
FIG. 21 is a flowchart illustrating a processing procedure of measurement of the temporal accuracy of tapping operation of the finger according to the embodiment.

Next, measurement of the temporal accuracy of the tapping operation according to the embodiment will be described with reference to FIGS. 21 to 24. First, a description will be given with reference to FIG. 21. FIG. 21 is a flowchart illustrating a processing procedure of the measurement of the temporal accuracy of the tapping operation of the finger according to the embodiment.

The processing unit 122 receives selection of a finger subjected to the measurement of the temporal accuracy of the tapping operation (Step S501). Subsequently, after receiving the selection of the finger, the processing unit 122 receives the setting of a target value (Step S502). Then, after receiving the setting of the target value, the processing unit 122 starts the measurement of the temporal accuracy of the tapping operation of the selected finger (Step S503).

Subsequently, after starting the measurement, the processing unit 122 measures the tapping force of the selected finger and the time during which tapping is performed (also referred to as a tapping time) by a specified number of times (Step S504). After completing the measurement, the processing unit 122 calculates a score indicating the temporal accuracy of the tapping operation (Step S505).

Subsequently, after calculating the score, the processing unit 122 displays the calculated score on the display unit 130 (Step S506).

Subsequently, the processing unit 122 determines whether or not the save button has been pressed (Step S507). When it is determined that the save button has been pressed (Step S507: Yes), the processing unit 122 saves the measured data in the storage unit 140 (Step S508).

On the other hand, when it is determined that the save button has not been pressed (Step S507: No), the processing unit 122 ends the processing.

Figure 22:
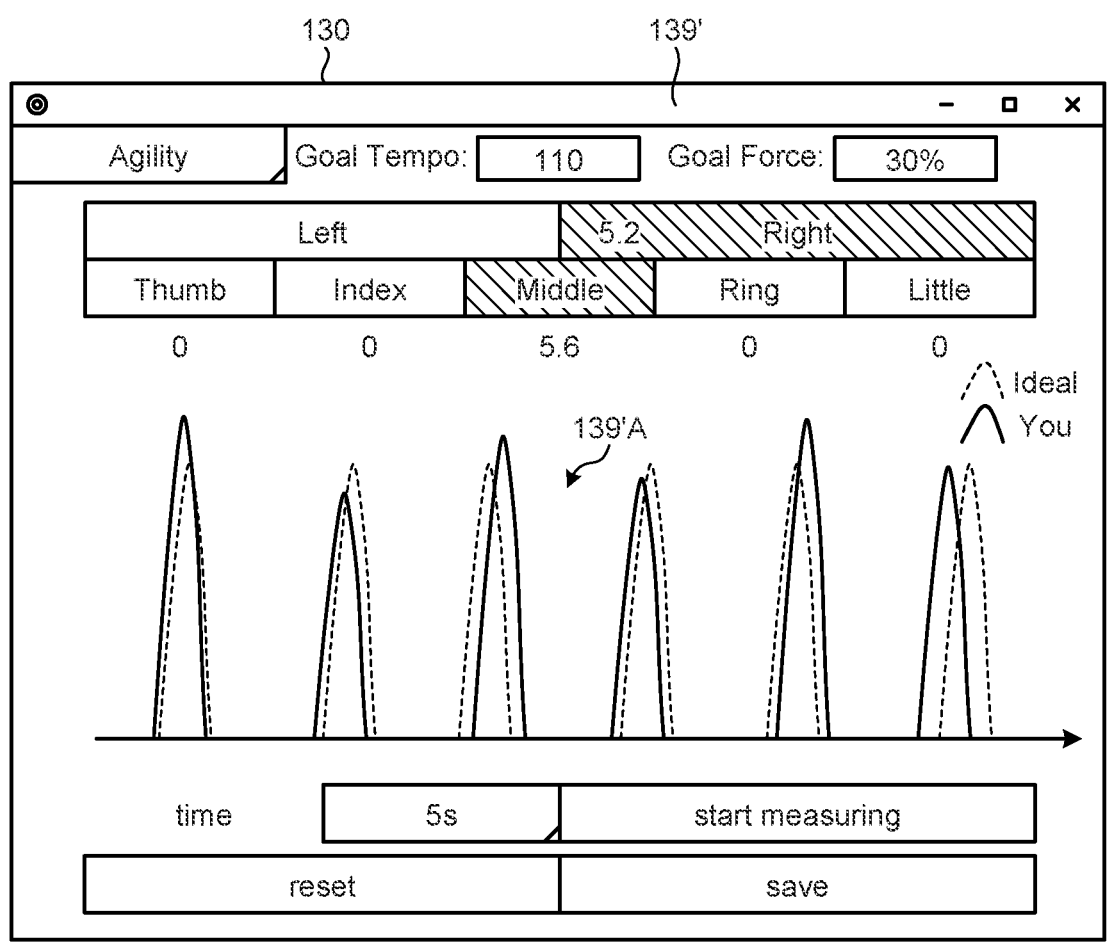
FIG. 22 is a view illustrating an example of a display screen during the measurement of the temporal accuracy of the tapping operation of the finger according to the embodiment.

Next, a description will be given with reference to FIG. 22. FIG. 22 is a view illustrating an example of a display screen during the measurement of the temporal accuracy of the tapping operation of the finger according to the embodiment. In FIG. 22, the display unit 130 displays a waveform indicating the tapping operation on a time axis. The display unit 130 indicates a target tapping operation in a dotted line. In addition, the display unit 130 indicates the measured tapping operation in a solid line.

Figure 23:
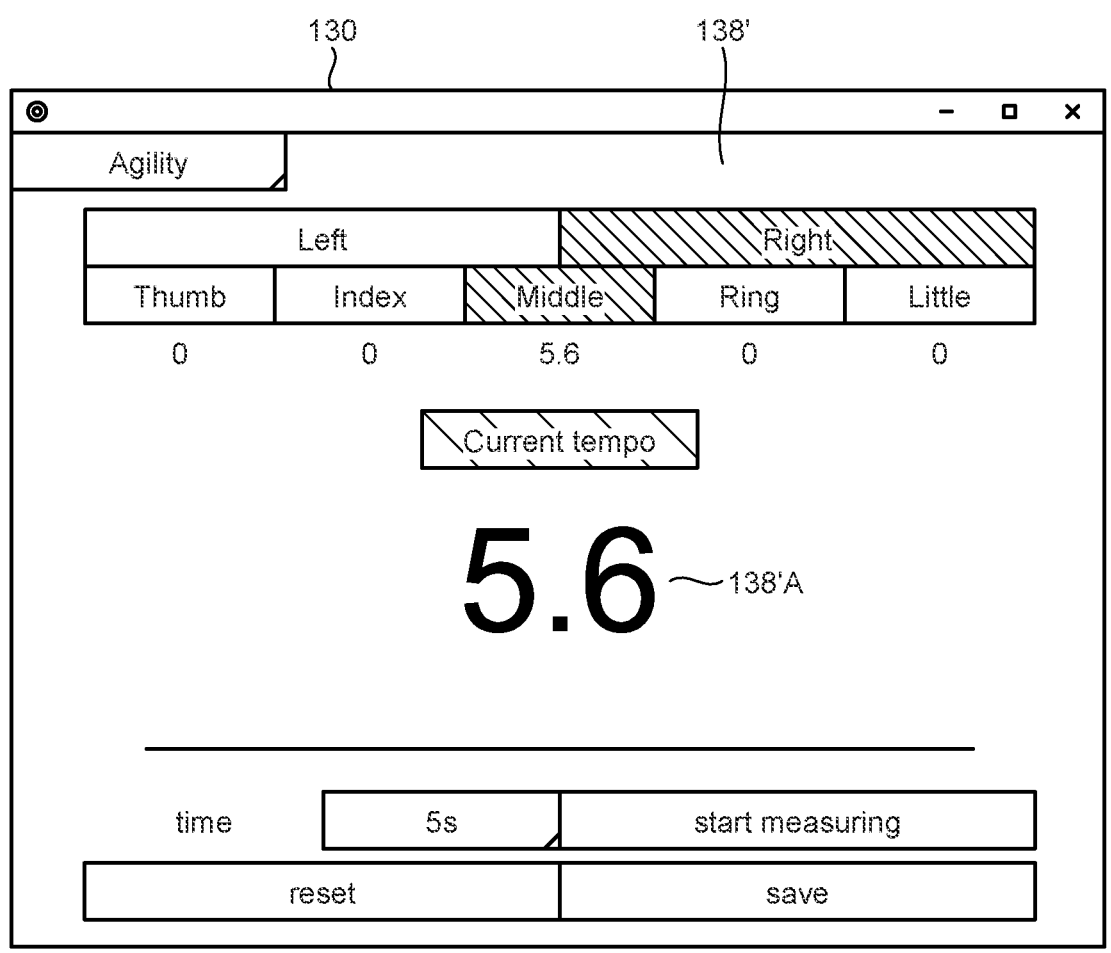
FIG. 23 is a view illustrating an example of the display screen during the measurement of the temporal accuracy of the tapping operation of the finger according to the embodiment.

Next, a description will be given with reference to FIG. 23. FIG. 23 is a view illustrating an example of the display screen during the measurement of the temporal accuracy of the tapping operation of the finger according to the embodiment. In FIG. 22, the display unit 130 displays a number 138'A indicating the tempo of tapping during the measurement. Alternatively, the display unit 130 may display tempo fluctuation of tapping during the measurement instead of the tempo of tapping during the measurement.

Figure 24:
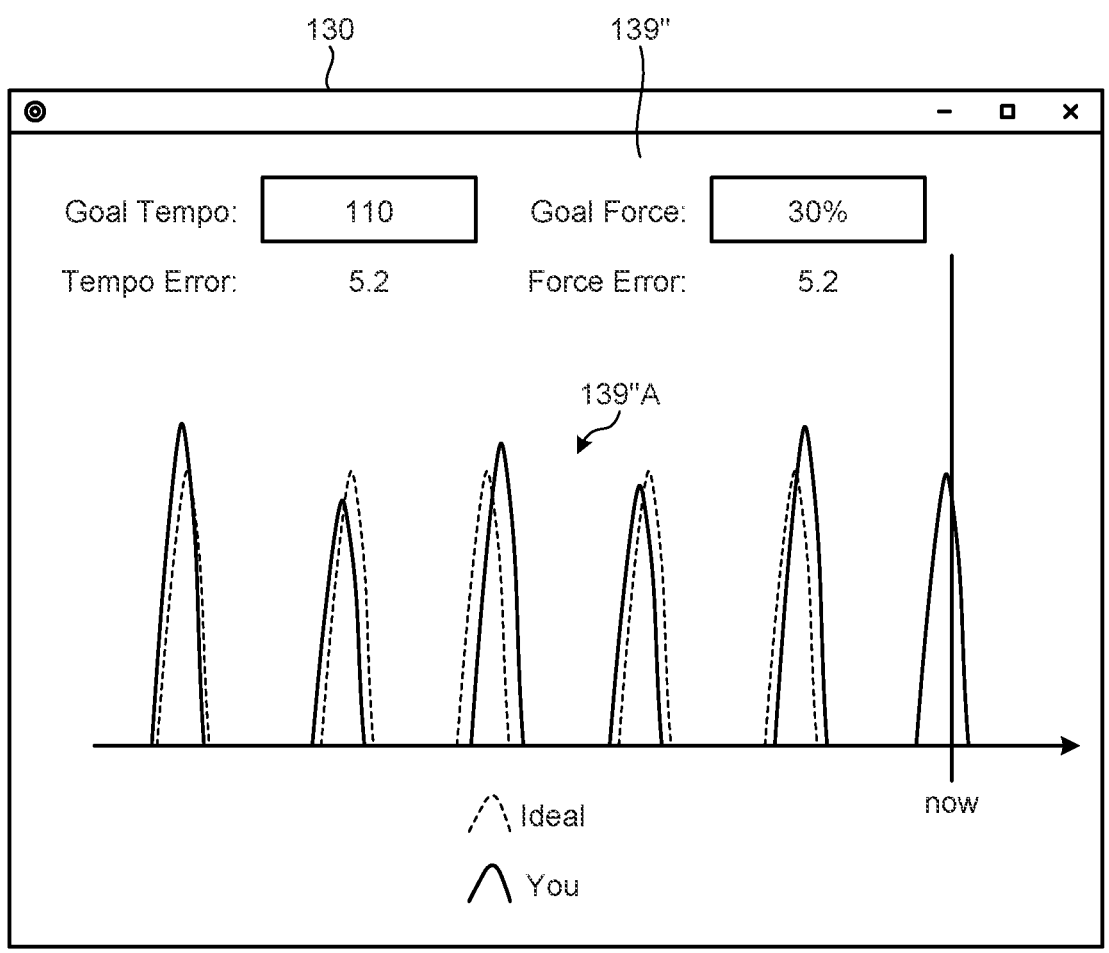
FIG. 24 is a view illustrating an example of the display screen of measurement results of the temporal accuracy of the tapping operation of the finger according to the embodiment.

Next, a description will be given with reference to FIG. 24. FIG. 24 is a view illustrating an example of the display screen of measurement results of the temporal accuracy of the tapping operation of the finger according to the embodiment. In FIG. 24, the display unit 130 displays a waveform indicating the tapping operation on the time axis. In addition, the display unit 130 displays the latest tapping such that the latest tapping is aligned to 0.

1-8. Training of Independence of a Finger

Figure 25:
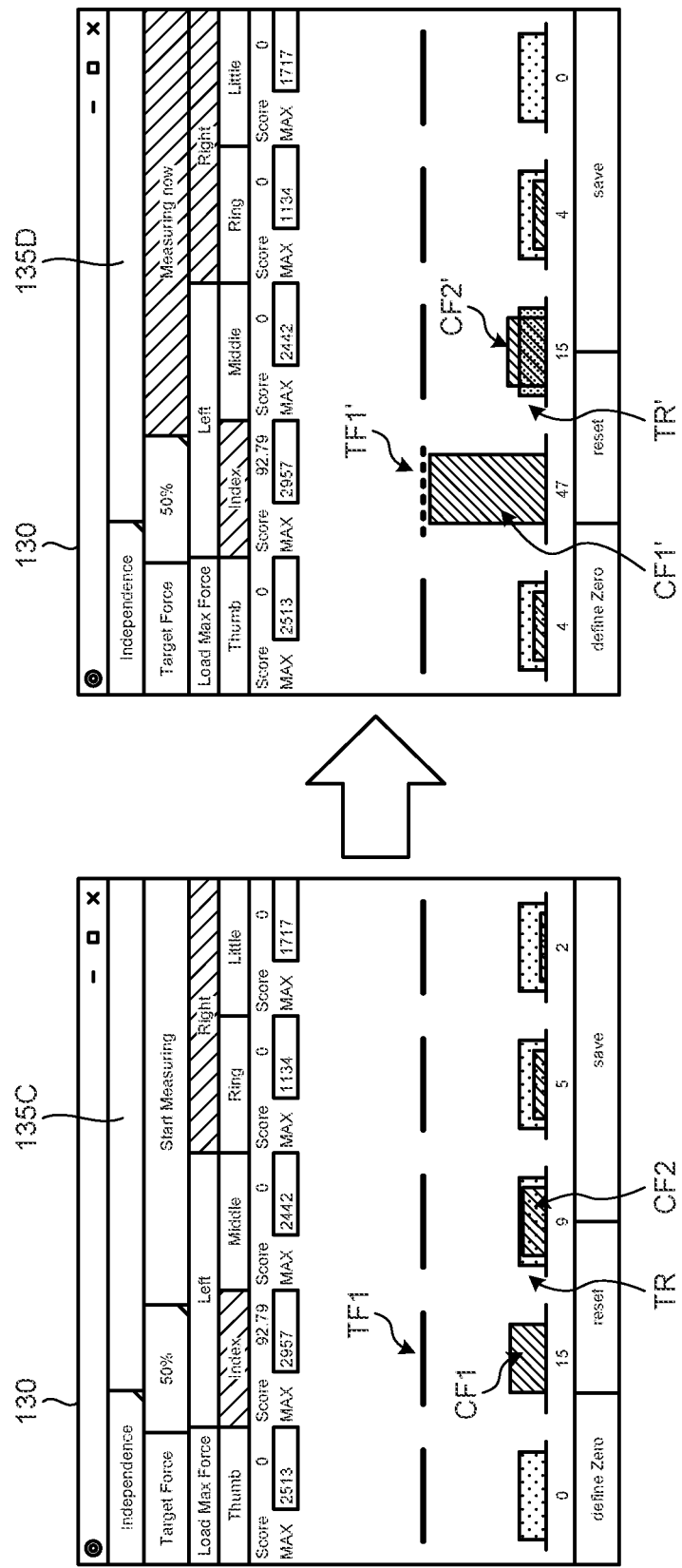
FIG. 25 is a view illustrating an example of a display screen during training of the independence of the finger according to the embodiment.

Next, training of the finger according to the embodiment will be described with reference to FIG. 25. FIG. 25 is a view illustrating an example of a display screen during training of the independence of the finger according to the embodiment. In the independence training, the user tenses a finger subjected to training so that the force is within a set target range, and relaxes the other fingers.

In FIG. 25, the display unit 130 displays a bar TF1 indicating the target range of the force of the finger subjected to training and a bar graph CF1 indicating the current value. In addition, the display unit 130 displays a bar graph TR indicating the target range of the force of a finger not subjected to training and a bar graph CF2 indicating the current value.

On the right side of FIG. 25, when a bar graph CF1' indicating the current value of the force of the finger subjected to training is within the target range, the display unit 130 displays a bar TF1' indicating the target range with high visibility. For example, the display unit 130 changes the color, pattern, color density, shape, or the like of the bar TF1' indicating the target value, thereby displaying the bar with high visibility. In addition, when a bar graph CF2' indicating the current value of the force of the finger not subjected to training exceeds the target range, the display unit 130 displays the region TR' indicating the target range with high visibility. For example, the display unit 130 changes the color, pattern, color density, shape, or the like of the region TR' indicating the target range, thereby displaying the region with high visibility.

1-9. Evaluation and Recommendation

The processing unit 122 executes information processing related to evaluation of the forces of the two or more different fingers based on a history of measurement results of the forces of the two or more different fingers. For example, the display unit 130 displays information related to the history of the measurement results of the forces of the two or more different fingers. In addition, the display unit 130 displays recommendation information related to training of the finger of the user based on the history of the measurement results of the forces of the two or more different fingers.

Furthermore, the processing unit 122 acquires information related to measurement results of the forces of the two or more different fingers of another user different from the user. The processing unit 122 executes information processing related to evaluation of the forces of the two or more different fingers of the user based on the information related to the measurement results of the forces of the two or more different fingers of the other user. For example, the display unit 130 displays information related to comparison results between the measurement results of the forces of the two or more different fingers of the other user and the measurement results of the forces of the two or more different fingers of the user. In addition, the display unit 130 displays recommendation information related to training of the two or more different fingers of the user based on the comparison results between the measurement results of the forces of the two or more different fingers of the other user and the measurement results of the forces of the two or more different fingers of the user.

1-10. First Modification

Figure 26:
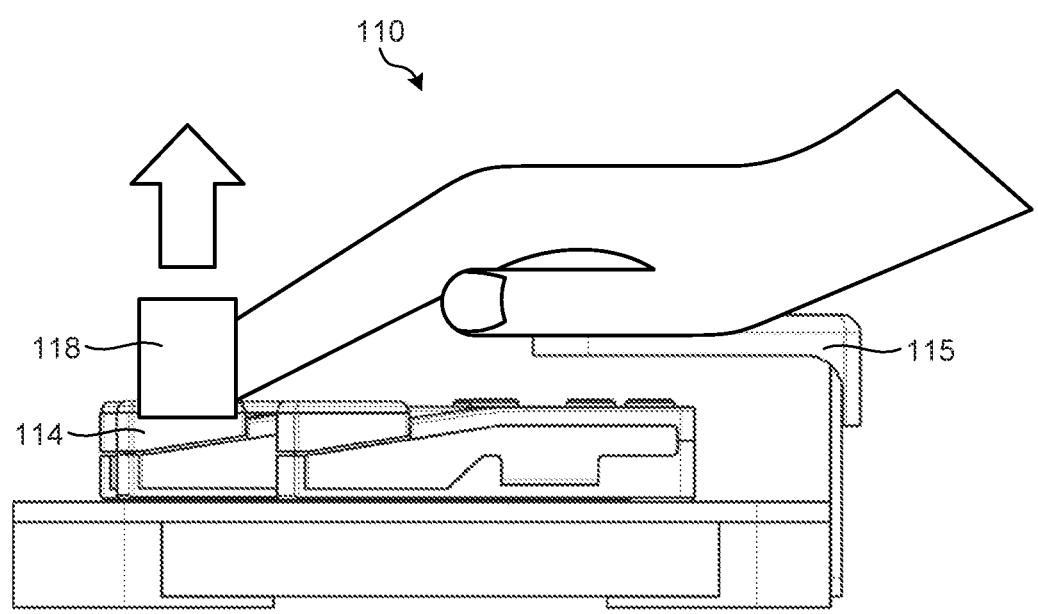
FIG. 26 is a side view of a force sensor according to a first modification of the embodiment.

Next, a force sensor according to a first modification of the embodiment will be described with reference to FIG. 26. FIG. 26 is a side view of the force sensor according to the first modification of the embodiment. In FIG. 26, a ring is attached to a pressing portion of the force sensor to measure the force of extension of a finger. At this time, the force sensor may be installed while being inclined at 90 degrees, and the ring may be attached as illustrated in FIG. 26 to measure the inward rotation force or the outward rotation force of each finger.

A force sensor 110 may be a triaxial force sensor instead of a uniaxial force sensor. This enables the force sensor 110 to measure a force in a horizontal direction in addition to a force in a vertical direction. Therefore, the force sensor 110 can more accurately evaluate the force of the finger by adding the force in the horizontal direction.

1-11. Second Modification

Next, a configuration of a force sensor according to a second modification of the embodiment will be described with reference to FIGS. 27 to 41. A force sensor 110B according to the second modification of the embodiment is different from the force sensor 110 according to the embodiment in that a fulcrum of a sensor unit 110C is arranged on a side opposite to the wrist. That is, the force sensor 110B according to the second modification of the embodiment is different from the force sensor 110 according to the embodiment in that the mounting direction of the sensor unit 110C is opposite to the mounting direction of the sensor unit 110A.

As described above, in the force sensor 110B, the sensor unit 110C is arranged in the mounting direction opposite to that of the sensor unit 110A, so that a palm of a user does not come directly above the sensor unit 110C, allowing the sensor position to be easily adjusted while a hand of the user is fixed. In addition, in the force sensor 110B, the palm of the user does not come directly above the sensor unit 110C, so that a fixing mechanism of the sensor unit 110C can be more firmly fixed to a support base as compared with the force sensor 110 according to the embodiment.

Figure 27:
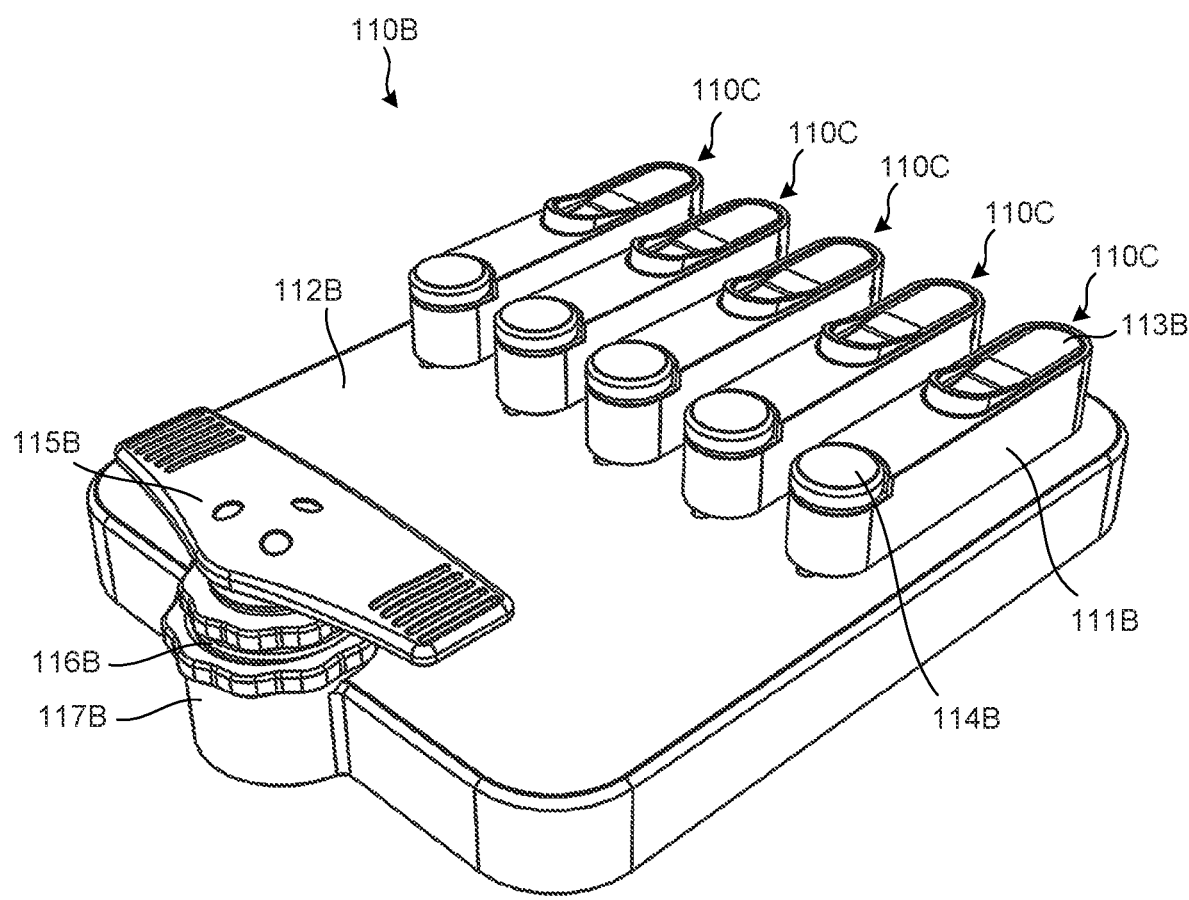
FIG. 27 is a perspective view of a force sensor according to a second modification of the embodiment.

FIG. 27 is a perspective view of the force sensor 110B according to the second modification of the embodiment. As illustrated in FIG. 27, the force sensor 110B includes five sensor units 110C each having a built-in force sensor, a support base 112B on which the five sensor units 110C are placed, and a support portion 115B that supports at least a part of the palm of a hand including two or more different fingers of the user.

The force sensor 110B detects each of the forces of the five fingers of the user using five force sensors built in each sensor unit 110C. For example, the force sensor built in the sensor unit 110C may be a triaxial force sensor.

The sensor unit 110C includes a structure 111B that holds the force sensor, a fixing portion 113B that fixes the structure 111B to the support base 112B, and a pressing portion 114B that indicates a place to be pressed by the finger of the user. The pressing portion 114B is provided on an upper surface of the structure 111B.

The force sensor 110B includes two or more structures 111B. Specifically, the force sensor 110B includes five structures 111B.

The two or more structures 111B hold each of the two or more force sensors. Specifically, the five structures 111B hold each of the five force sensors. For example, the five structures 111B hold each of five triaxial force sensors.

In addition, each of the two or more fixing portions 113B fixes each of the two or more structures 111B to the support base 112B. Specifically, each of the five fixing portions 113B fixes each of the five structures 111B to the support base 112B. Specifically, the fixing portion 113B includes a quick release mechanism, and fixes the structure 111B to the support base 112B through one-touch operation by raising and lowering a quick release lever. Alternatively, each of the five structures 111B may be fixed to the support base 112B with a screw, a lever, or an electromagnet. Further, each of the five structures 111B may be automatically fixed to the support base 112B using a solenoid or a motor.

The support base 112B is provided with two or more holding mechanisms 119B that movably hold each of the two or more force sensors on the upper surface. Specifically, the support base 112B is provided with five holding mechanisms 119B (see FIG. 33) that movably hold each of the five force sensors on the upper surface.

In addition, the two or more holding mechanisms 119B fix each of the two or more force sensors to the support base 112B when each of the two or more structures 111B is fixed to each of the two or more holding mechanisms 119B by each of the two or more fixing portions 113B. Specifically, the five holding mechanisms 119B fix each of the five force sensors to the support base 112B when each of the five structures 111B is fixed to each of the five holding mechanisms 119B by each of the five fixing portions 113B.

In addition, each of the two or more force sensors is movably held on the upper surface by the holding mechanism 119B in a state in which the fixing portion 113B is loosened. Specifically, each of the two or more force sensors is held rotatably and linearly on the upper surface by the holding mechanism 119B in the state in which the fixing portion 113B is loosened. For example, each of the five force sensors is movably held on the upper surface by the holding mechanism 119B in the state in which the fixing portion 113B is loosened. For example, each of the five force sensors is held rotatably and linearly on the upper surface by the holding mechanism 119B in the state in which the fixing portion 113B is loosened.

In addition, the support portion 115B supports at least a part of the palm of the hand including the two or more different fingers of the user. Specifically, the support portion 115B supports a region connecting each MP joint of the index finger, the middle finger, the ring finger, and the little finger, and the central portion of the metacarpal in the palm of the user. In other words, the support portion 115B supports a region around the bases of the four fingers between the index finger to the little finger of the user, called a fingertip ball. With this configuration, the information processing apparatus 100 can perform more stable measurement as compared with the force sensor 110 according to the embodiment.

In addition, the support base 112B is provided with a holding mechanism (not illustrated) that holds the support portion 115B so that the height of the support portion 115B can be changed in a direction perpendicular to the upper surface of the support base 112B. The support base 112B is provided with a double nut structure as an example of the holding mechanism (not illustrated). Specifically, the support portion 115B is a component (hereinafter, also referred to as an armrest) integrated with a bolt portion 115C (see FIG. 29) having a bolt structure. The support base 112B is provided with a first double nut 116B into which the bolt portion 115C is inserted, and a second double nut 117B that fixes the first double nut 116B to the support base 112B.

Figure 28:
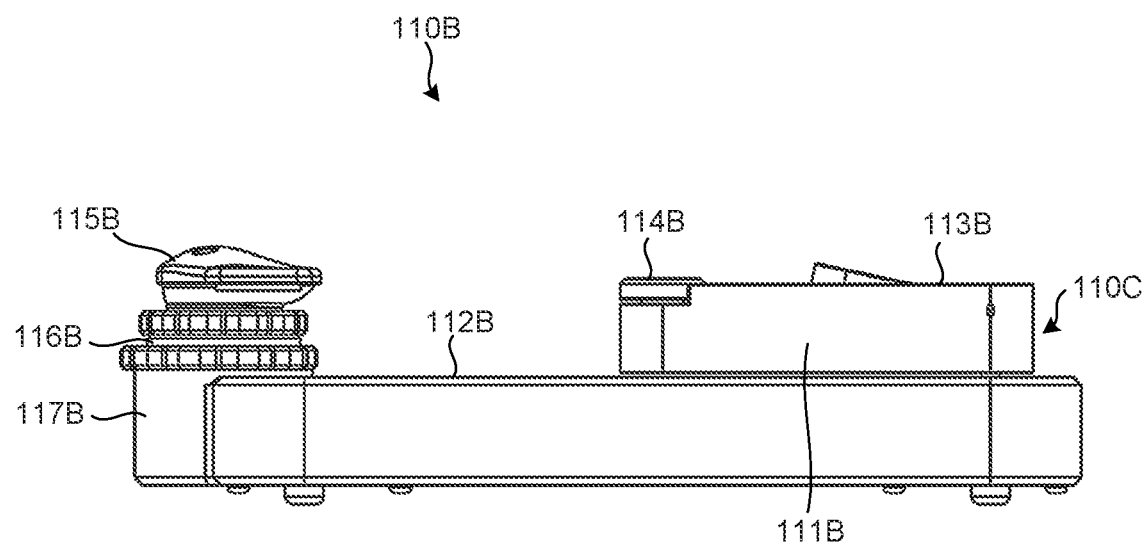
FIG. 28 is a side view of the force sensor according to the second modification of the embodiment.

FIG. 28 is a side view of the force sensor 110B according to the second modification of the embodiment. In FIG. 28, the bolt portion 115C connected below the support base 112B is completely embedded in the first double nut 116B and is invisible, and merely the support portion 115B and the base portion of the first double nut 116B are visible. In addition, the outer side of the first double nut 116B has a bolt structure. In FIG. 28, the bolt portion of the first double nut 116B is completely embedded in the second double nut 117B and is invisible, and merely the base portion of the second double nut 117B is visible.

Figure 29:
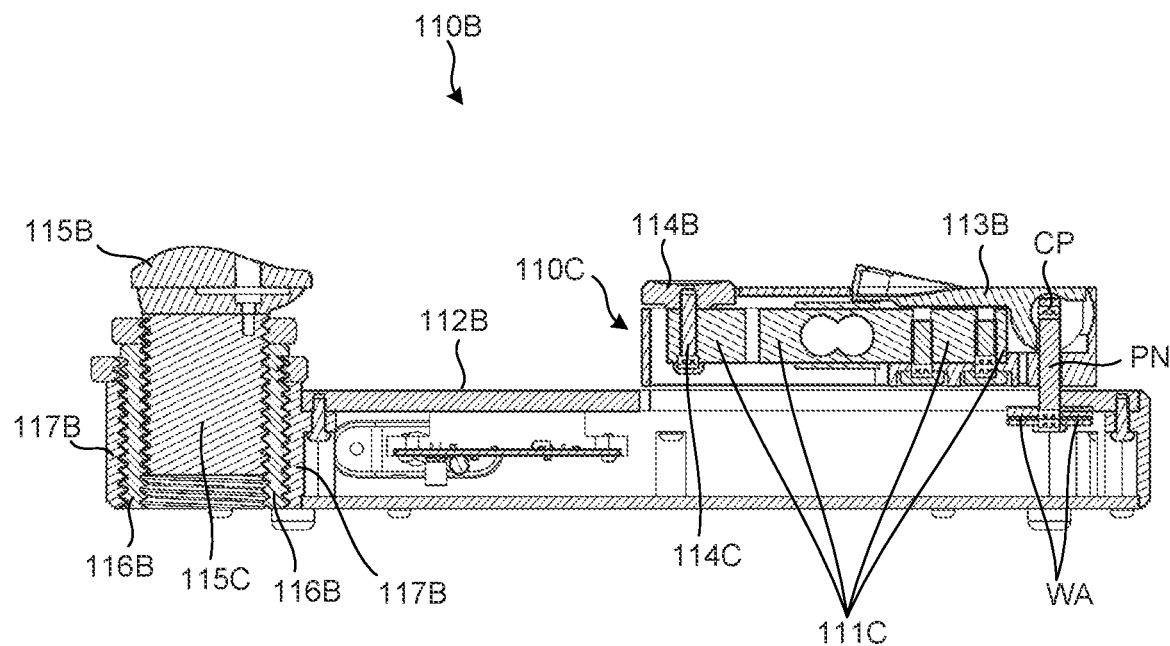
FIG. 29 is a side view illustrating an internal structure of the force sensor according to the second modification of the embodiment.

FIG. 29 is a side view illustrating an internal structure of the force sensor 110B according to the second modification of the embodiment. As illustrated in FIG. 29, a force sensor 111C is built in the sensor unit 110C. In addition, a force applied to the pressing portion 114B is input to the force sensor 111C through a screw 114C connected to the pressing portion 114B.

In the example illustrated in FIG. 29, when the fixing portion 113B (quick release lever) is lifted and the fixing portion 113B is rotated counterclockwise around a rotation center CP of the lever, a pin PN connected to the rotation center CP is pressed against a washer WA. This allows the structure 111B, which is the exterior of the sensor unit 110C, to be fixed to the upper surface of the support base 112B.

In addition, the support base 112B is provided with a two-stage double nut structure including the first double nut 116B into which the bolt portion 115C is inserted and the second double nut 117B that fixes the first double nut 116B to the support base 112B. Furthermore, the support portion 115B is held so that the height can be changed in the direction perpendicular to the upper surface of the support base 112B in a state in which the first double nut 116B or the second double nut 117B is loosened.

In addition, the surface of the support portion 115B is provided with a convex shape corresponding to the center of the palm. With this configuration, the information processing apparatus 100 can facilitate alignment of the palm of the user with the support portion 115B.

Figure 30:
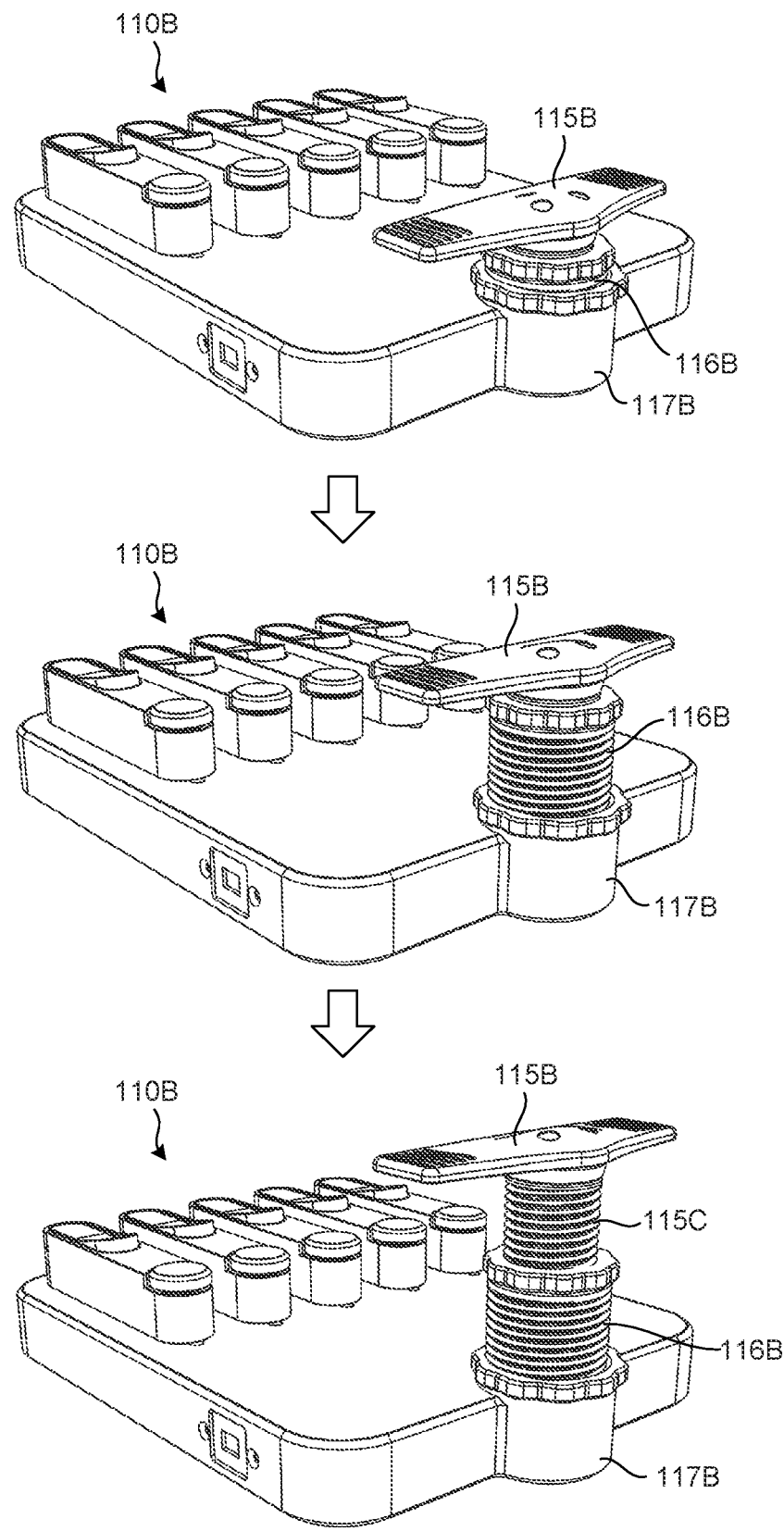
FIG. 30 is a perspective view of the force sensor according to the second modification of the embodiment as viewed from a palm rest side.

FIG. 30 is a perspective view of the force sensor 110B according to the second modification of the embodiment as viewed from a palm rest side. As illustrated in FIG. 30, the support portion 115B is held so that the length of the bolt portion of the first double nut 116B can be changed in the direction perpendicular to the upper surface of the support base 112B in a state in which the second double nut 117B is loosened. In addition, the support portion 115B is held so that the length of the bolt portion 115C connected to the support portion 115B can be changed in the direction perpendicular to the upper surface of the support base 112B in a state in which the first double nut 116B is loosened.

As described above, the information processing apparatus 100 includes the dual double nut structure so that the height of the palm rest can be adjusted in a compact manner. In addition, the information processing apparatus 100 has the dual double nut structure so that backlash can be reduced, allowing a stable measurement of the force of the finger.

Figure 31:
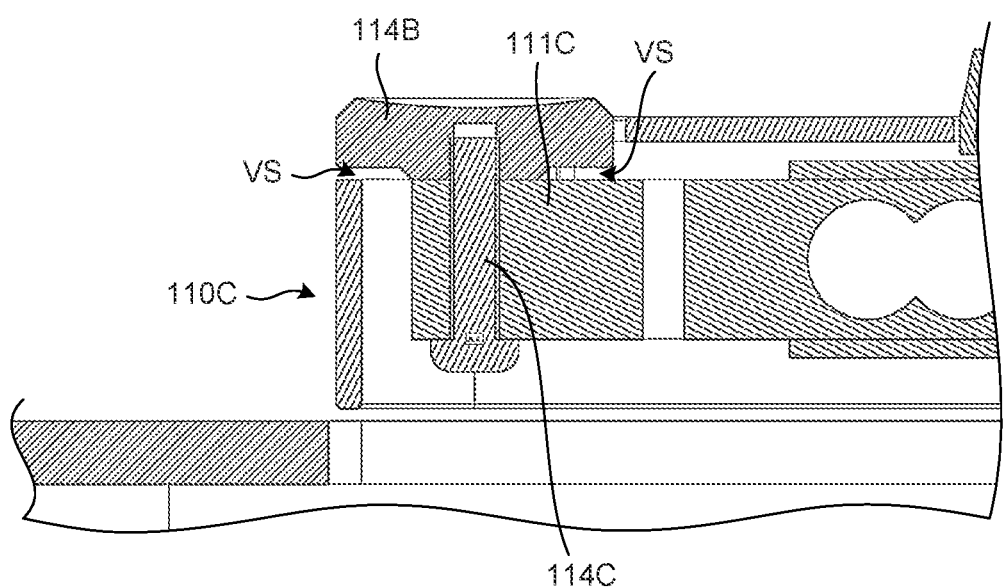
FIG. 31 is an enlarged view of a part of the side view illustrating the internal structure of the force sensor according to the second modification of the embodiment.

FIG. 31 is an enlarged view of a part of the side view illustrating the internal structure of the force sensor 110B according to the second modification of the embodiment. FIG. 31 is an enlarged view of the vicinity of the pressing portion 114B illustrated in FIG. 29. As illustrated in FIG. 31, the upper surface of the pressing portion 114B is provided with a concave shape corresponding to a position on which a fingertip of the finger is placed. Thus, the information processing apparatus 100 can stabilize the position on which the fingertip is placed for every measurement by providing the concave shape on the upper surface of the pressing portion 114B.

In addition, a gap VS exists between the pressing portion 114B and the upper surface of the sensor unit 110C. For example, it can be seen that the gap VS exists between the pressing portion 114B and the force sensor 111C. The gap VS is used to mount a jig for progress measurement described later with reference to FIG. 32 to the pressing portion 114B.

Figure 32:
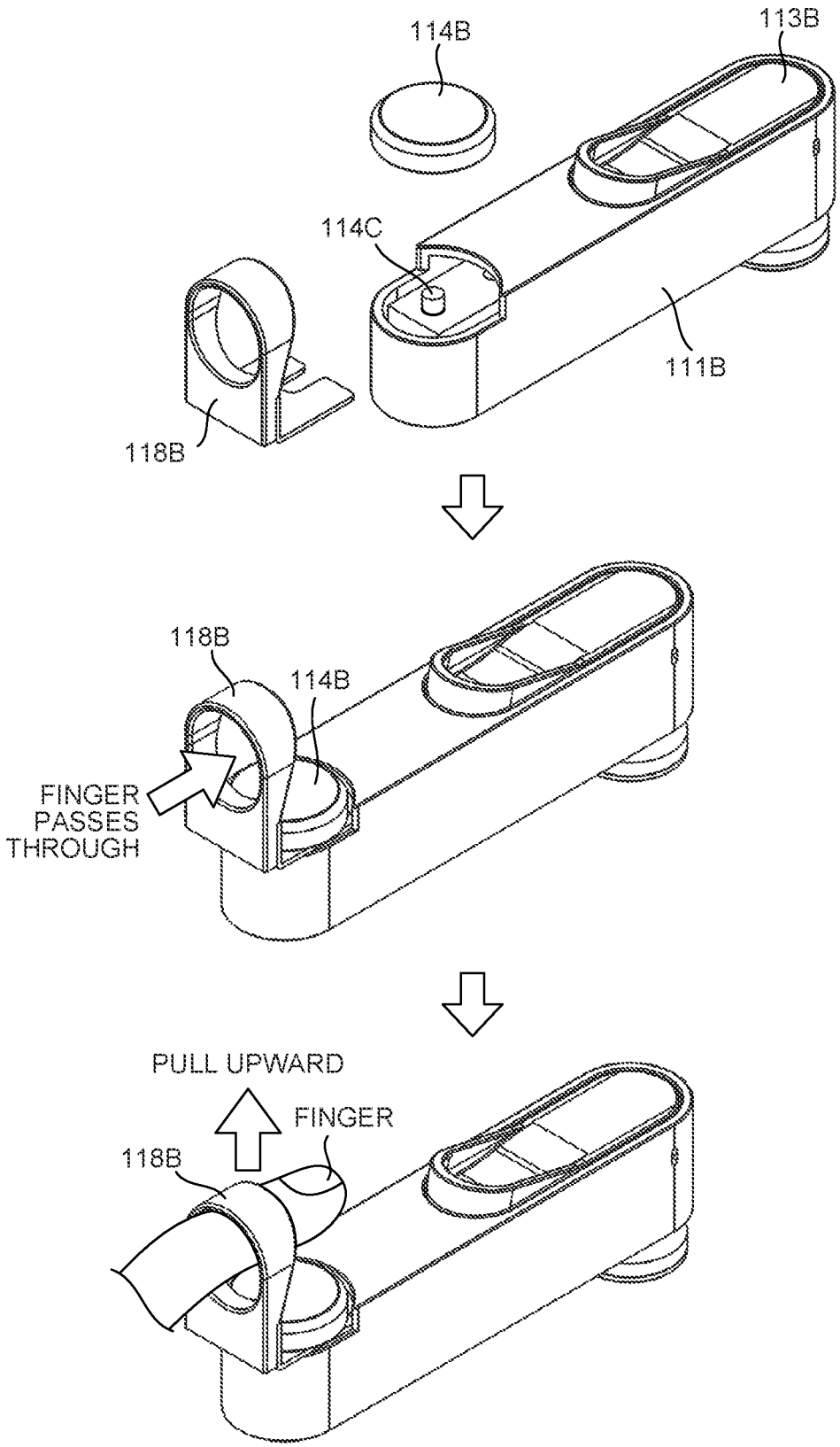
FIG. 32 is an example of a method of mounting a jig for progress measurement according to the second modification of the embodiment.

FIG. 32 is an example of a method of mounting a jig for progress measurement according to the second modification of the embodiment. In FIG. 32, one of the sensor units 110C will be described as an example. As illustrated in FIG. 32, the screw 114C having a convex shape is provided on the upper surface of the structure 111B on the opposite side of the fixing portion 113B. In addition, a jig 118B for progress measurement includes a ring-shaped first portion through which the user's finger passes and a second portion provided with a U-shaped groove corresponding to the screw 114C having the convex shape. Furthermore, a nut having a concave shape corresponding to the screw 114C having the convex shape is provided on a lower surface of the pressing portion 114B.

To mount the jig 118B for progress measurement, first, the U-shaped groove of the second portion of the jig 118B for progress measurement is mounted to the screw 114C having the convex shape. Subsequently, the concave nut provided on the lower surface of the pressing portion 114B is mounted to the screw 114C having the convex shape in a state in which the pressing portion 114B is placed on the upper surface of the second portion of the jig 118B for progress measurement.

In addition, when the progress of the finger is measured using the jig 118B for progress measurement, the finger of the user passes through the first portion of the jig 118B for progress measurement. Subsequently, the first portion of the jig 118B for progress measurement is pulled upward by the finger of the user. That is, the finger of the user progresses in the direction perpendicular to the upper surface of the support base 112B. Furthermore, the information processing apparatus 100 can measure the force for each finger, the force of each finger when the force is simultaneously exerted with the five fingers, the independence of the finger, and the agility of the finger during progress measurement.

The force sensor 111C may be a triaxial force sensor. With this configuration, the information processing apparatus 100 can measure the inward or outward rotation force of the finger in a state in which the jig 118B for progress measurement is mounted on the finger. Here, the inward rotation or outward rotation of the finger refers to movement in which the finger is moved in the horizontal direction in the same posture.

Figure 33:
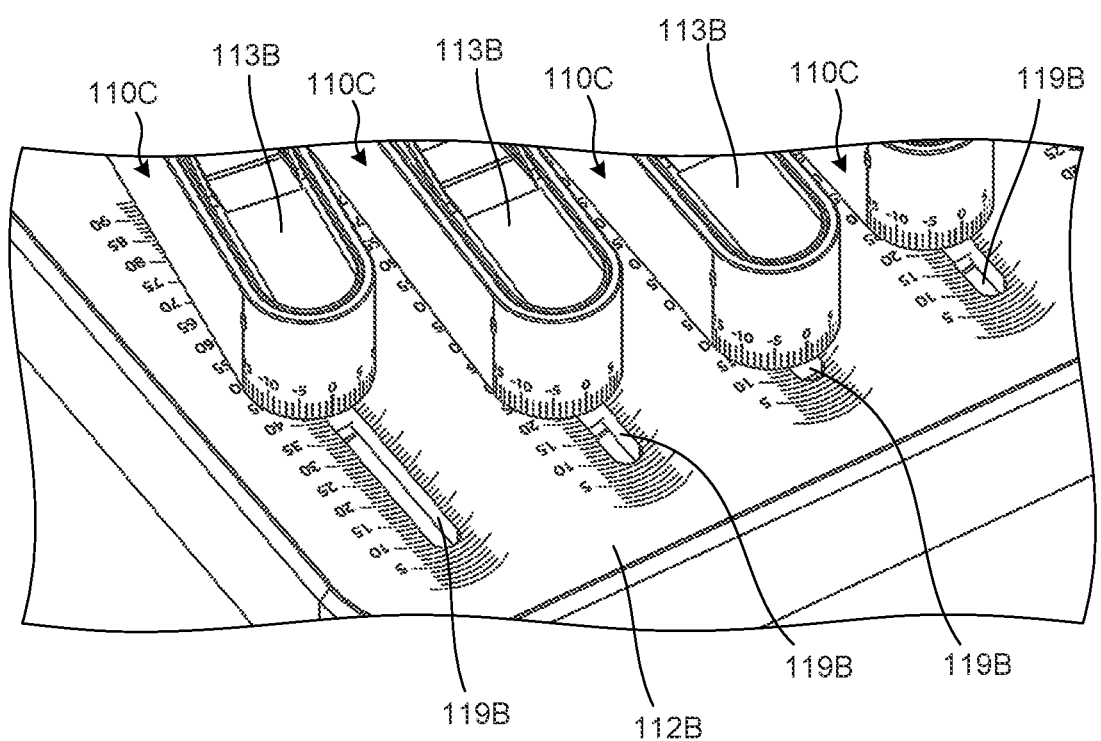
FIG. 33 is an enlarged view of a part of the perspective view of the force sensor according to the second modification of the embodiment.

FIG. 33 is an enlarged view of a part of the perspective view of the force sensor 110B according to the second modification of the embodiment. In FIG. 33, a scale allowing measurement of the angle of the sensor unit 110C on the upper surface of the support base 112B is provided on the side surface in the vicinity of the fixing portion 113B of the sensor unit 110C. In addition, a scale allowing measurement of the position of the sensor unit 110C on the upper surface of the support base 112B is provided beside the holding mechanism 119B (rectangular groove) on the upper surface of the support base 112B. With this configuration, the information processing apparatus 100 can record the position and angle of each sensor unit 110C on the upper surface of the support base 112B, and thus can measure the force of the finger under the same measurement condition every time. Therefore, the information processing apparatus 100 can obtain a stable measurement result.

The sensor unit 110C may include a potentiometer. With this configuration, the information processing apparatus 100 can automatically acquire the values of the position and angle of each sensor unit 110C on the upper surface of the support base 112B.

Figure 34:
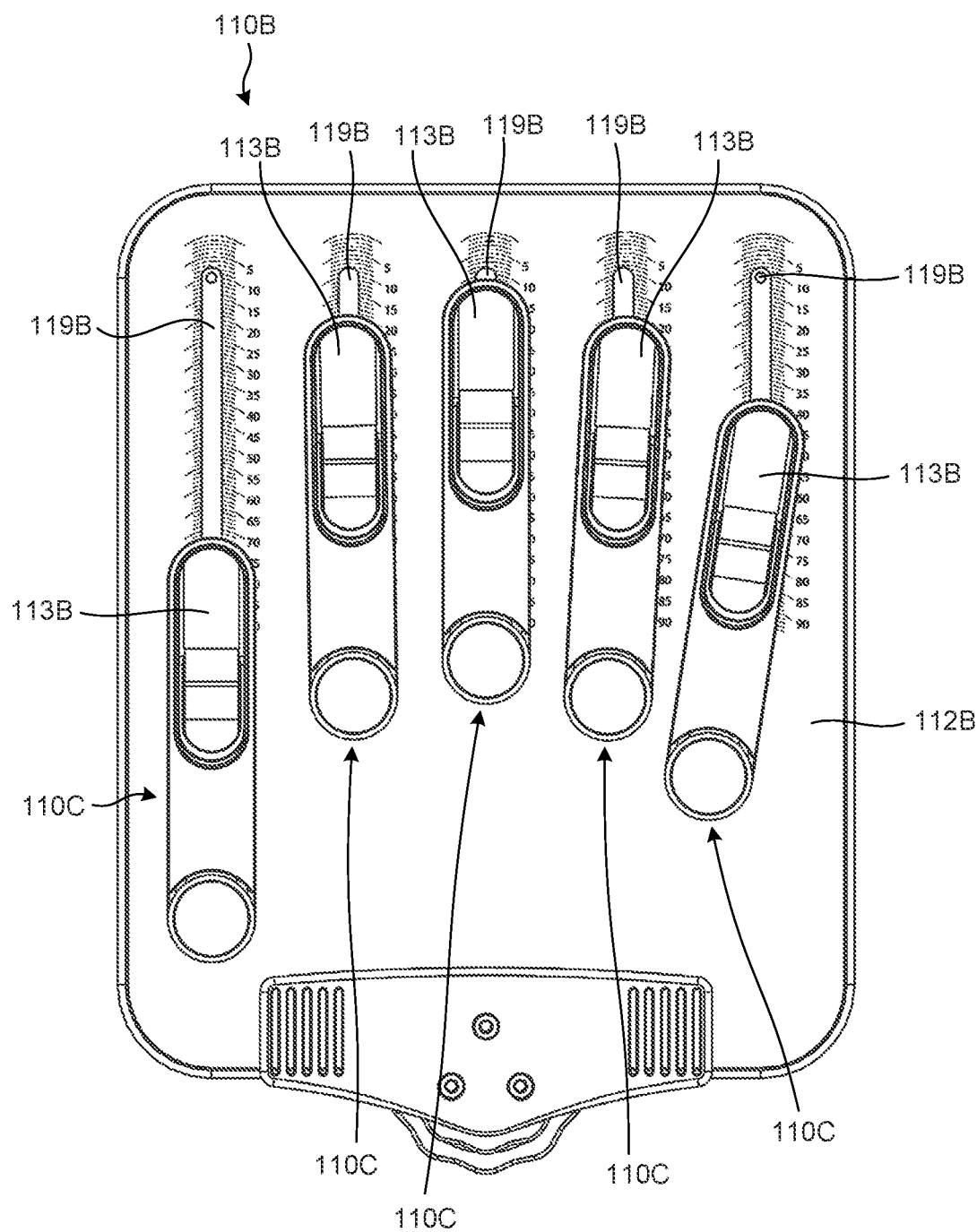
FIG. 34 is a top view of the force sensor according to the second modification of the embodiment.

FIG. 34 is a top view of the force sensor 110B according to the second modification of the embodiment. As illustrated in FIG. 34, each sensor unit 110C is movably held on the upper surface of the support base 112B along a holding mechanism 119B that is a rectangular groove.

Figure 35:
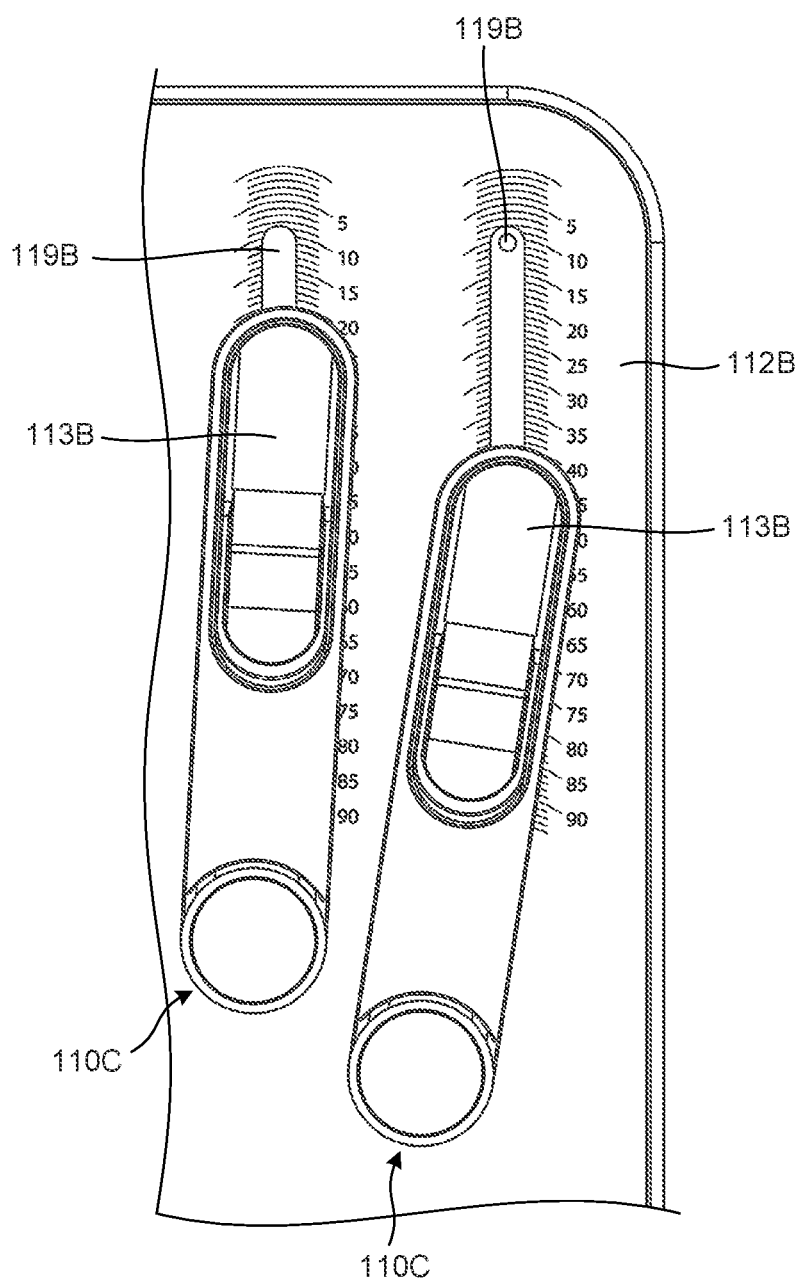
FIG. 35 is an enlarged view of a part of the top view of the force sensor according to the second modification of the embodiment.

FIG. 35 is an enlarged view of a part of the top view of the force sensor 110B according to the second modification of the embodiment. FIG. 35 is an enlarged view of the vicinity of the upper right of the support base 112B in the top view illustrated in FIG. 34. A state is illustrated in which a scale in 1 mm unit is provided on both sides of the holding mechanism 119B (rectangular groove) on the upper surface of the support base 112B from 5 mm to 90 mm.

Figure 36:
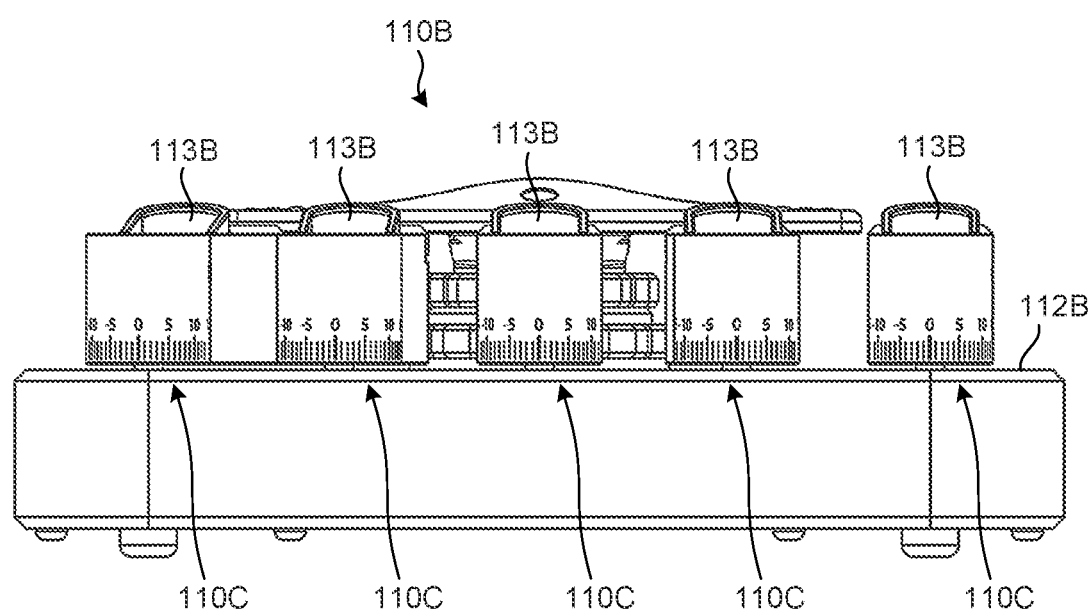
FIG. 36 is a side view of the force sensor according to the second modification of the embodiment as viewed from a sensor unit side.

FIG. 36 is a side view of the force sensor 110B according to the second modification of the embodiment as viewed from a sensor unit side. FIG. 36 illustrates a state in which a scale in 1 mm unit is provided on the side surface of the end of the sensor unit 110C on the fixing portion 113B side symmetrically as viewed in a longitudinal direction of the sensor unit 110C.

Figure 37:
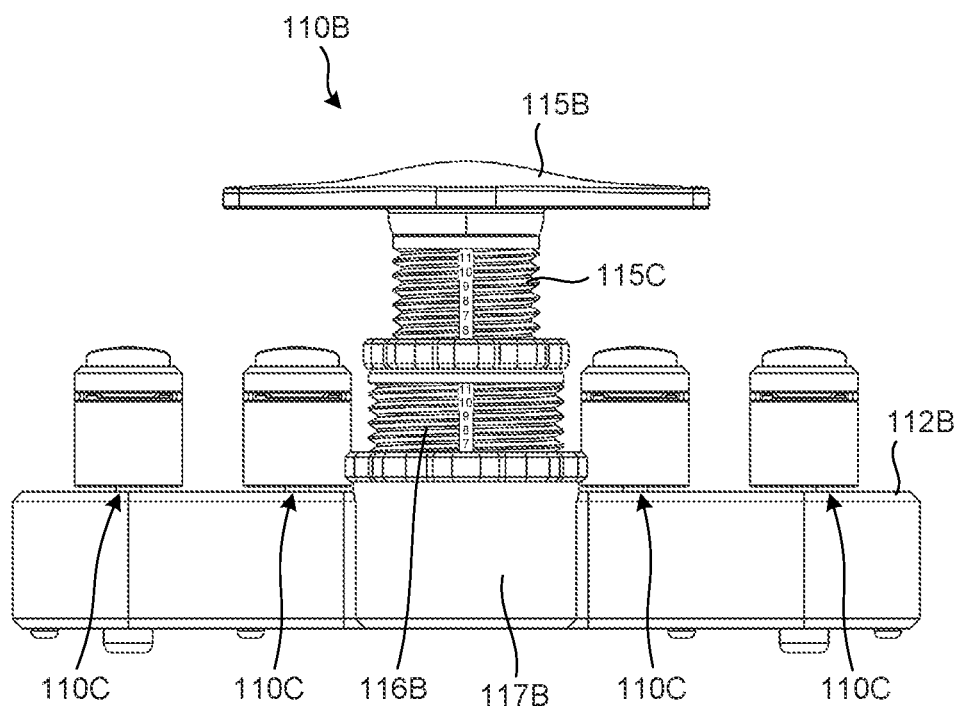
FIG. 37 is a side view of the force sensor according to the second modification of the embodiment as viewed from the palm rest side.

FIG. 37 is a side view of the force sensor 110B according to the second modification of the embodiment as viewed from the palm rest side. As illustrated in FIG. 37, a scale allowing measurement of the length of the bolt portion 115C is provided on the surface of the bolt portion 115C located below the support portion 115B. In addition, a scale allowing measurement of the length of the bolt area on the surface of the first double nut 116B is provided on the surface of the first double nut 116B. With this configuration, the information processing apparatus 100 can record the height of the support portion 115B, and thus can measure the force of the finger under the same measurement condition every time. Therefore, the information processing apparatus 100 can obtain a stable measurement result.

Figure 38:
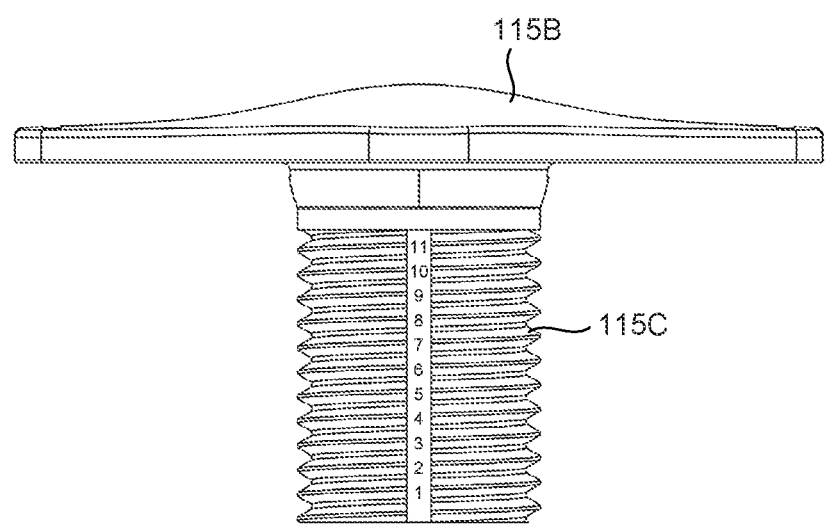
FIG. 38 is a side view of a bolt constituting a palm rest according to the second modification of the embodiment.

FIG. 38 is a side view of a bolt constituting the palm rest according to the second modification of the embodiment. FIG. 38 illustrates a state in which a scale in 1 mm unit is provided on the surface of the bolt portion 115C located below the support portion 115B from 1 mm to 11 mm.

Figure 39:
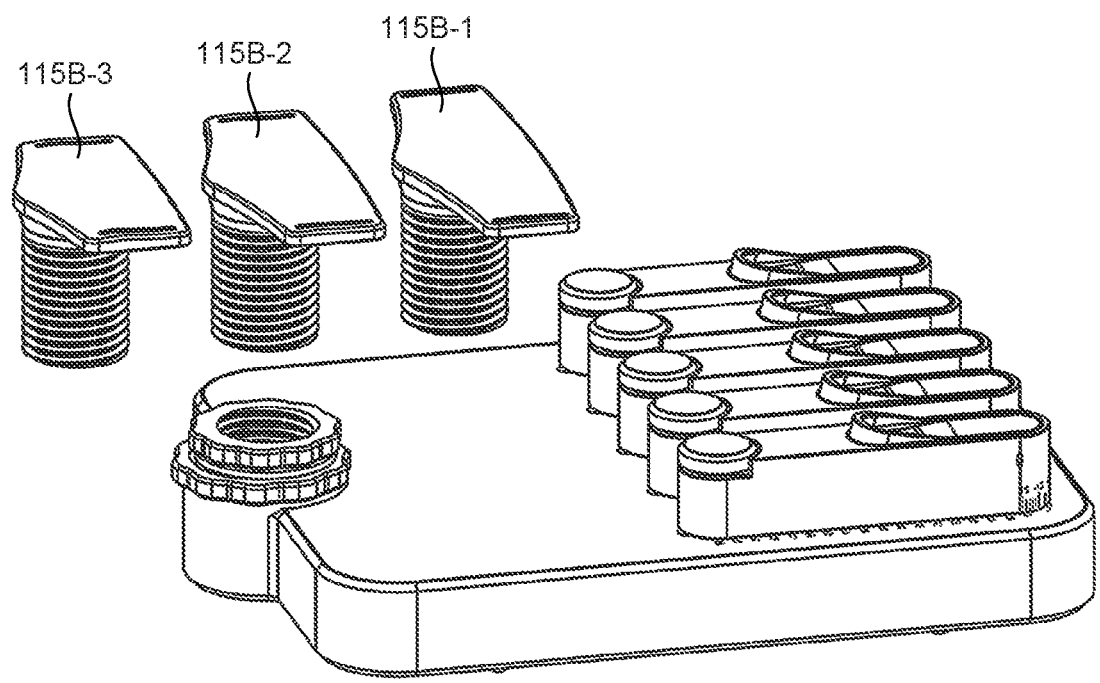
FIG. 39 is an example of an attachment of the palm rest to correspond to a plurality of hands according to the second modification of the embodiment.

Next, a description will be given with reference to FIG. 39. FIG. 39 illustrates an example of an attachment of the palm rest according to the second modification of the embodiment to correspond to a plurality of hands. In FIG. 39, three support portions 115B-1 to 115B-3 having different sizes are illustrated. Thus, by preparing several palm rests having different sizes, the palm rest can be replaced according to the size of the hand of the user. With this configuration, the information processing apparatus 100 can perform measurement that corresponds to each of hands having different sizes such as hands of a child and an adult, for example.

Figure 40:
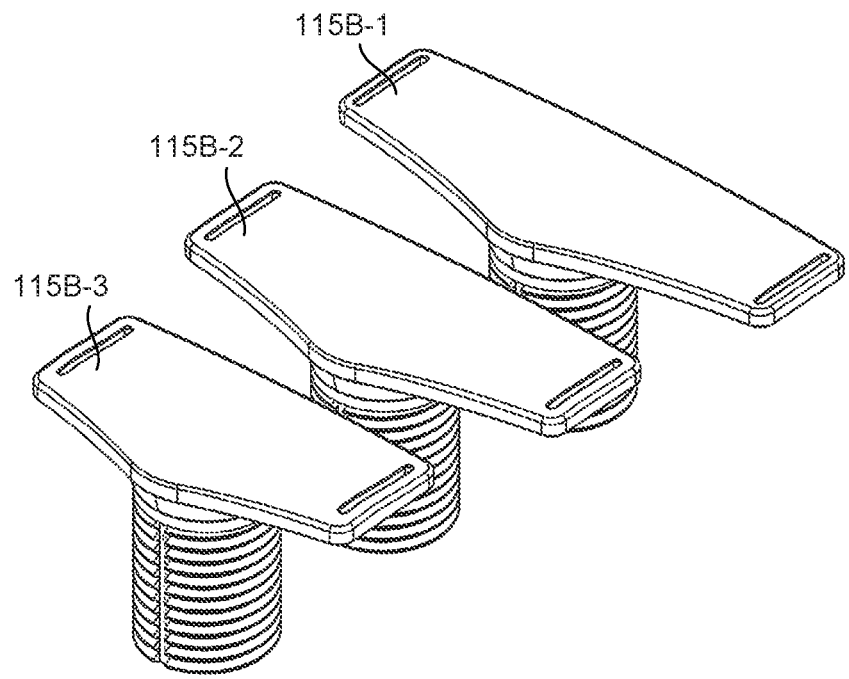
FIG. 40 is a perspective view of the attachment of the palm rest to correspond to the plurality of hands according to the second modification of the embodiment.

Next, a description will be given with reference to FIG. 40. FIG. 40 illustrates a perspective view of an attachment of the palm rest according to the second modification of the embodiment to correspond to a plurality of hands. As illustrated in FIG. 40, the support portion 115B-2 having a standard size, the support portion 115B-1 larger than the support portion 115B-2, and the support portion 115B-3 smaller than the support portion 115B-2 may be prepared. In addition, grooves through which a band for fixing the user's hand on the palm rest passes are provided at both ends of the three support portions 115B-1 to 115B-3.

Figure 41:
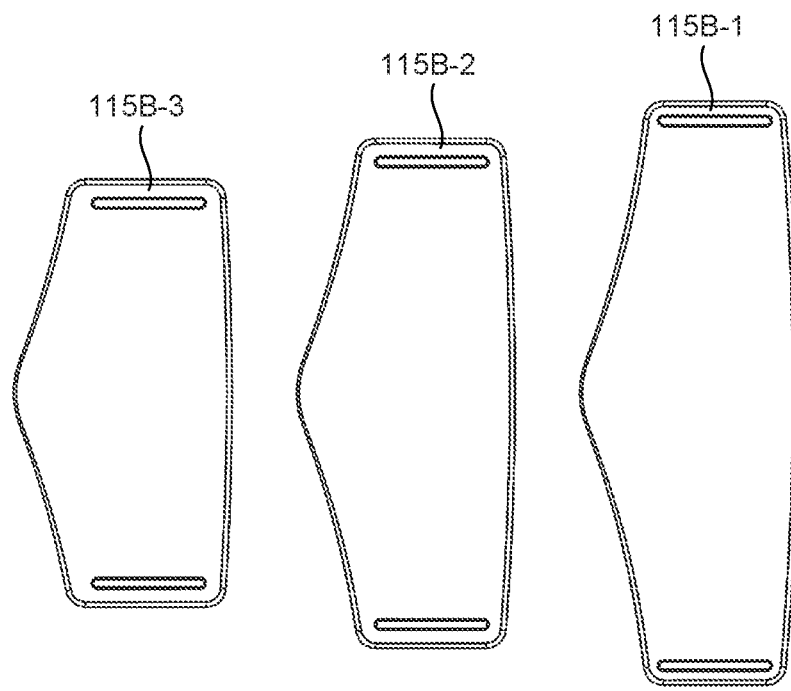
FIG. 41 is a top view of the attachment of the palm rest to correspond to the plurality of hands according to the second modification of the embodiment.

Next, a description will be given with reference to FIG. 41. FIG. 41 illustrates a top view of an attachment of the palm rest according to the second modification of the embodiment to correspond to a plurality of hands. As illustrated in FIG. 41, the shapes of the three support portions 115B-1 to 115B-3 may be line-symmetric so as to correspond to the measurement of the left and right hands.

Figure 42:
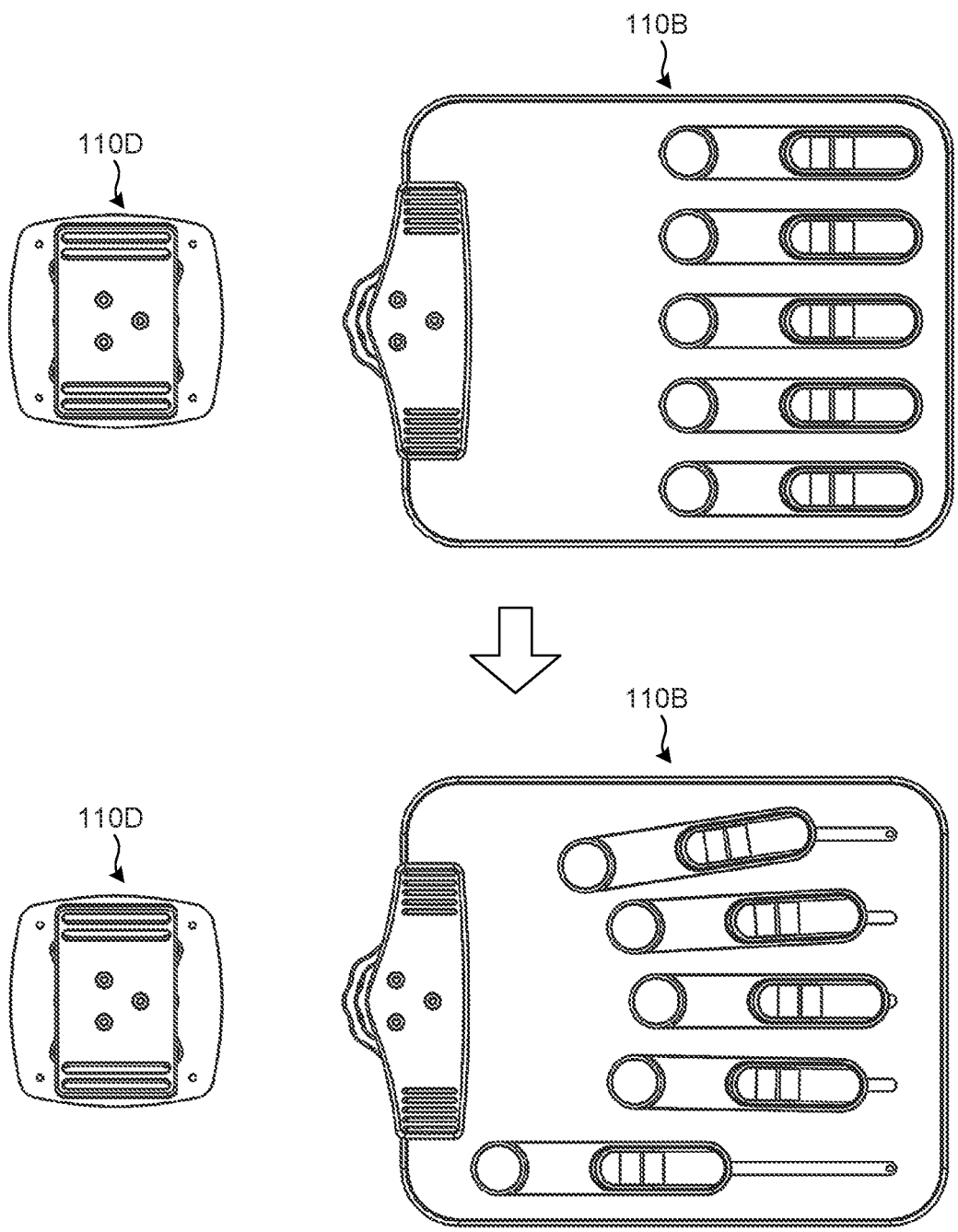
FIG. 42 is a top view of the force sensor and an armrest according to the second modification of the embodiment.

Next, an armrest according to the second modification of the embodiment will be described with reference to FIGS. 42 to 47. First, a description will be given with reference to FIG. 42. FIG. 42 is a top view of the force sensor 110B and an armrest 110D according to the second modification of the embodiment. As illustrated in FIG. 42, the force sensor 110B and the armrest 110D are used in a set. Specifically, the user places his/her arm on the armrest 110D and places his/her hand on the force sensor 110B.

In addition, as illustrated in FIG. 42, each of the five sensor units 110C moves on the upper surface of the support base 112B according to a posture of the finger. In addition, the processing unit 122 measures in advance the length of each of the two or more different fingers of the user using an image and a ruler. Subsequently, the processing unit 122 receives the posture of the finger subjected to measurement (how much the finger is laid down, or the like) from the user. Then, the processing unit 122 calculates the position of each of the two or more sensor units 110C on the upper surface of the support base 112B based on the posture of the two or more different fingers and the length of the finger of the user. Subsequently, the processing unit 122 moves each of the two or more sensor units 110C to the calculated position by driving an actuator built in the sensor unit 110C. Alternatively, the display unit 130 displays the position of each of the two or more sensor units 110C calculated by the processing unit 122. Then, the user may manually move each of the two or more sensor units 110C to the position displayed on the display unit 130.

Figure 43:
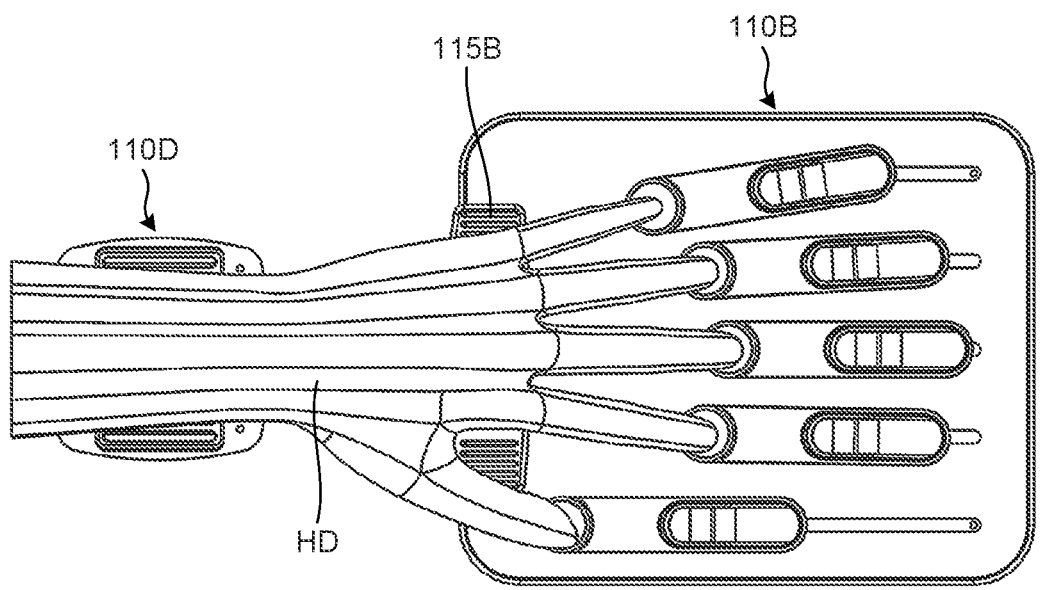
FIG. 43 is a top view illustrating positions of the force sensor, the armrest, and a hand of a user during measurement according to the second modification of the embodiment.

Next, a description will be given with reference to FIG. 43. FIG. 43 is a top view illustrating positions of the force sensor 110B, the armrest 110D, and a hand HD of the user during measurement according to the second modification of the embodiment. As illustrated in FIG. 43, the armrest 110D supports a part of the arm of the user. Specifically, the armrest 110D supports a region of the arm of the user about 5 to 10 cm below the wrist. The position of the armrest 110D with respect to the arm of the user may be adjusted so that the posture allows the user to easily make a measurement.

In addition, the support portion 115B of the palm rest supports the region connecting each MP joint of the index finger, the middle finger, the ring finger, and the little finger, and the central portion of the metacarpal in the palm of the user. In other words, the support portion 115B supports a region around the bases of the four fingers between the index finger to the little finger of the user, called a fingertip ball.

In addition, each of the five pressing portions 114B supports each of the fingertips of the fingers of the user.

Figure 44:
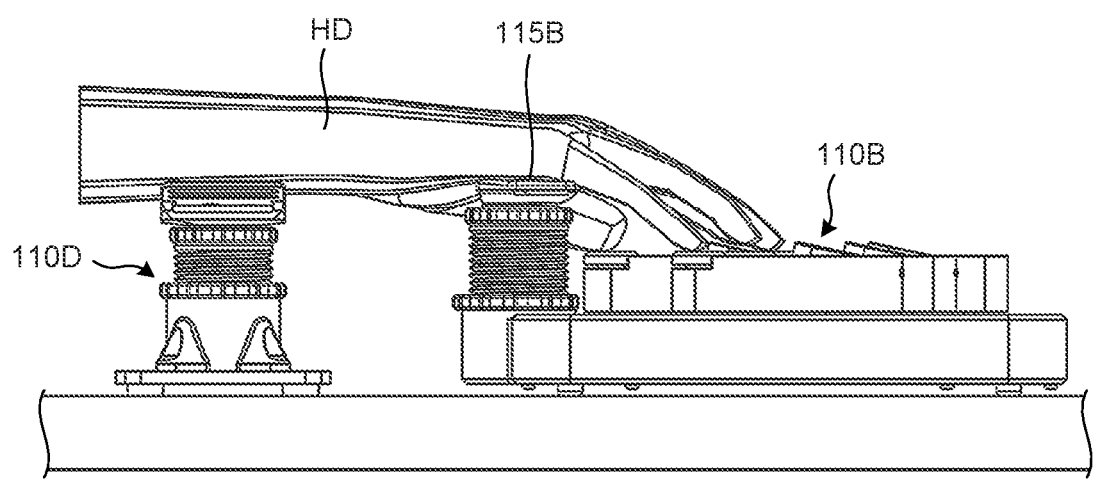
FIG. 44 is a side view illustrating the positions of the force sensor, the armrest, and the hand of the user during the measurement according to the second modification of the embodiment.

Next, a description will be given with reference to FIG. 44. FIG. 44 is a side view illustrating positions of the force sensor 110B, the armrest 110D, and a hand HD of the user during the measurement according to the second modification of the embodiment. As illustrated in FIG. 44, the height of the armrest 110D can be freely adjusted according to the height of the palm rest.

Figure 45:
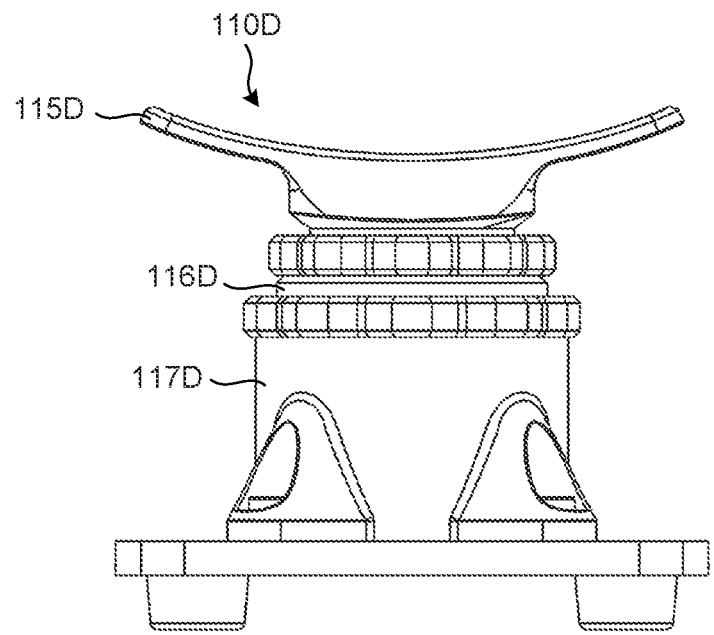
FIG. 45 is a side view of the armrest according to the second modification of the embodiment.

FIG. 45 is a side view of the armrest 110D according to the second modification of the embodiment. The armrest 110D is provided with a holding mechanism (not illustrated) that holds the support portion 115D so that the height of the support portion 115D can be changed in the direction perpendicular to the upper surface of the support base 112B. In addition, the armrest 110D is provided with the same double nut structure as that in the palm rest as an example of the holding mechanism (not illustrated). Specifically, the support portion 115D is a component integrated with a bolt portion 115E (see FIG. 47) having a bolt structure. In addition, the armrest 110D includes a first double nut 116D into which the bolt portion 115E is inserted and a second double nut 117D that fixes the first double nut 116D.

In the second modification described above, the dual double nut structure has been described as the example of the holding mechanism that holds the palm rest and the armrest 110D so that the heights can be changed, but the holding mechanism is not limited to the dual double nut structure. For example, the palm rest and the armrest 110D may be provided with a single double nut structure or a triple double nut structure as the example of the holding mechanism that holds the palm rest and the armrest 110D so that the height can be changed. In addition, the palm rest and the armrest 110D may be provided with a rack and pinion type (reference URL: https://ja.wikipedia.org/wiki/%E3A83%A9%E3%83%83%E3%82%AF%%E3%83%BB%E3%82%A2%E3%83%B3%E3%83%89%E3%83%BB%E3%83%94%E3%83%8B%E3%82%AA%E3%83%B3) structure as the example of the holding mechanism that holds the palm rest and the armrest 110D so that the height can be changed. Furthermore, the palm rest and the armrest 110D may be provided with a pantograph type (lab jack type) structure as the example of the holding mechanism that holds the palm rest and the armrest 110D so that the height can be changed. Also, the palm rest and the armrest 110D may be provided with a structure that combines the type in which a double pipe is fixed with a screw as the example of the holding mechanism that holds the palm rest and the armrest 110D so that the height can be changed.

Figure 46:
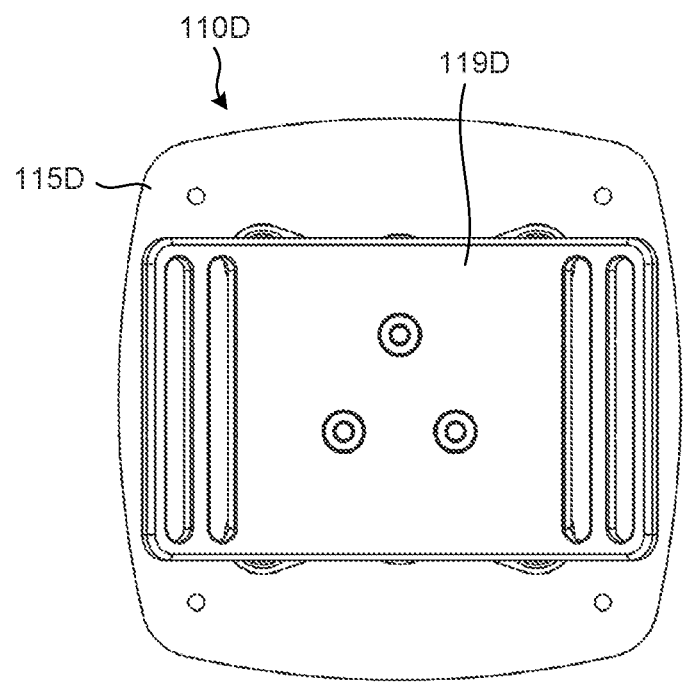
FIG. 46 is a top view of the armrest according to the second modification of the embodiment.

FIG. 46 is a top view of the armrest 110D according to the second modification of the embodiment. As illustrated in FIG. 45, a band 119D for fixing the arm of the user to the armrest 110D is attached on the upper surface of the support portion 115D. Grooves are provided at both ends of the band 119D, and it is possible to fix the arm according to the thickness of the arm of the user by changing the position of the groove.

Figure 47:
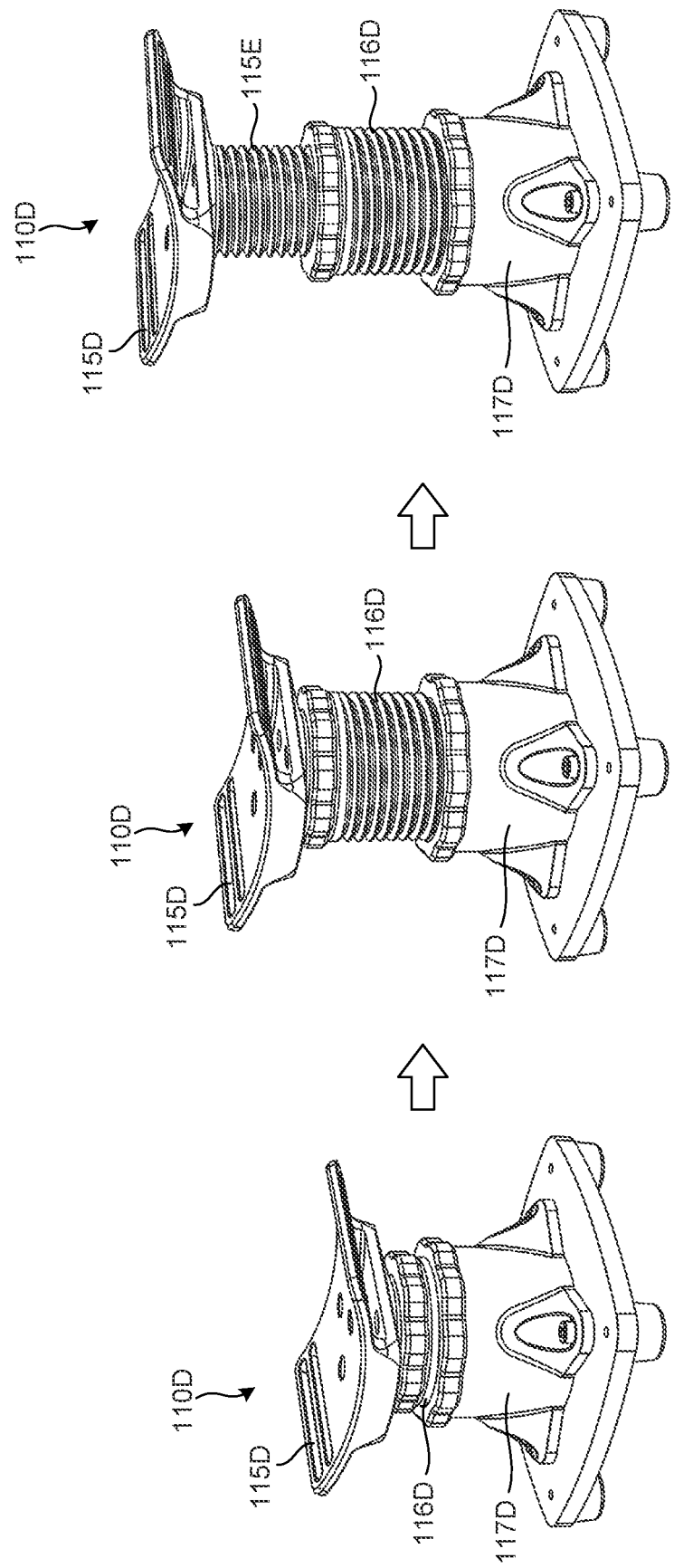
FIG. 47 is a perspective view of the armrest according to the second modification of the embodiment.

Next, a description will be given with reference to FIG. 47. FIG. 47 is a perspective view of the armrest 110D according to the second modification of the embodiment. As illustrated in FIG. 47, the support portion 115D is held so that the length of the bolt portion of the first double nut 116D can be changed in the direction perpendicular to the upper surface of the support base 112D in a state in which the second double nut 117D is loosened. In addition, the support portion 115D is held so that the length of the bolt portion 115E connected to the support portion 115D can be changed in the direction perpendicular to the upper surface of the support base 112D in a state in which the first double nut 116D is loosened.

As described above, the information processing apparatus 100 includes the dual double nut structure so that the height of the armrest can be adjusted in a compact manner. In addition, the information processing apparatus 100 has the dual double nut structure so that backlash can be reduced, allowing a stable measurement of the force of the finger.

Figure 48:
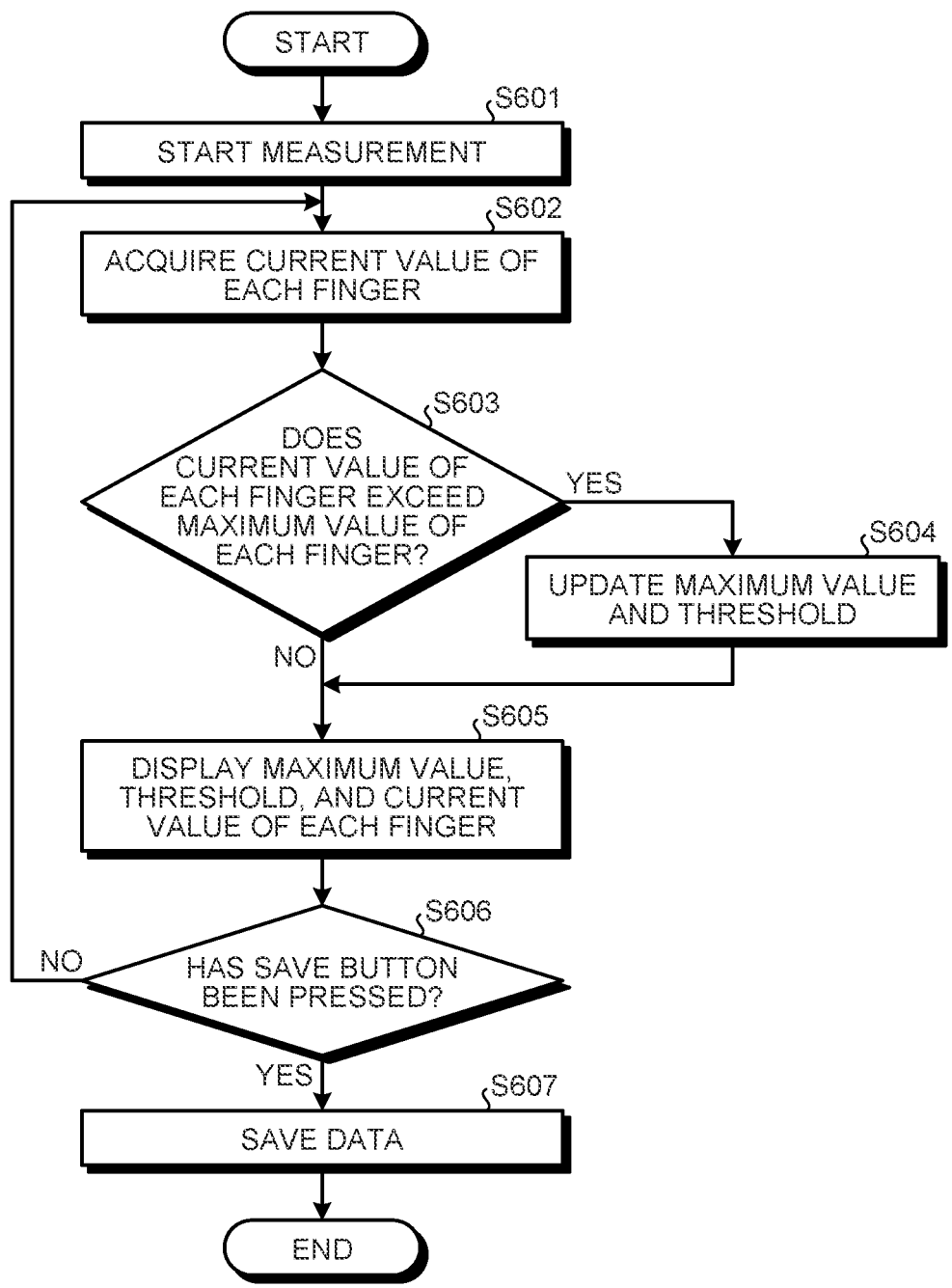
FIG. 48 is a flowchart illustrating a processing procedure of measurement of the force of each of five fingers when the force is simultaneously exerted by the fingers according to the second modification of the embodiment.
Figure 49:
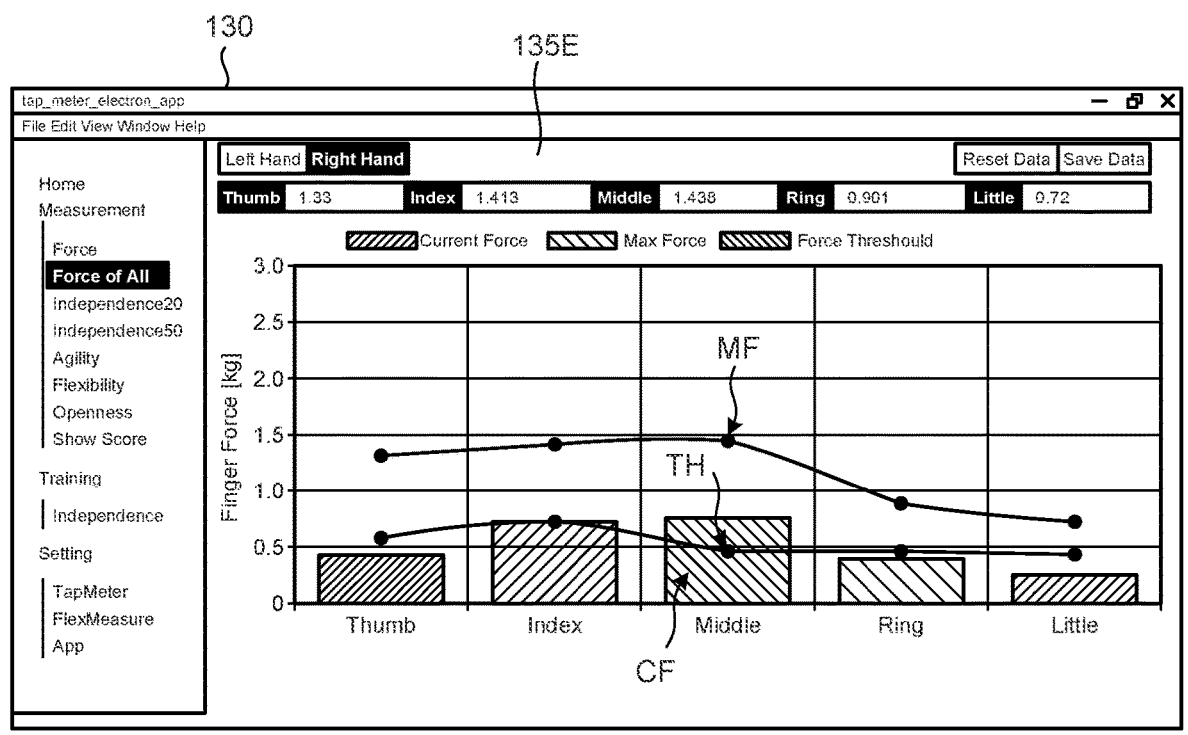
FIG. 49 is a flowchart illustrating an example of a display screen during the measurement of the force of each of five fingers when the force is simultaneously exerted by the fingers according to the second modification of the embodiment.
Figure 50:
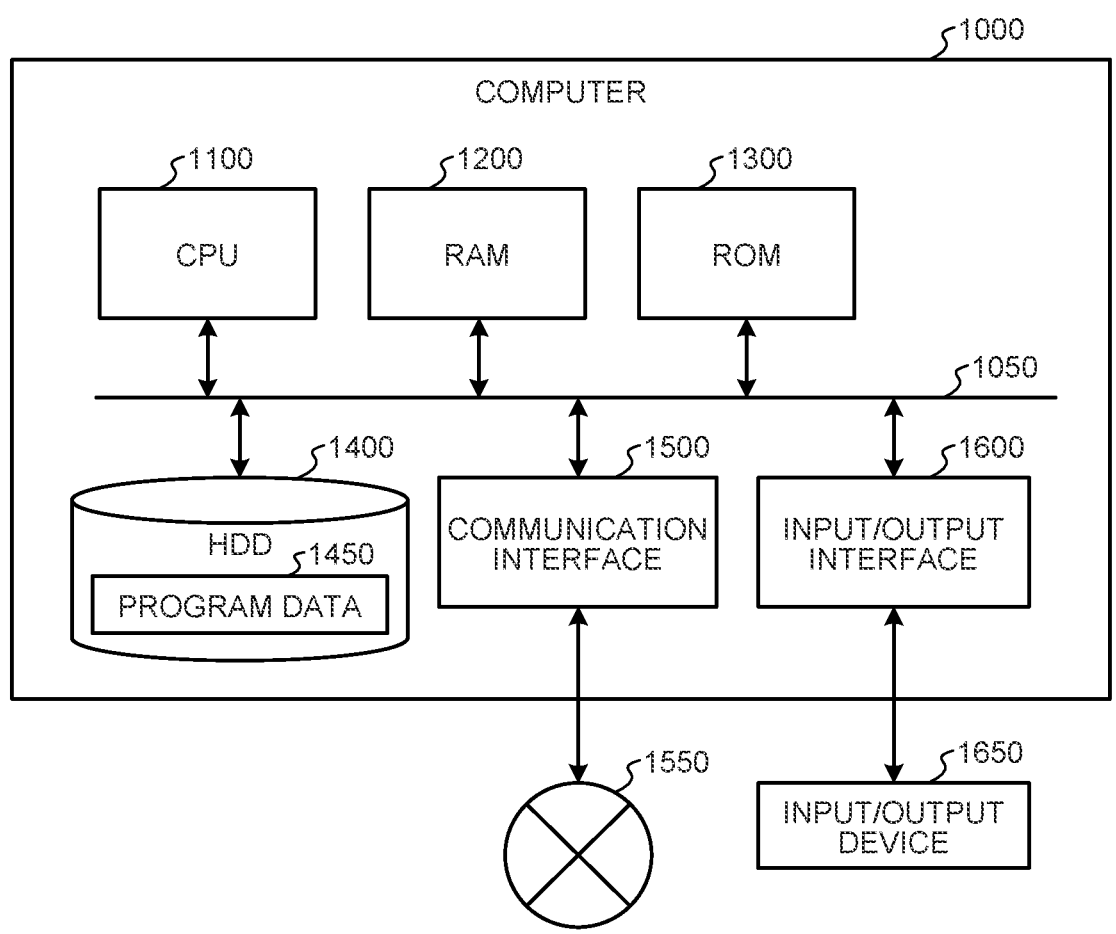
FIG. 50 is a hardware configuration diagram illustrating an example of a computer that implements functions of an information processing apparatus.

Next, processing of measurement of a relation between the forces of the fingers when the total of the forces of the five fingers is the maximum according to the second modification of the embodiment will be described with reference to FIGS. 48 to 49. First, a description will be given with reference to FIG. 48. FIG. 48 is a flowchart illustrating a processing procedure of the measurement of the relation between the forces of the fingers when the total of the forces of the five fingers is the maximum according to the second modification of the embodiment.

After receiving the setting related to the measurement of the relation between the forces of the fingers when the total of the forces of the five fingers is the maximum, the processing unit 122 starts the measurement of the force (Step S601). The processing unit 122 acquires the current value of the force of each finger (Step S602).

After acquiring the current value of the force of each finger, the processing unit 122 determines whether or not the current value of the force of each finger exceeds the maximum value of the force of each finger measured up to the present time (Step S603). When it is determined that the current value of the force of each finger does not exceed the maximum value (Step S603; No), the processing unit 122 displays the maximum value of the force of each finger measured up to the present time, a threshold of the force of each finger, and the current value of the force of each finger on the display unit 130 (Step S605). Here, the threshold of the force of each finger indicates the threshold of the force that needs to be exerted at the minimum by each finger. For example, as the threshold of the force of each finger, a value of a predetermined ratio (for example, 20% or the like) of the maximum value of the force of each finger measured up to the present time may be used.

On the other hand, when it is determined that any of the current values of the forces of the fingers exceeds the maximum value measured up to the present time (Step S603; Yes), the processing unit 122 updates the maximum value and the threshold of the force of the finger that has exceeded the maximum value measured up to the present time (Step S604). After updating the maximum value and the threshold of the force of the finger, the processing unit 122 displays the updated maximum value of the force of each finger, the updated threshold of the force of each finger, and the current value of the force of each finger on the display unit 130 (Step S605).

Subsequently, after displaying the maximum value of the force of each finger, the threshold of the force of each finger, and the current value of the force of each finger on the display unit 130, the processing unit 122 determines whether or not the save button has been pressed (Step S606). When it is determined that the save button has been pressed (Step S606: Yes), the processing unit 122 saves the measured data in the storage unit 140 (Step S607).

On the other hand, when it is determined that the save button has not been pressed (Step S606: No), the processing unit 122 returns to Step S602.

Next, a description will be given with reference to FIG. 49. FIG. 49 is a flowchart illustrating an example of a display screen during the measurement of the relation between the forces of the fingers when the total of the forces of the five fingers is the maximum according to the second modification of the embodiment. In the example illustrated in FIG. 49, the display unit 130 displays the maximum value of each finger of the right hand, the threshold of the force of each finger of the right hand, and the current value of the force of each finger of the right hand on the display screen 135E during the measurement. For example, when the middle finger is taken as an example, the display unit 130 displays a current value CF and a maximum value MF measured up to the present time of the force of the middle finger. In addition, the display unit 130 displays a threshold TH of the force of the middle finger.

2. Effects Related to the Present Disclosure

As described above, the information processing apparatus 100 according to the present disclosure includes the two or more force sensors and the processing unit 122. The two or more force sensors each detect the force of the two or more different fingers of the user. The processing unit 122 executes information processing related to measurement of the forces of the two or more different fingers based on detection results detected by each of the two or more force sensors.

With this configuration, the information processing apparatus 100 can measure the relation between the forces of the plurality of fingers. Therefore, the information processing apparatus 100 can appropriately measure the force of the finger.

In addition, the information processing apparatus 100 further includes the support base 112. The support base 112 is provided with the two or more holding mechanisms 116 that movably hold each of the two or more force sensors on the upper surface.

With this configuration, the information processing apparatus 100 can adjust the position of the force sensor. That is, the information processing apparatus 100 can accommodate various hand sizes and shapes of the user. That is, the information processing apparatus 100 can fix the force sensor at the measurement position optimum for each user. Therefore, since the information processing apparatus 100 can measure the force of each finger in a state in which each user maintains the correct posture of the hand, the reliability of sensing can be improved.

In addition, each of the two or more holding mechanisms 116 includes the fixing portion 113 that fixes each of the two or more force sensors to the support base 112. Each of the two or more force sensors is movably held on the upper surface by the holding mechanism 116 in a state in which the fixing portion 113 is loosened.

With this configuration, the information processing apparatus 100 can adjust the angle of the force sensor. That is, the information processing apparatus 100 can accommodate various hand sizes and shapes of the user. That is, the information processing apparatus 100 can fix the force sensor at the measurement position optimum for each user. Therefore, since the information processing apparatus 100 can measure the force of each finger in a state in which each user maintains the correct posture of the hand, the reliability of sensing can be improved.

In addition, the holding mechanism 116 movably holds each of the two or more force sensors on the upper surface along two or more rectangular grooves provided on the support base 112. At least two of the two or more rectangular grooves are parallel to each other. In addition, the two or more rectangular grooves are radially arranged such that one ends of the two or more rectangular grooves are closer to each other than the other ends.

With this configuration, the information processing apparatus 100 can adjust the position and angle of the force sensor.

In addition, the two or more force sensors have the same force detection direction.

With this configuration, the information processing apparatus 100 can appropriately measure the force of each finger in which the directions in which the forces of the fingers are input are aligned as in the case of tapping a keyboard of a piano, for example.

In addition, the information processing apparatus 100 further includes the support portion 115. The support portion 115 supports at least a part of the palm of the hand including the two or more different fingers of the user. In addition, the support portion 115 supports a region connecting each MP joint of the index finger, the middle finger, the ring finger, and the little finger in the palm and the CM joint of the thumb in the palm.

With this configuration, the information processing apparatus 100 can measure the force of the finger while preventing the force of the wrist from being transmitted because the base extends to the palm of the hand. In addition, the information processing apparatus 100 can appropriately measure the force of the finger without hindering the movement of each finger.

In addition, the information processing apparatus 100 further includes the two or more structures 111. The two or more structures 111 hold each of the two or more force sensors. Each of the two or more fixing portions 113 fixes each of the two or more structures 111 to the support base 112.

With this configuration, the information processing apparatus 100 can fix the force sensor to the support base without penetrating the force sensor.

In addition, each of the two or more structures 111 includes the pressing portion 114 indicating the place to be pressed by the finger of the user. The pressing portion 114 is provided on an upper surface of the structure 111.

With this configuration, the information processing apparatus 100 allows the user to easily perceive the place where the force sensor is pressed. In addition, the information processing apparatus 100 can stabilize the measurement value between trials and between persons subjected to evaluation by spatially limiting the pressing portion of the force sensor.

In addition, the processing unit 122 measures the magnitude of the force input to each of the two or more force sensors.

With this configuration, the information processing apparatus 100 can appropriately measure the force of each finger.

In addition, the processing unit 122 measures information indicating a relation between the forces input to each of the two or more force sensors.

With this configuration, the information processing apparatus 100 can appropriately measure the independence of the force of each finger.

In addition, the processing unit 122 measures the number of times of forces input to at least one of the two or more force sensors within a predetermined time.

With this configuration, the information processing apparatus 100 can appropriately measure the agility of the force of the finger.

In addition, the processing unit 122 measures variation in the magnitude between the forces input to at least one of the two or more force sensors.

With this configuration, the information processing apparatus 100 can appropriately measure the repetitive reproducibility of the tapping force of the finger.

In addition, the processing unit 122 measures a time interval between the forces input to at least one of the two or more force sensors.

With this configuration, the information processing apparatus 100 can appropriately measure the temporal accuracy of the tapping operation of the finger.

In addition, the information processing apparatus 100 further includes the display unit 130. The display unit 130 displays information related to measurement results of the forces of the two or more different fingers measured by the processing unit 122. In addition, the display unit 130 displays the information indicating the relation between the forces of the two or more different fingers measured by the processing unit 122.

With this configuration, the information processing apparatus 100 can feed back the measurement results to the user. In addition, the information processing apparatus 100 can recommend training to the user. Therefore, the information processing apparatus 100 can improve the skill of the finger of the user.

3. Hardware Configuration

Information equipment such as the information processing apparatus 100 according to the above-described embodiment and modification is realized by a computer 1000 having a configuration as illustrated in FIG. 27, for example. FIG. 27 is a hardware configuration diagram illustrating an example of the computer 1000 that implements a function of the information processing apparatus such as the information processing apparatus 100. Hereinafter, the information processing apparatus 100 according to the embodiment will be described as an example. The computer 1000 includes a CPU 1100, a RAM 1200, a read only memory (ROM) 1300, a hard disk drive (HDD) 1400, a communication interface 1500, and an input/output interface 1600. Each unit of the computer 1000 is connected by a bus 1050.

The CPU 1100 operates based on a program stored in the ROM 1300 or the HDD 1400, and controls each unit. For example, the CPU 1100 deploys a program stored in the ROM 1300 or the HDD 1400 to the RAM 1200, and executes processing corresponding to various programs.

The ROM 1300 stores a boot program such as a basic input output system (BIOS) executed by the CPU 1100 when the computer 1000 starts up, a program dependent on hardware of the computer 1000, and the like.

The HDD 1400 is a computer-readable recording medium that non-transiently records a program executed by the CPU 1100, data used by the program, and the like. Specifically, the HDD 1400 is a recording medium that records an information processing program according to the present disclosure serving as an example of program data 1350.

The communication interface 1500 is an interface for the computer 1000 to connect to an external network 1550 (for example, the Internet). For example, the CPU 1100 receives data from another device or transmits data generated by the CPU 1100 to the other device via the communication interface 1500.

The input/output interface 1600 is an interface for connecting an input/output device 1650 and the computer 1000. For example, the CPU 1100 receives data from an input device such as a keyboard and a mouse via the input/output interface 1600. In addition, the CPU 1100 transmits data to an output device such as a display, a speaker, or a printer via the input/output interface 1600. Furthermore, the input/output interface 1600 may function as a media interface that reads a program or the like recorded in a predetermined recording medium (medium). The medium is, for example, an optical recording medium such as a digital versatile disc (DVD) or a phase change rewritable disk (PD), a magneto-optical recording medium such as a magneto-optical disk (MO), a tape medium, a magnetic recording medium, a semiconductor memory, or the like.

For example, when the computer 1000 functions as the information processing apparatus 100 according to the embodiment, the CPU 1100 of the computer 1000 implements the functions of the control unit 120 and the like by executing an information processing program loaded on the RAM 1200. In addition, the HDD 1400 stores the information processing program according to the present disclosure and data in the storage unit 140. The CPU 1100 reads the program data 1350 from the HDD 1400 and executes the program data, but as another example, these programs may be acquired from another device via the external network 1550.

The present technique may also have the following configurations:

(1)

An information processing apparatus comprising:
two or more force sensors that each detect a force of two or more different fingers of a user; and
a processing unit that executes information processing related to measurement of forces of the two or more different fingers based on detection results detected by each of the two or more force sensors.

(2)

The information processing apparatus according to (1), further comprising:
a first support base provided with two or more first holding mechanisms that movably hold each of the two or more force sensors on an upper surface.

(3)

The information processing apparatus according to (2), wherein each of the two or more first holding mechanisms includes a first fixing portion that fixes each of the two or more force sensors to the first support base, and
each of the two or more force sensors is movably held on the upper surface by the first holding mechanism in a state in which the first fixing portion is loosened.

(4)

The information processing apparatus according to (2) or (3),
wherein the first holding mechanism movably holds each of the two or more force sensors on the upper surface along two or more rectangular grooves provided on the first support base.

(5)

The information processing apparatus according to (4) above,
wherein at least two of the two or more rectangular grooves are parallel to each other.

(6)

The information processing apparatus according to (4),
wherein the two or more rectangular grooves are radially arranged such that one ends of the two or more rectangular grooves are closer to each other than the other ends.

(7)

The information processing apparatus according to any one of (1) to (6) above,
wherein the two or more force sensors have the same force detection direction.

(8)

The information processing apparatus according to any one of (1) to (6),
wherein the two or more force sensors are triaxial force sensors.

(9)

The information processing apparatus according to any one of (1) to (8), further comprising:
a first support portion that supports at least a part of a palm of a hand including the two or more different fingers of the user.

(10)

The information processing apparatus according to (9) above,
wherein the first support portion supports a region connecting each MP joint of the index finger, the middle finger, the ring finger, and the little finger in the palm, and the CM joint of the thumb in the palm.

(11)

The information processing apparatus according to (9),
wherein the first support portion supports a region connecting each MP joint of an index finger, a middle finger, a ring finger, and a little finger, and a central portion of a metacarpal in the palm.

(12)

The information processing apparatus according to any one of (9) to (11), further comprising:
a first support base provided with two or more first holding mechanisms that movably hold each of the two or more force sensors on an upper surface; and
a second holding mechanism that holds the first support portion so that a height of the first support portion can be changed in a direction perpendicular to the upper surface of the first support base,
wherein the second holding mechanism includes a second fixing portion that fixes the first support portion to the first support base, and
the first support portion is held by the second holding mechanism so that the height can be changed in the direction perpendicular to the upper surface of the first support base in a state where the second fixing portion is loosened.

(13)

The information processing apparatus according to any one of (1) to (12), further comprising:
a second support portion that supports at least a part of an arm of a hand including the two or more different fingers of the user.

(14)

The information processing apparatus according to (13), further comprising:
a first support base provided with two or more first holding mechanisms that movably hold each of the two or more force sensors on an upper surface; and
a second support base provided with a third holding mechanism that holds the second support portion so that a height of the second support portion can be changed in a direction perpendicular to the upper surface of the first support base,
wherein the third holding mechanism includes a third fixing portion that fixes the second support portion to the second support base, and
the second support portion is held by the third holding mechanism so that the height can be changed in the direction perpendicular to the upper surface of the first support base in a state where the third fixing portion is loosened.

(15)

The information processing apparatus according to any one of (3) to (14), further comprising:
two or more structures that hold each of the two or more force sensors,
wherein each of the two or more first fixing portions fixes each of the two or more structures to the first support base.

(16)

The information processing apparatus according to (15) above,
wherein each of the two or more structures has a pressing portion indicating a place to be pressed by the finger of the user, and
the pressing portion is provided on an upper surface of the structure.

(17)

The information processing apparatus according to any one of (1) to (16),
wherein the processing unit measures a magnitude of a force input to each of the two or more force sensors.

(18)

The information processing apparatus according to any one of (1) to (17),
wherein the processing unit measures information indicating a relation between the forces input to each of the two or more force sensors.

(19)

The information processing apparatus according to (18),
wherein the processing unit measures the information indicating the relation between the forces input to each of the two or more force sensors when a total of magnitudes of the forces input to each of the two or more force sensors is a maximum during a measurement.

(20)

The information processing apparatus according to any one of (1) to (19) above,
wherein the processing unit measures the number of times of forces input to at least one of the two or more force sensors within a predetermined time.

(21)

The information processing apparatus according to any one of (1) to (20) above,
wherein the processing unit measures variation in the magnitude between the forces input to at least one of the two or more force sensors.

(22)

The information processing apparatus according to any one of (1) to (21) above,
wherein the processing unit measures a time interval between the forces input to at least one of the two or more force sensors.

(23)

The information processing apparatus according to any one of (2) to (22),
wherein the processing unit calculates a position of each of the two or more force sensors on the upper surface of the first support base based on a posture of the two or more different fingers and a length of the finger of the user.

(24)

The information processing apparatus according to any one of (2) to (22),
wherein the processing unit measures the position of each of the two or more force sensors on the upper surface of the first support base.

(25)

The information processing apparatus according to any one of (1) to (24), further comprising
a display unit that displays information related to measurement results of the forces of the two or more different fingers measured by the processing unit.

(26)

The information processing apparatus according to (25) above,
wherein the display unit displays information indicating the relation between the forces of the two or more different fingers measured by the processing unit.

(27)

The information processing apparatus according to (25) or (26),
wherein the display unit displays information indicating a ratio of the force of another finger to the force of a predetermined finger among the two or more different fingers measured by the processing unit.

(28)

The information processing apparatus according to any one of (25) to (27) above,
wherein the display unit further displays information related to a preset target value related to the force of the finger of the user.

(29)

The information processing apparatus according to any one of (1) to (28) above,
wherein the processing unit executes information processing related to evaluation of the forces of the two or more different fingers based on a history of measurement results of the forces of the two or more different fingers.

(30)

The information processing apparatus according to any one of (1) to (29) above, further including
a display unit that displays information related to the history of the measurement results of the forces of the two or more different fingers.

(31)

The information processing apparatus according to any one of (1) to (30) above, further including
a display unit that displays recommendation information related to training of the finger of the user based on the history of the measurement results of the forces of the two or more different fingers.

(32)

The information processing apparatus according to any one of (1) to (31) above, further including
an acquisition unit that acquires information related to measurement results of forces of two or more different fingers of another user who is different from the user,
wherein the processing unit executes information processing related to the evaluation of the forces of the two or more different fingers of the user based on the information related to the measurement results of the forces of the two or more different fingers of the other user.

(33)

The information processing apparatus according to (32) above, further including
a display unit that displays information related to comparison results between the measurement results of the forces of the two or more different fingers of the other user and the measurement results of the forces of the two or more different fingers of the user.

(34)

The information processing apparatus according to (33) above,
wherein the display unit displays recommendation information related to training of the two or more different fingers of the user based on the comparison results between the measurement results of the forces of the two or more different fingers of the other user and the measurement results of the forces of the two or more different fingers of the user.

(35)

An information processing method of controlling an information processing apparatus including two or more force sensors that each detect a force of two or more different fingers of a user, the method comprising:
executing information processing related to measurement of the forces of the two or more different fingers based on detection results detected by each of the two or more force sensors.

(36)

An information processing program that functions a processor that controls an information processing apparatus including two or more force sensors that each detect a force of two or more different fingers of a user, the program that causes the processor to execute:
information processing related to measurement of the forces of the two or more different fingers based on detection results detected by each of the two or more force sensors.

REFERENCE SIGNS LIST

1 INFORMATION PROCESSING SYSTEM
100 INFORMATION PROCESSING APPARATUS
110 FORCE SENSOR
120 CONTROL UNIT
121 SENSOR PROCESSING UNIT
122 PROCESSING UNIT
130 DISPLAY UNIT
140 STORAGE UNIT
150 COMMUNICATION UNIT
200 DATABASE
300 TERMINAL DEVICE
400 ANALYSIS SERVER

The invention claimed is:

1. An information processing system comprising:
two or more force sensors, each sensor being configured to detect a force of two or more different fingers of a user;
a first support base provided with at least two first holding mechanisms, each first holding mechanism configured to movably hold a respective force sensor of the two or more force sensors on an upper surface; and
a processing unit configured to execute information processing related to measurement of forces of the two or more different fingers based on detection results detected by each of the two or more force sensors,
wherein each first holding mechanism movably holds the respective force sensor of the two or more force sensors on the upper surface along at least one groove provided on the first support base, and wherein the processing unit is implemented via at least one processor.

2. The information processing system according to claim 1,
wherein each of the two or more first holding mechanisms includes a respective first fixing portion that fixes the respective force sensor of the two or more force sensors to the first support base, and
each of the two or more force sensors is movably held on the upper surface by a respective first holding mechanism in a state in which the respective first fixing portion is loosened.

3. The information processing system according to claim 2, further comprising:
two or more structures that hold each of the two or more force sensors,
wherein each of two or more first fixing portions fixes each of the two or more structures to the first support base.

4. The information processing system according to claim 1,
wherein each first holding mechanism movably holds the respective force sensor of the two or more force sensors on the upper surface along one or more rectangular grooves provided on the first support base.

5. The information processing system according to claim 4,
wherein two or more rectangular grooves are radially arranged such that first ends of the two or more rectangular grooves are closer to each other than second ends.

6. The information processing system according to claim 1,
wherein the two or more force sensors are triaxial force sensors.

7. The information processing system according to claim 1, further comprising:
a first support portion that supports at least a part of a palm of a hand including the two or more different fingers of the user.

8. The information processing system according to claim 7,
wherein the first support portion supports a region connecting each MP joint of an index finger, a middle finger, a ring finger, and a little finger, and a central portion of a metacarpal in the palm.

9. The information processing system according to claim 7, further comprising:
a first support base provided with two or more first holding mechanisms that movably hold each of the two or more force sensors on an upper surface; and
a second holding mechanism that holds the first support portion so that a height of the first support portion can be changed in a direction perpendicular to the upper surface of the first support base,
wherein the second holding mechanism includes a second fixing portion that fixes the first support portion to the first support base, and
the first support portion is held by the second holding mechanism so that the height can be changed in the direction perpendicular to the upper surface of the first support base in a state where the second fixing portion is loosened.

10. The information processing system according to claim 1, further comprising:
a second support portion that supports at least a part of an arm of a hand including the two or more different fingers of the user.

11. The information processing system according to claim 10, further comprising:
a first support base provided with two or more first holding mechanisms that movably hold each of the two or more force sensors on an upper surface; and
a second support base provided with a third holding mechanism that holds the second support portion so that a height of the second support portion can be changed in a direction perpendicular to the upper surface of the first support base,
wherein the third holding mechanism includes a third fixing portion that fixes the second support portion to the second support base, and
the second support portion is held by the third holding mechanism so that the height can be changed in the direction perpendicular to the upper surface of the first support base in a state where the third fixing portion is loosened.

12. The information processing system according to claim 1,
wherein the processing unit is further configured to measure a magnitude of a force input to each of the two or more force sensors.

13. The information processing system according to claim 1,
wherein the processing unit is further configured to measure information indicating a relation between the forces input to each of the two or more force sensors.

14. The information processing system according to claim 13,
wherein the processing unit measures the information indicating the relation between the forces input to each of the two or more force sensors when a total of magnitudes of the forces input to each of the two or more force sensors is a maximum during a measurement.

15. The information processing system according to claim 1,
wherein the processing unit is further configured to calculate a position of each of the two or more force sensors on the upper surface of the first support base based on a posture of the two or more different fingers and a length of the finger of the user.

16. The information processing system according to claim 1,
wherein the processing unit is further configured to measure the position of each of the two or more force sensors on the upper surface of the first support base.

17. The information processing system according to claim 1, further comprising:
a display unit configured to display information related to measurement results of the forces of the two or more different fingers measured by the processing unit.

18. An information processing method of controlling an information processing system, the method comprising:
executing information processing related to measurement of forces of two or more different fingers based on detection results detected by each of two or more force sensors,
wherein the information processing system includes
the two or more force sensors that each detect a force of the two or more different fingers of a user, and
a first support base provided with at least two first holding mechanisms, each first holding mechanism configured to movably hold a respective force sensor configured to movably hold each of the two or more force sensors on an upper surface, and wherein each first holding mechanism movably holds the respective force sensor of the two or more force sensors on the upper surface along at least one groove provided on the first support base.

19. A non-transitory computer-readable storage medium having embodied thereon an information processing program, which when executed by a processor of a computer that controls an information processing system, causes the processor to execute a method, the method comprising:

executing information processing related to measurement of forces of two or more different fingers based on detection results detected by each of two or more force sensors, wherein the information processing system includes
the two or more force sensors that each detect a force of the two or more different fingers of a user, and
a first support base provided with at least two first holding mechanisms, each first holding mechanism configured to movably hold a respective force sensor of the two or more force sensors on an upper surface, and wherein each first holding mechanism movably holds the respective force sensor of the two or more force sensors on the upper surface along at least one groove provided on the first support base.

* * * * *